(12) United States Patent
Klaassen et al.

(10) Patent No.: US 10,450,588 B2
(45) Date of Patent: Oct. 22, 2019

(54) GLYCEROL AND ACETIC ACID CONVERTING YEAST CELLS WITH IMPROVED ACETIC ACID CONVERSION

(71) Applicant: DSM IP ASSETS B.V., Heerlen (NL)

(72) Inventors: Paul Klaassen, Echt (NL); Antonius Willem Wouter Hartman, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/914,612

(22) PCT Filed: Aug. 29, 2014

(86) PCT No.: PCT/EP2014/068324
§ 371 (c)(1),
(2) Date: Feb. 25, 2016

(87) PCT Pub. No.: WO2015/028582
PCT Pub. Date: Mar. 5, 2015

(65) Prior Publication Data
US 2016/0208291 A1 Jul. 21, 2016

(30) Foreign Application Priority Data

Aug. 29, 2013 (EP) .................................. 13182222

(51) Int. Cl.
*C12N 1/16* (2006.01)
*C12P 7/06* (2006.01)
(Continued)

(52) U.S. Cl.
CPC ............. *C12P 7/10* (2013.01); *C12N 1/16* (2013.01); *C12N 9/0006* (2013.01); *C12N 9/0008* (2013.01); *C12N 9/1205* (2013.01);

*C12N 9/93* (2013.01); *C12P 7/06* (2013.01); *C12Y 101/01006* (2013.01);
(Continued)

(58) Field of Classification Search
None
See application file for complete search history.

(56) References Cited

U.S. PATENT DOCUMENTS

2015/0050696 A1 2/2015 Roubos et al.
2015/0176032 A1 6/2015 De Bont et al.

FOREIGN PATENT DOCUMENTS

WO 2010051324 A1 5/2010
WO 2011010923 A1 1/2011
(Continued)

OTHER PUBLICATIONS

GenBank Accession No. AAA23420.1, published Apr. 26, 1993.*
(Continued)

*Primary Examiner* — Richard C Ekstrom
(74) *Attorney, Agent, or Firm* — McBee Moore Woodward & Vanik IP, LLC

(57) ABSTRACT

Cell that is genetically modified comprising:
a) one or more nucleotide sequence encoding a NAD+-dependent acetylating acetaldehyde dehydrogenase (E.C. 1.2.1.10);
b) one or more nucleotide sequence encoding a acetyl-CoA synthetase (E.C. 6.2.1.1);
c) one or more nucleotide sequence encoding a glycerol dehydrogenase (E.C. 1.1.1.6); and
d) one or more nucleotide sequence encoding a dihydroxyacetone kinase (E.C. 2.7.1.28 or E.C. 2.7.1.29).

5 Claims, 8 Drawing Sheets
Specification includes a Sequence Listing.

(51) Int. Cl.
*C12P 7/10* (2006.01)
*C12N 9/04* (2006.01)
*C12N 9/02* (2006.01)
*C12N 9/00* (2006.01)
*C12N 9/12* (2006.01)

(52) U.S. Cl.
CPC ............... *C12Y 102/0101* (2013.01); *C12Y 207/01028* (2013.01); *C12Y 207/01029* (2013.01); *C12Y 602/01001* (2013.01); *Y02E 50/16* (2013.01); *Y02E 50/17* (2013.01)

(56) References Cited

FOREIGN PATENT DOCUMENTS

| WO | 2011149353 A1 | 12/2011 |
|---|---|---|
| WO | 2012067510 A1 | 5/2012 |
| WO | 2013081456 A2 | 6/2013 |
| WO | 2013144257 A1 | 10/2013 |
| WO | 2014074895 A1 | 5/2014 |

OTHER PUBLICATIONS

Geneseq Accession No. AWG12187, published Apr. 2, 2009.*
UniProt Accession No. Q6C2B3_YARLI, published Aug. 14, 2004 (Year: 2004).*
International Search Report from corresponding PCT/EP2014/068324, dated Mar. 31, 2015.
Engler et al., "Generation of Families of Construct Variants Using Golden Gate Shuffling" Methods in Molecular Biology (2011) vol. 729: 167-181.
Medina et al., "Elimination of Glycerol Production in Anaerobic Cultures of a *Saccharomyces cerevisiae* Strain Engineered to Use Acetic Acid as an Electron Acceptor" Applied and Environmental Microbiology. (Jan. 2010) vol. 76, No. 1: 190-195.
Lee et al., "Application of sequential integration for metabolic engineering of 1,2-propanediol production in yeast" Metabolic Engineering. (2006) vol. 8: 58-65.
Sonderegger et al., "Metabolic Engineering of a Phosphoketolase Pathway for Pentose Catabolism in *Saccharomyces cerevisiae*" Applied and Environmental Microbiology. (2004) vol. 70, No. 5: 2892-2897.
Van Dijken et al., "Redox balances in the metabolism of sugars by yeast" FEMS Microbiology Review. (1986) vol. 32: 199-224.
Truniger et al., "Mapping and Cloning of gldA, the Structural Gene of the *Escherichia coli* Glycerol Dehydrogenase" Journal of Bacteriology. (May 1994) vol. 176, No. 6: 1796-1800.
Kleerebezem et al., "Complete genome sequence of Lactobacillus plantarum" Uniprot:F9UTT1. (Oct. 19, 2011) p. 1. XP002718834.
Yamamoto et al., "Construction of a contiguous 874-kb sequence of the *Escherichia coli*—K12 genome corresponding to 50.0-68.8 min on the linkage map and analysis of its sequence features" UNIPROT:P77445. (Nov. 13, 2013) p. 1. XP00278835.
Gonzalez et al., "Production of ethanol from thin stillage by metabolically engineered *Escherichia coli*" Biotechnology Letters. (2010) vol. 32:405-411.
Yazdani et al., "Engineering *Escherichia coli* for the efficient conversion of glycerol to ethanol and co-products" Metabolic Engineering. (2008) vol. 10:340-351.
Nguyen et al., "Engineering of *Saccharomyces cerevisiae* for the production of dihydroxyacetone (DHA) from sugars: A proof of concept" Metabolic Engineering. (2009) vol. 10:335-346.
Yu et al., "Engineering of glycerol utilization pathway for ethanol production for *Saccharomyces cerevisiae*" Bioresource Technology. (2010) vol. 101:4157-4161.
Yu et al., "Improvment of Ethanol Yield from Glycerol via Conversion of Pyruvate to Ethanol in Metabolically Engineered *Saccaromyces cerevisiae*" Applied Biochemistry Biotechnology. (2012) vol. 166: 856-865.
Dujon, B., "hypothetical protein [Yarrowia lipolytica CLIB99]", NCBI, Accession No. XP_505199.

* cited by examiner

GLYCEROL AND ACETIC ACID CONVERTING YEAST CELLS WITH IMPROVED ACETIC ACID CONVERSION

CROSS REFERENCE TO RELATED APPLICATIONS

This application is a § 371 National Stage Application of PCT/EP2014/068324, filed 29 Aug. 2014 which claims priority to EP 13182222.3, filed 29 Aug. 2013.

BACKGROUND

Field of the Invention

The present invention relates to metabolic engineering in microorganisms such as yeast. In particular the invention relates glycerol and acetic acid converting yeast cells with improved acetic acid conversion. The invention further relates to the processes wherein the yeast cells produce fermentation product such as ethanol.

Description of Related Art

Second generation bioethanol is produced from e.g. lignocellulosic fractions of plant biomass that is hydrolyzed into free monomeric sugars, such as hexoses and pentoses, for fermentation into ethanol. Apart from the sugar release during pretreatment and hydrolysis of the biomass, some toxic by-products are formed. For instance, furfural and HMF are two of these products. The quantities in which they are formed depend on several pretreatment parameters, such as temperature, pressure and pretreatment time. Lignocellulosic hydrolysates also contain high amounts of acetic acid, which is a potent inhibitor of the fermentative capacity of microorganisms, such as yeasts.

Glycerol is the major by-product during fermentation of sugars into ethanol, mainly formed as a result of re-oxidation reactions to consume the excess NADH formed during biosynthesis under anaerobic conditions (van Dijken and Scheffers, 1986). As a result, during industrial fermentations, about 5 to 10% of the consumed sugars by yeast cells are diverted into glycerol. Lowering the amount of this polyol is considered a promising route to increase ethanol yield. This could be achieved by adjusting the feeding rate during the fed-batch process, or by selecting strains that produce less glycerol.

In the literature, however, several different approaches have been reported that could help to reduce the inhibitory effect of acetic acid on the fermentation of the sugars in hydrolysates as well as (partly) solving redox balance issues upon deletion of the genes involved in glycerol production, e.g. by genetic engineering of yeasts.

Sonderegger et al (2004) disclosed the heterologous expression of phosphotransacetylase and acetaldehyde dehydrogenase in a xylose-fermenting *Saccharomyces cerevisiae* strain. In combination with the native phosphoketolase. Sonderegger et al thereby created a functional phosphoketolase pathway that is capable of net reoxidation of NADH generated by the heterologous expression of a xylose reductase and xylitol dehydrogenase that are used for xylose utilization in that particular strain.

Guadalupe et al (2009) described a *Saccharomyces cerevisiae* strain wherein production of the by-product glycerol is eliminated by the disruption of the endogenous NAD-dependent glycerol 3-phosphate dehydrogenase genes (GPD1 and GPD2). Expression of the *E. coli* mhpF gene, encoding the acetylating NAD-dependent acetaldehyde dehydrogenase, restored the ability of the gpd1gpd2 double deletion strain to grow anaerobically by supplementation of the medium with acetic acid.

Yu et al (2010) constructed *Saccharomyces cerevisiae* strains metabolically engineered for improved ethanol production from glycerol by simultaneous overexpression of glycerol dehydrogenase (encoded by GCY1), dihydroxyacetone kinase (DAK1) and the glycerol uptake protein (GUP1). In a later report by the same group (Yu et al, 2011) it is described that additional overexpression of ADH1 and PDC1, encoding alcohol dehydrogenase and pyruvate decarboxylase respectively, caused an increase in growth rate and glycerol consumption under fermentative conditions, resulting in a slightly increased final ethanol yield.

Lee and Dasilva (2006) disclosed the yeast *Saccharomyces cerevisiae* engineered to produce 1,2-propanediol from glycerol by amongst others introducing expression of the *Escherichia coli* mgs and gldA genes.

The technology described by Guadelupe et al (and also in patent application WO 2011/010923) provides a solution for decreasing the acetic acid content of hydrolysates during fermentation of the biomass sugars and the aforementioned acetic acid into e.g. ethanol.

Further enhancement of the ability to convert acetic acid is potentially possible by introducing an extra NADH-generating pathway, e.g. by additionally (over-)expressing a glycerol consumption pathway. Upon introduction of the aforementioned GUP1-, GCY1- and DAK1-genes (Yu et al, 2010) in a yeast strain expressing an anaerobic acetic acid conversion pathway (such as e.g. described by Medina et al, 2009), acetic acid conversion should be increased in order to maintain the redox balance, leading to further increased detoxification of the hydrolysate and higher ethanol yield. The solution of Yu et al however, does not work, since the yeast glycerol dehydrogenase (encoded by GCY1) uses $NADP^+$ as a co-factor, resulting in a cofactor imbalance due to insufficient cofactor regeneration. An alternative glyceroldehydrogenase (gldA from *E. coli*) was tested in combination with the acetic acid reduction pathway and indeed enhanced the conversion of acetic acid under anaerobic growth (fermentation) conditions (patent application WO2013/081456).

SUMMARY OF THE INVENTION

It is therefore an object of the present invention to provide for yeasts that are capable of producing ethanol from acetic acid or acetate while retaining their abilities of fermenting hexoses (glucose, fructose, galactose, etc) as well as pentoses like xylose, as well as processes wherein these strains are used for the production of ethanol and/or other fermentation products. An object is to provide for cells, e.g. yeast cells that are capable of producing ethanol from glycerol and/or glycerol and acetic acid while retaining their abilities of fermenting hexoses (glucose, fructose, galactose, etc) as well as pentoses like xylose. Another object is to increase the production of fermentation product (yield, production rate or both).

One or more of the objects are attained according to the invention that provides a yeast cell that is genetically modified comprising:

a) one or more nucleotide sequence encoding a heterologous NAD+-dependent acetylating acetaldehyde dehydrogenase (E.C. 1.2.1.10);

b) one or more nucleotide sequence encoding a homologous or heterologous acetyl-CoA synthetase (E.C. 6.2.1.1);

c) one or more nucleotide sequence encoding a heterologous glycerol dehydrogenase (E.C. 1.1.1.6); and d) one or more nucleotide sequence encoding a homologous or heterologous dihydroxyacetone kinase (E.C. 2.7.1.28 or E.C. 2.7.1.29).

In an embodiment, the cell has a deletion or disruption of one or more endogenous nucleotide sequence encoding a glycerol 3-phosphate phosphohydrolase and/or encoding a glycerol 3-phosphate dehydrogenase gene.

One or more of the above objects are attained according to the invention.

It is clear from the examples that according to the invention improved fermentation product production (ethanol) may be attained.

The ethanol yield per consumed sugar (glucose and/or other sugars) increases due to elimination of glycerol production, ethanol generation from acetate/acetic acid in the medium (and always present in lignocellulosic hydrolysates) and glycerol externally added to the medium (or hydrolysate).

Figure 1:
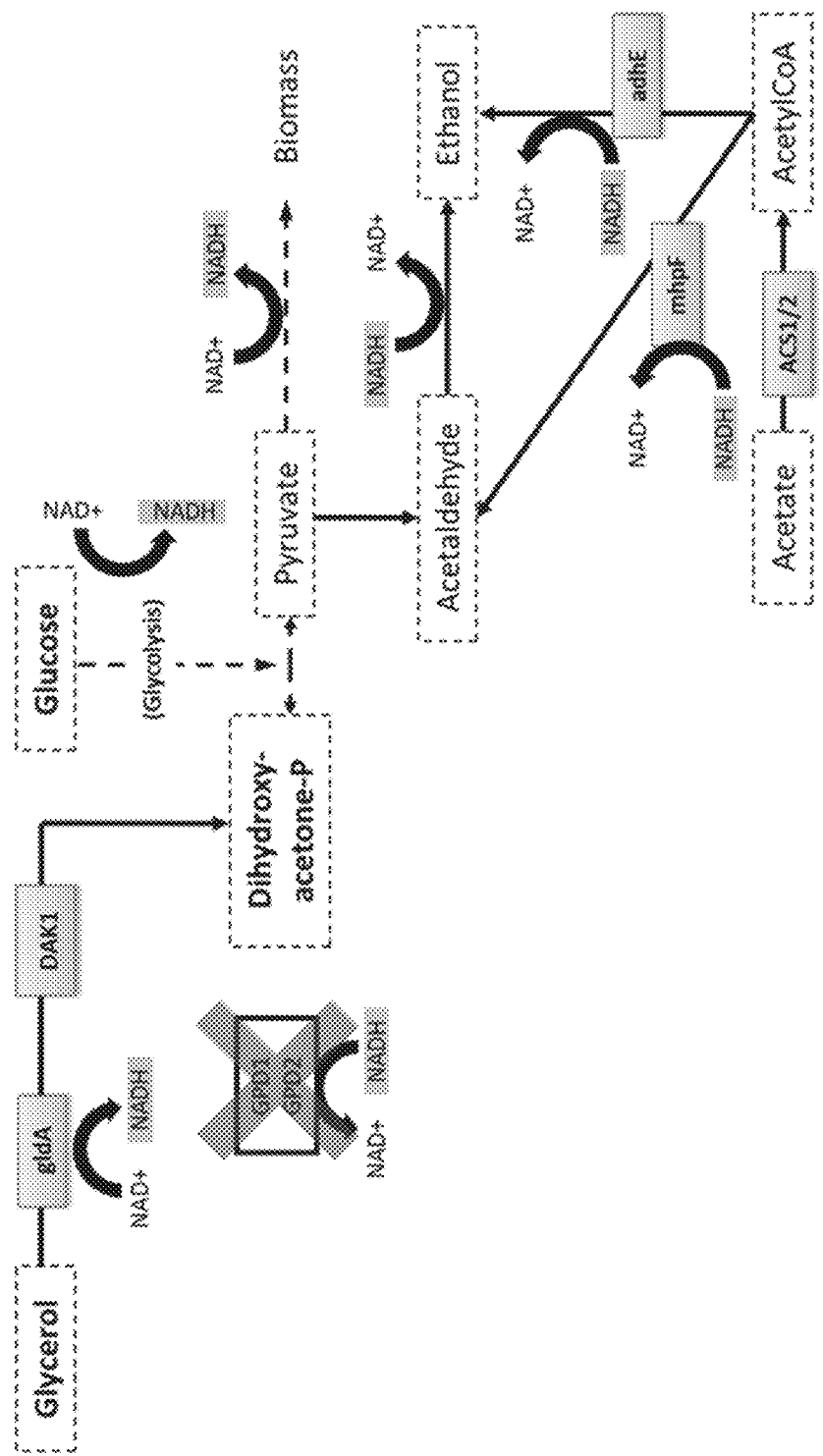
FIG. 1. Schematic representation of the enzymatic reactions involved in the conversion of glycerol and acetic acid (acetate) into ethanol. Acetate is first converted into acetyl-CoA through the yeast enzyme Acs (Acs1 and/or Acs2, encoded by the genes ACS1 and ACS2 respectively). Acetyl-CoA is then converted into acetaldehyde through the mhpF gene, or directly into ethanol through the bifunctional adhE enzyme from *E. coli* (or similar enzymes catalyzing the same conversion). Upon introduction of the glycerol consumption pathway, converting externally added glycerol, an extra flow of NADH is generated. Deletion of the GPD1 and GPD2 genes is optional in order to avoid the intracellular production of glycerol and the utilization of NADH by these enzymes.
Figure 2:
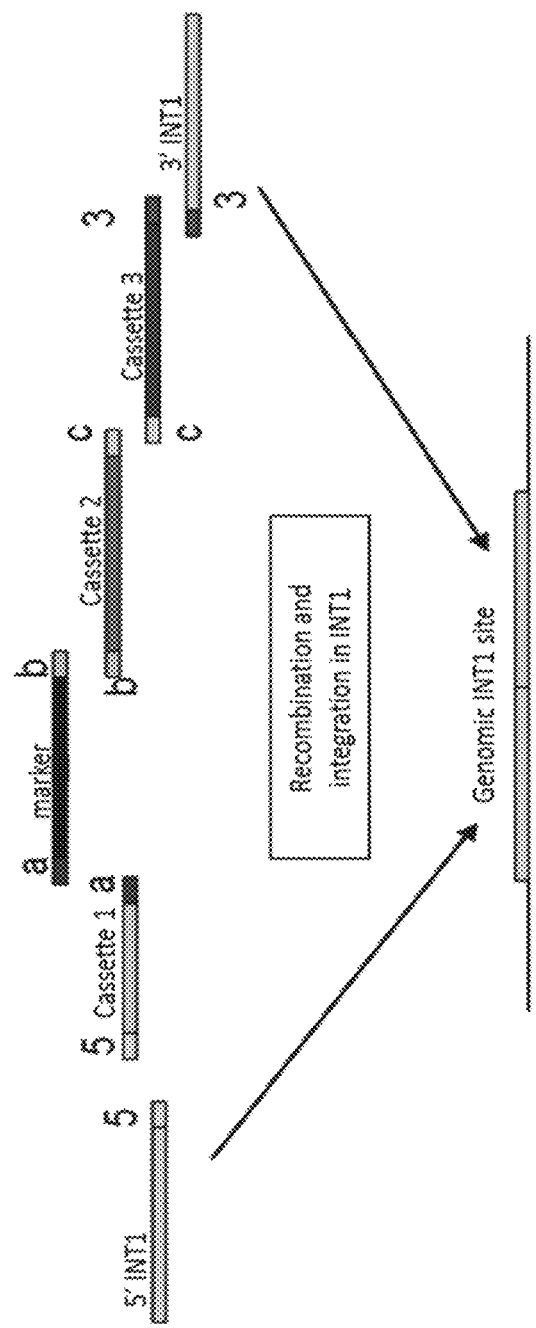

FIG. 2. Schematic display of the strain construction approach. INT (integration) flanks and expression cassettes (CAS), including selectable marker, are amplified using PCR and transferred into yeast. Recombination will take place between the connectors (designated 5, a, b, c and 3 respectively in FIG. 1) resulting in the integration of the pathway in the desired location in the yeast genome (in this case, INT1). The number of genes of interest may be extended, as described in the examples. Unique connectors were used to facilitate recombination of the separate expression cassettes and integration into the genome of the recipient cell.

Figure 3:
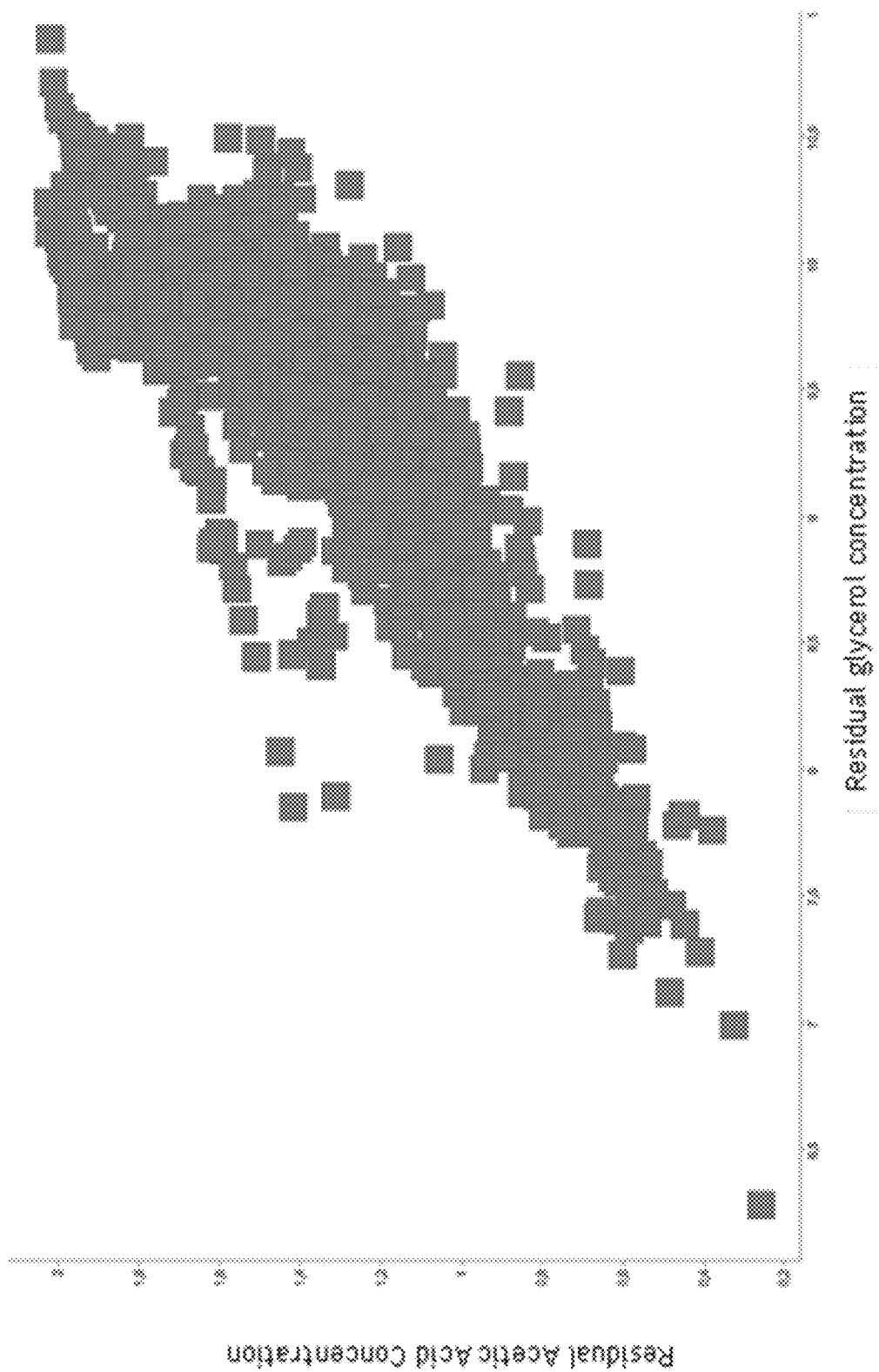

FIG. 3. Results of screening. The residual acetic acid concentration is plotted as function of the residual acetate concentration.

Figure 4:
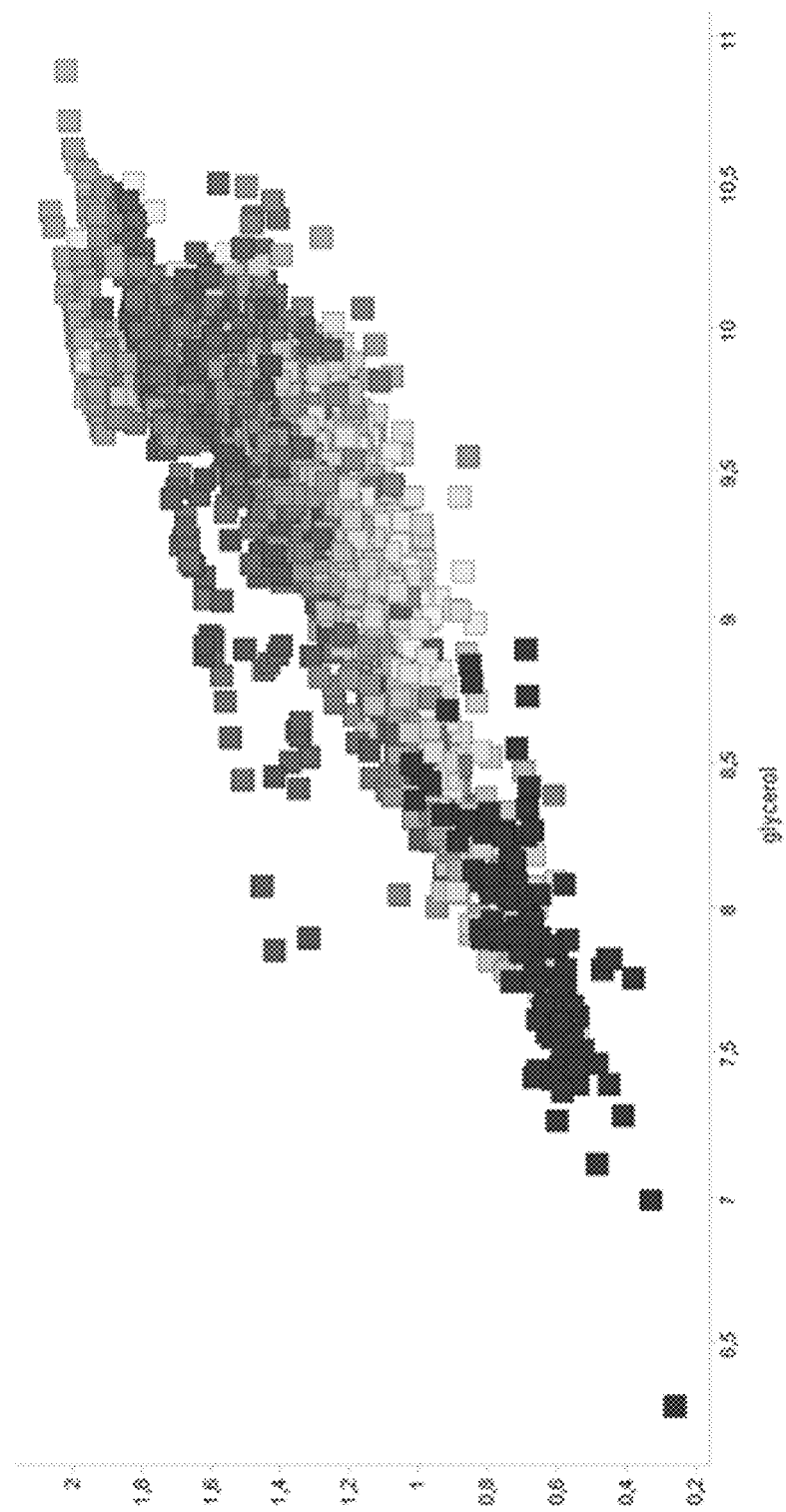

FIG. 4. The residual acetic acid concentration is plotted as function of the residual acetate concentration. The 150 best performing strains, based on the residual acetate and glycerol concentrations as well as ethanol production from glycerol and acetate, are displayed in dark grey.

Figure 5:
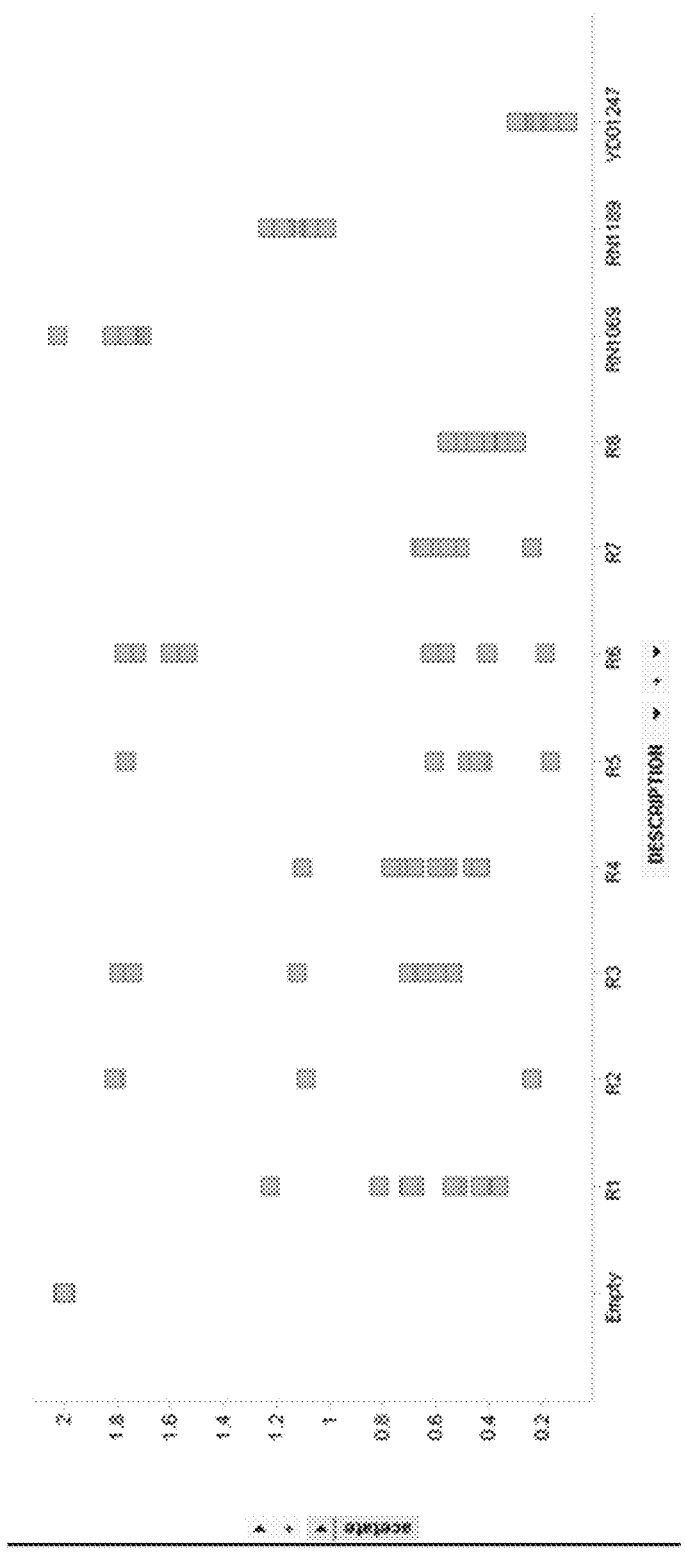
Figure 5:
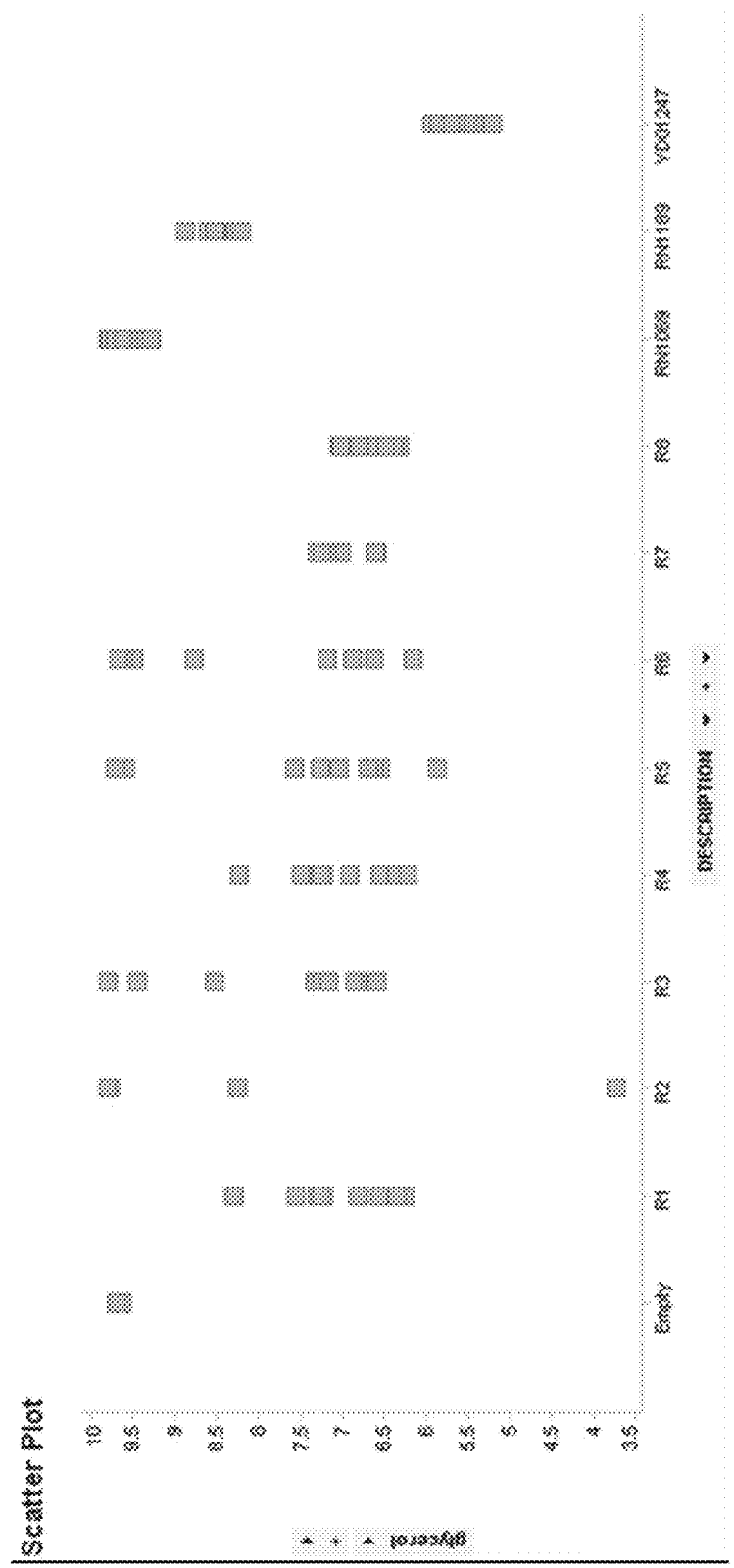

FIG. 5. Rescreening results of newly generated transformants (R1-R8) and reference strains (RN1069, RN1189 and YD01247). Eight independent transformants were picked per transformation. Likewise, reference strains were inoculated in eightfold.

In the upper panel, the residual acetic acid (acetate) concentration is depicted after 72 hours of incubation. In the lower panel, the residual glycerol concentration is plotted.

Figure 6:
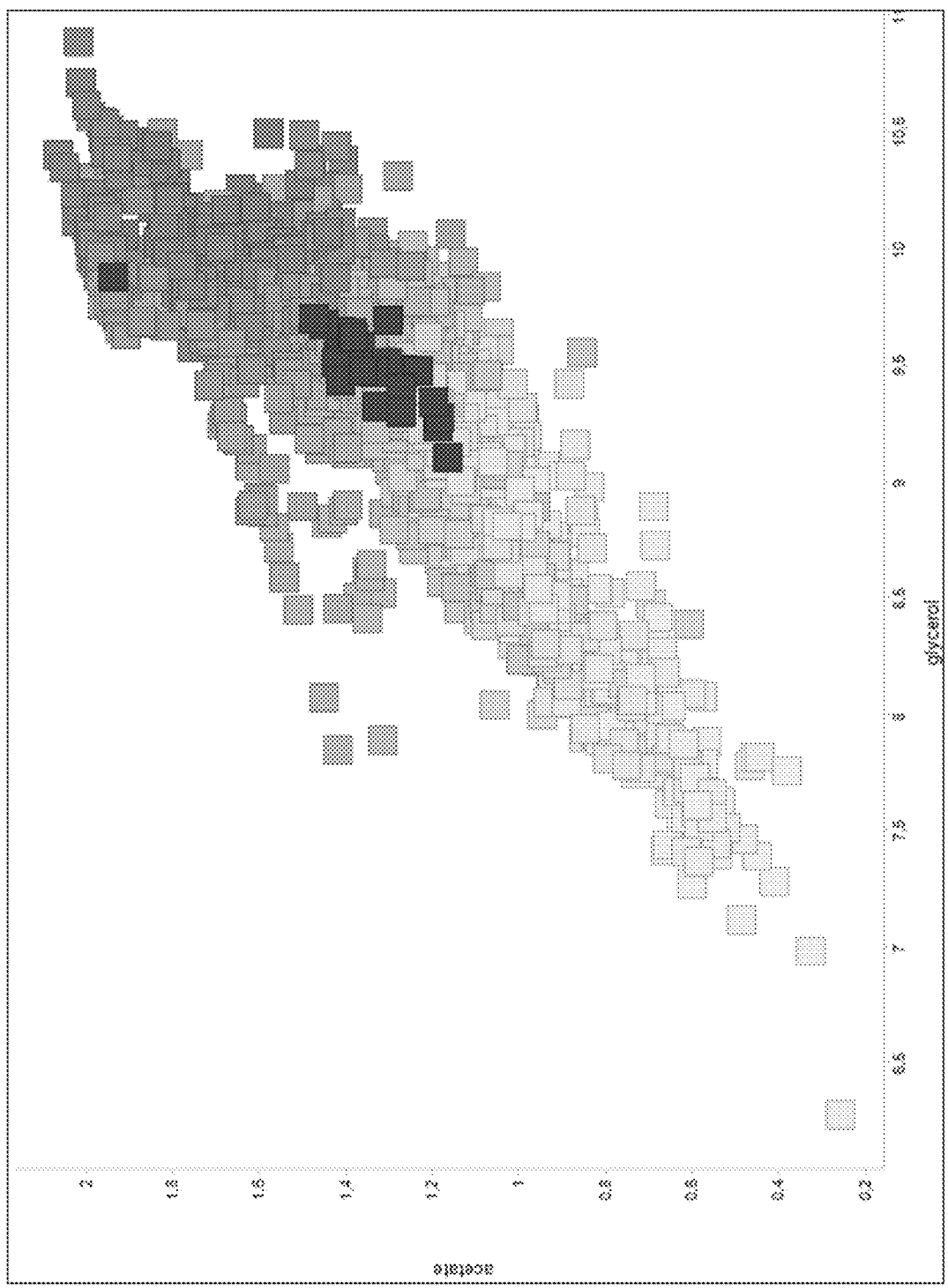

FIG. 6. Results of the screening. In total, 2592 strains were screened, including reference strain RN1189. Reference strain RN1189 was included 27 times. The performance of reference strain RN1189 relative to the other strains (total 2592) is depicted in the figure below. The strains are ranked as described before, where the better performing strains are indicated by a lighter color (and are closer to the bottom-left corner of the graph). The less well performing strains are indicated by a darker color, the change in color is gradual. The exception is that the reference strain, RN1189, is indicated in the darkest color.

Figure 7:
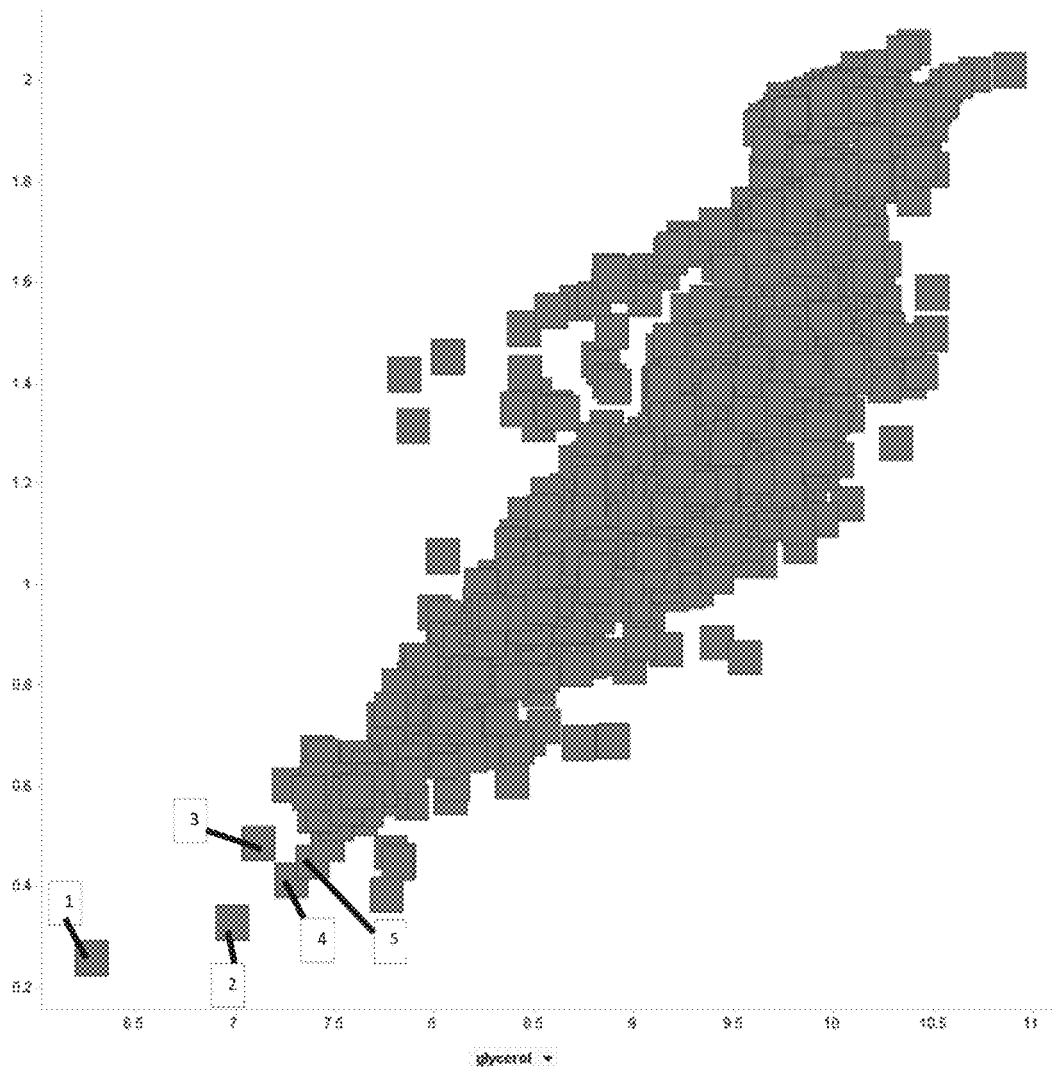

FIG. 7. Results of the screening. The top five of best performing strains are shown here: 1) represents YD01247, 2) is YD01248, 3) is YD01249, 4) is YD01250.Strain 5 was not named nor tested further.

BRIEF DESCRIPTION OF THE SEQUENCE LISTING

SEQ ID NO: 1 adhE *Escherichia coli* Bifunctional acetaldehyde-CoA/alcohol dehydrogenase (protein);
SEQ ID NO: 2 acdH *Lactobacillus plantarum* Acetaldehyde dehydrogenase (protein):
SEQ ID NO: 3 eutE *Escherichia coli* Ethanolamine utilization protein (protein);
SEQ ID NO: 4 Lin1129 *Listeia innocua* Aldehyde dehydrogenase (protein);
SEQ ID NO: 5 adhE *Staphylococcus aureus* Bifunctional acetaldehyde-CoA/alcohol dehydrogenase (protein);
SEQ ID NO: 6 ACS2 *Saccharomyces cerevisiae* Acetyl-CoA ligase (protein);
SEQ ID NO: 7 gldA *Escherichia coli* Glycerol dehydrogenase (protein);
SEQ ID NO: 8 gldA *Klebsiella pneumoniae* Glycerol dehytogenase (protein);
SEQ ID NO: 9 gldA *Enterococcus aerogenes* Glycerol dehyrogenase (protein);
SEQ ID NO: 10 gldA *Yersinia aldovae* Glycerol dehydrogenase (protein);
SEQ ID NO: 11 DAK1 *Saccharomyces cerevisiae* Dihydroxyacetone kinase (protein);
SEQ ID NO: 12 dhaK *Klebsiella pneumoniae* Dihyrkoxyacetone kinase (protein);
SEQ ID NO: 13 DAK1 *Yarrowia lipolytica* Dihydroxyacetone kinase (protein);
SEQ ID NO: 14 DAK1 *Schizosaccharomyces pombe* Dihyroxyacetone kinase (protein);
SEQ ID NO: 15 Fragment containing the TDH3-promoter;
SEQ ID NO: 16 Fragment containing the TDH1-promoter;
SEQ ID NO: 17 Fragment containing the PGK1-terminator
SEQ ID NO: 18 Fragment containing the PGK1-promoter,
SEQ ID NO: 19 Fragment containing the PRE3-promoter
SEQ ID NO: 20 Fragment containing the PGI1-terminator;
SEQ ID NO: 21 Fragment containing the ENO1-promoter,
SEQ ID NO: 22 Fragment containing the ACT1-promoter;
SEQ ID NO: 23 Fragment containing the CYC1-terminator
SEQ ID NO: 24 Fragment containing the TPI1-promoter;
SEQ ID NO: 25 Fragment containing the ATG7-promoter;
SEQ ID NO: 26 Fragment containing the ENO1-terminator
SEQ ID NO: 27 Sequence of the kanMX marker and flanking regions;
SEQ ID NO: 28 Sequence of gene disruption cassette GPD1::hphMX;
SEQ ID NO: 29 Sequence of gene disruption cassette GPD2::natMX;
SEQ ID NO: 30 Forward primer 5' INT1 fragment (INT5-f);
SEQ ID NO: 31 Reverse primer 5' INT1 fragment (INT5-r);
SEQ ID NO: 32 Forward primer expression cassette 1 (con5-f):

SEQ ID NO: 33 Reverse primer expression cassette 1 (conA-r);
SEQ ID NO: 34 Forward primer marker (conA-f);
SEQ ID NO: 35 Reverse primer marker (conB-r);
SEQ ID NO: 36 Forward primer expression cassette 2 (conB-f);
SEQ ID NO: 37 Reverse primer expression cassette 2 (conC-r):
SEQ ID NO: 38 Forward primer expression cassette 3 (conC-f);
SEQ ID NO: 39 Reverse primer expression cassette 3 (conD-r);
SEQ ID NO: 40 Forward primer expression cassette 4 (conD-f);
SEQ ID NO: 41 Reverse primer expression cassette 4 (con3-r);
SEQ ID NO: 42 Forward primer 3' INT1 fragment (INT3-f);
SEQ ID NO: 43 Reverse primer 3' INT1 fragment (INT3-r);
SEQ ID NO: 44 Sequence of plasmid p5Abbn;
SEQ ID NO: 45 Sequence of plasmid pBCbbn:
SEQ ID NO: 46 Sequence of plasmid pCDbbn;
SEQ ID NO: 47 Sequence of plasmid pD3bbn
SEQ ID NO: 48 Sequence containing the adhE (*E. coli*) DNA sequence codon-pair optimized for expression in *S. cerevisiae;*
SEQ ID NO: 49 Sequence containing the acdH (*L. plantarum*) DNA sequence codon-pair optimized for expression in *S. cerevisiae;*
SEQ ID NO: 50 Sequence containing the eutE (*E. coli*) DNA sequence codon-pair optimized for expression in *S. cerevisiae;*
SEQ ID NO: 51 Sequence containing the Lin1129 (*Linnocua*) DNA sequence codon-pair optimized for expression in *S. cerevisiae;*
SEQ ID NO: 52 Sequence containing the adhE (*S. aureus*) DNA sequence codon-pair optimized for expression in *S. cerevisiae;*
SEQ ID NO: 53 Sequence containing the ACS2 (*S. cerevisiae*) DNA sequence codon-pair optimized for expression in *S. cerevisiae;*
SEQ ID NO: 54 Sequence containing the gldA (*E. coli*) DNA sequence codon-pair optimized for expression in *S. cerevisiae;*
SEQ ID NO: 55 Sequence containing the gldA (*K. pneumoniae*) DNA sequence codon-pair optimized for expression in *S. cerevisiae;*
SEQ ID NO: 56 Sequence containing the gldA (*E. aerogenes*) DNA sequence codon-pair optimized for expression in *S. cerevisiae;*
SEQ ID NO: 57 Sequence containing the gldA (*Y. aldovae*) DNA sequence codon-pair optimized for expression in *S. cerevisiae;*
SEQ ID NO: 58 Sequence containing the DAK1 (*S. cerevisiae*) DNA sequence codon-pair optimized for expression in *S. cerevisiae;*
SEQ ID NO: 59 Sequence containing the dhaK (*K. pneumoniae*) DNA sequence codon-pair optimized for expression in *S. cerevisiae;*
SEQ ID NO: 60 Sequence containing the DAK1 (*Y. lipolytica*) DNA sequence codon-pair optimized for expression in *S. cerevisiae;*
SEQ ID NO: 61 Sequence containing the DAK1 (*S. pombe*) DNA sequence codon-pair optimized for expression in *S. cerevisiae;*

DETAILED DESCRIPTION OF A PREFERRED EMBODIMENT

*Saccharomyces cerevisiae* produces ethanol from sugars, such as glucose, under anaerobic conditions. This process is redox-neutral. When yeast is growing however, a surplus of NADH is generated. In order to restore the redox balance, yeast will produce glycerol. During this process, NADH is converted into NAD+ again. The ethanol industry considers glycerol an undesired by-product. Omission of glycerol formation under anaerobic conditions is a long felt desire from the ethanol industry. As described above, several attempts have been made by several different groups to redirect the carbon flux from glycerol formation towards ethanol, thereby increasing the ethanol yield.

The most direct measure to prevent glycerol formation would be deleting genes encoding proteins involved in the biosynthesis of glycerol. However, when the GPD1 and GPD2 genes are disrupted, the yeast is unable to grow under anaerobic conditions, as it is unable to restore its redox balance. Medina et al (2009) demonstrated that upon introduction of a NADH-dependent acetyl-CoA dehydrogenase gene (such as the *E. coli* mhpF-gene, as described by Medina et al). the ability of a gpd1 gpd2 double deletion strain to grow under anaerobic conditions is recovered, provided that acetic acid is supplied into the fermentation medium. The acetic acid is converted into acetyl-CoA through the ACS1/ACS2 gene products. Acetyl-CoA is converted into acetaldehyde, and subsequently into ethanol through the mhpF and ADH1 gene products (Medina et al, 2009). In this way, formation of an unwanted by-product (glycerol) is eliminated, resulting in a higher ethanol yield.

As acetic acid is often considered to be the most toxic compound present in hydrolysates, especially in hydrolysates with a pH close to or below the pKa of acetic acid (pKa HAc~4.76), there is a desire to further decrease the acetate (acetic acid) concentration in hydrolysates. One way of increasing the anaerobic acetate conversion potential of the yeast is by introducing a glycerol conversion pathway. By introduction of a glycerol pathway that converts externally added glycerol, as the gpd1 gpd2 cell does not produce glycerol itself, even more NADH is generated, forcing the yeast cell to convert more acetic acid in order to maintain the redox balance (see FIG. 1 and WO2013/081456).

Glycerol is available in sufficiently large quantities at biorefineries. To this end, the genes gldA from *E. coli* and DAK1 from *S. cerevisiae* were overexpressed, in order to allow for a further increase in the conversion of the toxic acetic acid into ethanol (WO 2013/081456). Indeed, higher ethanol yields were obtained.

In order to even further improve the anaerobic (co-) conversion of glycerol and acetic acid both in terms of rate and amount, alternative gene combinations were tested. For a number of enzymes in the pathway, i.e. glycerol dehydrogenase, dihydroxyacetone kinase and acetaldehyde dehydrogenase, multiple alternative genes were tested that could further enhance the ability of the yeast strain to convert glycerol and acetic acid, next to pentose and hexose sugars, into ethanol under anaerobic conditions.

The invention therefore provides yeast cell that is genetically modified comprising:

a) one or more nucleotide sequence encoding a NAD+-dependent acetylating acetaldehyde dehydrogenase (E.C. 1.2.1.10);

b) one or more nucleotide sequence encoding a acetyl-CoA synthetase (E.C. 6.2.1.1);

c) one or more nucleotide sequence encoding a glycerol dehydrogenase (E.C. 1.1.1.6); and d) one or more nucleotide sequence encoding a dihydroxyacetone kinase (E.C. 2.7.1.28 or E.C. 2.7.1.29).

Embodiments of the invention are described below. The following items describe several embodiments of the invention, wherein amongst others the features a) to d) here above are detailed:

Item 1:
Cell that is genetically modified comprising:
- a) one or more nucleotide sequence encoding a NAD+-dependent acetylating acetaldehyde dehydrogenase (E.C. 1.2.1.10);
- b) one or more nucleotide sequence encoding a acetyl-CoA synthetase (E.C. 6.2.1.1);
- c) one or more nucleotide sequence encoding a glycerol dehydrogenase (E.C. 1.1.1.6); and
- d) one or more nucleotide sequence encoding a dihydroxyacetone kinase (E.C. 2.7.1.28 or E.C. 2.7.1.29).

Item 1a:
Cell that is genetically modified comprising:
- a) one or more nucleotide sequence encoding a heterologous NAD+-dependent acetylating acetaldehyde dehydrogenase (E.C. 1.2.1.10);
- b) one or more nucleotide sequence encoding a homologous or heterologous acetyl-CoA synthetase (E.C. 6.2.1.1);
- c) one or more nucleotide sequence encoding a heterologous glycerol dehydrogenase (E.C. 1.1.1.6); and
- d) one or more nucleotide sequence encoding a homologous or heterologous dihydroxyacetone kinase (E.C. 2.7.1.28 or E.C. 2.7.1.29).

Item 2.
Cell according to item 1, comprising a deletion or disruption of one or more endogenous nucleotide sequence encoding a glycerol 3-phosphate phosphohydrolase (GPP1,GPP2) and/or encoding a glycerol 3-phosphate dehydrogenase gene (GPD1, GPD2);

Item 3.
Cell according to item 1 or item 2, wherein
- b) is one or more heterologous nucleotide sequence encoding a homologous or heterologous acetyl-CoA synthetase (E.C. 6.2.1.1) represented by SEQ ID NO: 6 or a functional homologue of SEQ ID NO: 6 having sequence identity of at least 60% with SEQ ID NO: 6;

Item 4. Cell according to item 3, wherein
- c) is one or more nucleotide sequence encoding a heterologous glycerol dehydrogenase (E.C. 1.1.1.6) represented by SEQ ID NO: 7 or a functional homologue of SEQ ID NO: 7 having sequence identity of at least 60% with SEQ ID NO: 7; and/or
  one or more nucleotide sequence encoding a heterologous glycerol dehydrogenase (E.C. 1.1.1.6) represented by SEQ ID NO: 9 or a functional homologue of SEQ ID NO: 9 having sequence identity of at least 60% with SEQ ID NO: 9

Item 5. Cell according to item 4, wherein
- c) is one or more nucleotide sequence encoding a heterologous glycerol dehydrogenase (E.C. 1.1.1.6) represented by SEQ ID NO: 7 or a functional homologue of SEQ ID NO: 7 having sequence identity of at least 60% with SEQ ID NO: 7.

Item 6. Cell according to any of items 1 to 5, wherein
- d) is one or more nucleotide sequence encoding a homologous or heterologous dihydroxyacetone kinase (E.C. 2.7.1.28 or E.C. 2.7.1.29) represented by SEQ ID NO: 11 or a functional homologue of SEQ ID NO: 11 having sequence identity of at least 60% with SEQ ID NO: 11 and/or
  one or more nucleotide sequence encoding a homologous or heterologous dihydroxyacetone kinase (E.C. 2.7.1.28 or E.C. 2.7.1.29) represented by SEQ ID NO: 13 or a functional homologue of SEQ ID NO: 13 having sequence identity of at least 60% with SEQ ID NO: 13.

Item 7. Cell according to item 6, wherein
- d) is one or more nucleotide sequence encoding a homologous or heterologous dihydroxyacetone kinase (E.C. 2.7.1.28 or E.C. 2.7.1.29) represented by SEQ ID NO: 13 or a functional homologue of SEQ ID NO: 13 having sequence identity of at least 60% with SEQ ID NO: 13.

Item 8. Cell according to any of items 1 to 7 wherein
- a) is one or more nucleotide sequence encoding a heterologous NAD+-dependent acetylating acetaldehyde dehydrogenase represented by SEQ ID NO: 1 or a functional homologue of SEQ ID NO: 1 having sequence identity of at least 60% with SEQ ID NO: 1; and/or
  one or more nucleotide sequence encoding a heterologous NAD+-dependent acetylating acetaldehyde dehydrogenase represented by SEQ ID NO: 2 or a functional homologue of SEQ ID NO: 2 having sequence identity of at least 60% with SEQ ID NO: 2 and/or
  one or more nucleotide sequence encoding a heterologous NAD+-dependent acetylating acetaldehyde dehydrogenase represented by SEQ ID NO: 3 or a functional homologue of SEQ ID NO: 3 having sequence identity of at least 60% with SEQ ID NO: 3.

Item 9. Cell according to item 8 wherein
- a) is one or more nucleotide sequence encoding a heterologous NAD+-dependent acetylating acetaldehyde dehydrogenase (E.C. 1.2.1.10) represented by SEQ ID NO: 1 or a functional homologue of SEQ ID NO: 1 having sequence identity of at least 60% with SEQ ID NO: 1; and/or
  one or more nucleotide sequence encoding a heterologous NAD+-dependent acetylating acetaldehyde dehydrogenase (E.C. 1.2.1.10) represented by SEQ ID NO: 2 or a functional homologue of SEQ ID NO: 2 having sequence identity of at least 60% with SEQ ID NO: 2

Item 10. Cell according to item 9 wherein
- a) is one or more nucleotide sequence encoding a heterologous NAD+-dependent acetylating acetaldehyde dehydrogenase represented by SEQ ID NO: 2 or a functional homologue of SEQ ID NO: 2 having sequence identity of at least 60% with SEQ ID NO: 2.

Item 11. Cell according to any of item 1 to 10 wherein
- a) is one or more nucleotide sequence encoding a heterologous NAD+-dependent acetylating acetaldehyde dehydrogenase (E.C. 1.2.1.10) represented by SEQ ID NO: 3 or a functional homologue of SEQ ID NO: 3 having sequence identity of at least 60% with SEQ ID NO: 3;
- b) is one or more nucleotide sequence encoding a homologous or heterologous acetyl-CoA synthetase (E.C. 6.2.1.1) represented by SEQ ID NO: 6 or a functional homologue of SEQ ID NO: 6 having sequence identity of at least 60% with SEQ ID NO: 6;
- c) is one or more nucleotide sequence encoding a heterologous glycerol dehydrogenase (E.C. 1.1.1.6) represented by SEQ ID NO: 7 or a functional homologue of SEQ ID NO: 7 having sequence identity of at least 60% with SEQ ID NO: 7; and d) is one or more nucleotide sequence encoding a homologous or heterologous dihydroxyacetone kinase (E.C. 2.7.1.28 or E.C. 2.7.1.29) represented by SEQ ID NO: 11 or a functional homologue of SEQ ID NO: 11 having sequence identity of at least 60% with SEQ ID NO: 11.

Item 12. Cell according to any of item 1 to 10, wherein
a) is one or more nucleotide sequence encoding a heterologous NAD+-dependent acetylating acetaldehyde dehydrogenase (E.C. 1.2.1.10) represented by SEQ ID NO: 2 or a functional homologue of SEQ ID NO: 2 having sequence identity of at least 60% with SEQ ID NO: 2;
b) is one or more nucleotide sequence encoding a homologous or heterologous acetyl-CoA synthetase (E.C. 6.2.1.1) represented by SEQ ID NO: 6 or a functional homologue of SEQ ID NO: 6 having sequence identity of at least 60% with SEQ ID NO: 6;
c) is one or more nucleotide sequence encoding a heterologous glycerol 3-phosphate dehydrogenase (E.C. 1.1.1.8) represented by SEQ ID NO: 9 or a functional homologue of SEQ ID NO: 9 having sequence identity of at least 60% with SEQ ID NO: 9; and
d) is one or more nucleotide sequence encoding a homologous or heterologous dihydroxyacetone kinase (E.C. 2.7.1.28 or E.C. 2.7.1.29) represented by SEQ ID NO: 11 or a functional homologue of SEQ ID NO: 11 having sequence identity of at least 60% with SEQ ID NO: 11.

Item 13. Cell according to any of item 1 to 10, wherein
a) is one or more nucleotide sequence encoding a heterologous NAD+-dependent acetylating acetaldehyde dehydrogenase (E.C. 1.2.1.10) represented by SEQ ID NO: 2 or a functional homologue of SEQ ID NO: 2 having sequence identity of at least 60% with SEQ ID NO: 2;
b) is one or more nucleotide sequence encoding a homologous or heterologous acetyl-CoA synthetase (E.C. 6.2.1.1) represented by SEQ ID NO: 6 or a functional homologue of SEQ ID NO: 6 having sequence identity of at least 60% with SEQ ID NO: 6;
c) is one or more nucleotide sequence encoding a heterologous glycerol 3-phosphate dehydrogenase (E.C. 1.1.1.8) represented by SEQ ID NO: 7 or a functional homologue of SEQ ID NO: 7 having sequence identity of at least 60% with SEQ ID NO: 7; and
d) is one or more nucleotide sequence encoding a homologous or heterologous dihydroxyacetone kinase (E.C. 2.7.1.28 or E.C. 2.7.1.29) represented by SEQ ID NO: 13 or a functional homologue of SEQ ID NO: 13 having sequence identity of at least 60% with SEQ ID NO: 13.

Item 14. Cell according to any of item 1 to 10, wherein
a) is one or more nucleotide sequence encoding a heterologous NAD+-dependent acetylating acetaldehyde dehydrogenase (E.C. 1.2.1.10) represented by SEQ ID NO: 1 or a functional homologue of SEQ ID NO: 1 having sequence identity of at least 60% with SEQ ID NO: 1;
b) is one or more nucleotide sequence encoding a homologous or heterologous acetyl-CoA synthetase (E.C. 6.2.1.1) represented by SEQ ID NO: 6 or a functional homologue of SEQ ID NO: 6 having sequence identity of at least 60% with SEQ ID NO: 6;
c) is one or more nucleotide sequence encoding a heterologous glycerol 3-phosphate dehydrogenase (E.C. 1.1.1.8) represented by SEQ ID NO: 7 or a functional homologue of SEQ ID NO: 7 having sequence identity of at least 60% with SEQ ID NO: 7; and
d) is one or more nucleotide sequence encoding a homologous or heterologous dihydroxyacetone kinase (E.C. 2.7.1.28 or E.C. 2.7.1.29) represented by SEQ ID NO: 13 or a functional homologue of SEQ ID NO: 13 having sequence identity of at least 60% with SEQ ID NO: 13.

The cell according to the invention may be prepared by modification of a host cell, e.g. introduction of polynucleotides and/or expression of proteins, e.g. nucleotides corresponding to the above features a) to d).

The polynucleotides or proteins may be homologous or heterologous to the genome of the host cell. The term "heterologous", with respect to the host cell, means that the polynucleotide does not naturally occur in the genome of the host cell or that the polypeptide is not naturally produced by that cell. "Homologous" with respect to a host cell, means that the polynucleotide does naturally occur in the genome of the host cell or that the polypeptide is naturally produced by that cell. Homologous protein expression may e.g. be an overexpression or expression of under the control a different promoter. Heterologous protein expression involves expression of a protein that is not naturally produced in the host cell.

The cell according to the invention is illustrated in FIG. 1. FIG. 1 gives a schematic representation of the enzymatic reactions involved in the conversion of glycerol and acetic acid (acetate) into ethanol. Acetate is first converted into acetyl-CoA through the yeast enzyme Acs (Acs1 and/or Acs2, encoded by the genes ACS1 and ACS2 respectively). Acetyl-CoA is then converted into acetaldehyde through the mhpF gene, or directly into ethanol through the bifunctional adhE enzyme from *E. coli* (or similar enzymes catalyzing the same conversion). Upon introduction of the glycerol consumption pathway, converting externally added glycerol, an extra flow of NADH is generated. As indicated in FIG. 1, and in item 2 GPD1 and GPD2 genes may be deleted to avoid the intracellular production of glycerol and the utilization of NADH by these enzymes.

The ethanol yield per consumed sugar (glucose or other sugars) increases due to elimination of glycerol production, ethanol generation from acetate/acetic acid in the medium (and always present in lignocellulosic hydrolysates) and glycerol externally added to the medium (or hydrolysate).

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element.

"function" polypeptide", is also designated herein as "polypeptide "function"" or "polypeptide". "function polypeptide polynucleotide", is herein a polynucleotide that encodes the ""function" polypeptide. The invention further relates to a polynucleotide encoding such polypeptide, a nucleic acid construct comprising the polynucleotide encoding the polypeptide and to a vector for the functional expression of a heterologous polypeptide in a (yeast) cell, said expression vector comprising a heterologous nucleic acid sequence operably linked to a promoter functional in the cell and said heterologous nucleic acid sequence encoding a polypeptide having the "function" enzymatic activity in (the cytosol of) said cell. A "function" polypeptide herein may have one or more alternative and/or additional activities other than that of the "function" activity.

The E.C. codes mentioned herein are used only for clarification of a "function", but should in no way be considered to be limiting to the "function".

Any exogenous gene coding for an enzyme herein comprises a nucleotide sequence coding for an amino acid sequence with at least 50, 60, 65, 70, 75, 80, 85, 86, 87, 88, 89, 90, 91, 92, 93, 94, 95, 96, 97, 98, 99 or 100% amino acid sequence identity with any of SEQ ID's NO: X, wherein SEQ ID NO:X is any of the protein sequences in the sequence listing of this application. In particular for all of SEQ ID NO:'s 1-14. The exogenous gene coding for an enzyme may also comprises a nucleotide sequence coding for an amino acid sequence having one or several substitutions, insertions and/or deletions as compared to the amino acid sequence of any of SEQ ID NO: X. In particular for all of SEQ ID NO:'s 1-14. Preferably the amino acid sequence has no more than 420, 380, 300, 250, 200, 150, 100, 75, 50, 40, 30, 20, 10, 9, 8, 7, 6, 5, 4, 3, 2, or 1 amino acid substitutions, insertions and/or deletions as compared to SEQ ID's NO: X. In particular for all of SEQ ID NO:'s 1-14.

Any exogenous gene coding for an enzyme herein comprises a nucleotide sequence with at least 40, 50, 60, 65, 70, 75, 80, 85, 86, 87, 88, 89, 90, 95, 96, 97, 98, 99% or 100% nucleotide (DNA) sequence identity with any of SEQ ID's NO: Y, wherein SEQ ID NO: Y is any of the nucleotide (DNA) sequences in the sequence listing of this application. In particular for all of SEQ ID NO:'s 48-61.

The features a) to d) of item 1 will now be described in more detail below.

Feature a) one or more nucleotide sequence encoding a NAD+-dependent acetylating acetaldehyde dehydrogenase:

The cell of the invention comprises an exogenous gene coding for an enzyme with the ability to reduce acetylCoA into acetaldehyde, which gene confers to the cell the ability to convert acetylCoA (and/or acetic acid) into ethanol. An enzyme with the ability to reduce acetylCoA into acetaldehyde is herein understood as a bifunctional enzyme which catalyzes the following reactions (adhE):

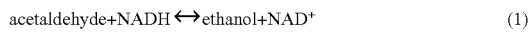
acetaldehyde+NADH ↔ ethanol+NAD⁺        (1)

and/or

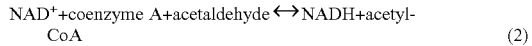
NAD⁺+coenzyme A+acetaldehyde ↔ NADH+acetyl-CoA        (2)

Thus, the enzyme catalyzes the conversion of acetaldehyde into ethanol (and vice versa) and is also referred to as an acetaldehyde dehydrogenase (NAD+-dependent). The enzyme is a bifunctional enzyme which further catalyzes the conversion of coenzyme A and acetaldehyde into acetyl-coA (and vice versa) also designated as acetaldehyde dehydrogenase. This enzyme allows the re-oxidation of NADH when acetyl-Coenzyme A is generated from acetate present in the growth medium, and thereby glycerol synthesis is no longer needed for redox cofactor balancing. The nucleic acid sequence encoding the NADH-dependent acetylating acetaldehyde dehydrogenase (E.C. 1.2.1.10) may in principle originate from any organism comprising a nucleic acid sequence encoding said dehydrogenase.

Known NAD+-dependent acetylating acetaldehyde dehydrogenases that can catalyse the NADH-dependent reduction of acetyl-Coenzyme A to acetaldehyde may in general be divided in three types of NADH-dependent acetylating acetaldehyde dehydrogenase functional homologues:

1) Bifunctional proteins that catalyse the reversible conversion of acetyl-Coenzyme A to acetaldehyde, and the subsequent reversible conversion of acetaldehyde to ethanol. An example of this type of proteins is the AdhE protein in E. coli (Gen Bank No: NP-415757). AdhE appears to be the evolutionary product of gene fusion. The NH2-terminal region of the AdhE protein is highly homologous to aldehyde: NADH oxidoreductases, whereas the COOH-terminal region is homologous to a family of Fe2+-dependent ethanol:NADH oxidoreductases (Membrillo-Hemandez et al., (2000) J. Biol. Chem. 275: 33869-33875). The E. coli AdhE is subject to metal-catalyzed oxidation and therefore oxygen-sensitive (Tamarit et al. (1998) J. Biol. Chem. 273: 3027-32).

2) Proteins that catalyse the reversible conversion of acetyl-Coenzyme A to acetaldehyde in strictly or facultative anaerobic micro-organisms but do not possess alcohol dehydrogenase activity. An example of this type of proteins has been reported in Clostridium kluyveri (Smith et al. (1980) Arch. Biochem. Biophys. 203: 663-675). An acetylating acetaldehyde dehydrogenase has been annotated in the genome of Clostridium kluyveri DSM 555 (GenBank No: EDK33116). A homologous protein AcdH is identified in the genome of Lactobacillus plantarum (GenBank No: NP-784141). Another example of this type of proteins is the said gene product in Clostridium beijerinckii NRRL B593 (Toth et al. (1999) Appl. Environ. Microbiol. 65: 4973-4980, GenBank No: AAD31841).

3) Proteins that are part of a bifunctional aldolase-dehydrogenase complex involved in 4-hydroxy-2-ketovalerate catabolism. Such bifunctional enzymes catalyze the final two steps of the meta-cleavage pathway for catechol, an intermediate in many bacterial species in the degradation of phenols, toluates, naphthalene, biphenyls and other aromatic compounds (Powlowski and Shingler (1994) Biodegradation 5, 219-236). 4-Hydroxy-2-ketovalerates first converted by 4-hydroxy-2-ketovalerate aldolase to pyruvate and acetaldehyde, subsequently acetaldehyde is converted by acetylating acetaldehyde dehydrogenase to acetyl-CoA. An example of this type of acetylating acetaldehyde dehydrogenase is the DmpF protein in Pseudomonas sp CF600 (GenBank No: CAA43226) (Shingler et al. (1992) J. Bacteriol. 174:71 1-24). The E. coli MphF protein (Ferrandez et al. (1997) J. Bacteriol. 179: 2573-2581, GenBank No: NP-414885) is homologous to the DmpF protein in Pseudomonas sp. CF600.

A suitable nucleic acid sequence may in particular be found in an organism selected from the group of Escherichia, in particular E. coli; Mycobacterium, in particular Mycobacterium marinum, Mycobacterium ulcerans, Mycobacterium tuberculosis; Carboxydothermus, in particular Carboxydothermus hydrogenoformans; Entamoeba, in particular Entamoeba histolytica; Shigella, in particular Shigella sonnei; Burkholderia, in particular Burkholderia pseudomallei, Klebsiella, in particular Klebsiella pneumoniae; Azotobacter, in particular Azotobacter uinelandii; Azoarcus sp; Cupriauidus, in particular Cupriauidus taiwanensis; Pseudomonas, in particular Pseudomonas sp. CF600; Pelomaculum, in particular Pelotomaculum thermopropionicum. Preferably, the nucleic acid sequence encoding the NADH-dependent acetylating acetaldehyde dehydrogenase originates from Escherichia, more preferably from E. coli.

Particularly suitable is an mhpF gene from E. coli, or a functional homologue thereof. This gene is described in Ferrandez et al. (1997) J. Bacteriol. 179:2573-2581. Good results have been obtained with S. cerevisiae, wherein an mhpF gene from E. coli has been incorporated.

In a further advantageous embodiment the nucleic acid sequence encoding an (acetylating) acetaldehyde dehydrogenase is from, in particular *Pseudomonas* dmpF from *Pseudomonas* sp. CF600.

In principle, the nucleic acid sequence encoding the NAD+-dependent, acetylating acetaldehyde dehydrogenase may be a wild type nucleic acid sequence. A preferred nucleic acid sequence encodes the NAD+-dependent, acetylating acetaldehyde dehydrogenase represented by SEQ ID NO: 2, SEQ ID NO: 29 in WO2011010923, or a functional homologue of SEQ ID NO: 2 or SEQ ID NO: 29 in WO2011010923. In particular the nucleic acid sequence comprises a sequence according to SEQ ID NO: 1. SEQ ID NO: 28 in WO2011010923 or a functional homologue of SEQ ID NO: 1 or SEQ ID NO: 28 in WO2011010923.

Further, an acetylating acetaldehyde dehydrogenase (or nucleic acid sequence encoding such activity) may in for instance be selected from the group of *Escherichia coli* adhE, *Entamoeba histolytica* adh2, *Staphylococcus aureus* adhE, *Piromyces* sp.E2 adhE, *Clostridium kluyveri* EDK33116, *Lactobacillus plantarum* acdH, and *Pseudomonas putida* YP 001268189. For sequences of these enzymes, nucleic acid sequences encoding these enzymes and methodology to incorporate the nucleic acid sequence into a host cell, reference is made to WO 20091013159, in particular Example 3, Table 1 (page 26) and the Sequence ID numbers mentioned therein, of which publication Table 1 and the sequences represented by the Sequence ID numbers mentioned in said Table are incorporated herein by reference.

It is further understood, that in a preferred embodiment, that the cell has endogenous alcohol dehydrogenase activities which allow the cell, being provided with acetaldehyde dehydrogenase activity, to complete the conversion of acetyl-CoA into ethanol. It is further also preferred that the host cell has endogenous acetyl-CoA synthetase which allow the cell, being provided with acetaldehyde dehydrogenase activity, to complete the conversion of acetic acid (via acetyl-CoA) into ethanol.

The exogenous gene coding for an enzyme with acetaldehyde dehydrogenase activity preferably comprises a nucleotide sequence coding for an amino acid sequence with at least 40, 50, 60, 65, 70, 75, 80, 85, 90, 95, 98, 99% amino acid sequence identity with any of SEQ ID's NO: 1 to SEQ ID NO: 5, preferably of SEQ ID NO: 1 to SEQ ID NO: 3, more preferably of SEQ ID NO: 1 or SEQ ID NO: 2. The exogenous gene coding for an enzyme with acetaldehyde dehydrogenase activity may also comprises a nucleotide sequence coding for an amino acid sequence having one or several substitutions, insertions and/or deletions as compared to the amino acid sequence of any of SEQ ID's NO: 1 to SEQ ID NO: 5, preferably of SEQ ID NO: 1 to SEQ ID NO: 3, more preferably of SEQ ID NO: 1 or SEQ ID NO: 2. Preferably the amino acid sequence has no more than 420, 380, 300, 250, 200, 150, 100, 75, 50, 40, 30, 20, 10 or 5 amino acid substitutions, insertions and/or deletions as compared to SEQ ID's NO: 1 to SEQ ID NO: 5 respectively, preferably to SEQ ID NO: 1 to SEQ ID NO: 3 respectively, more preferably to SEQ ID NO: 1 or SEQ ID NO: 2 respectively.

The exogenous gene coding for an enzyme with acetaldehyde dehydrogenase herein comprises a nucleotide sequence with at least 40, 50, 60, 65, 70, 75, 80, 85, 86, 87, 88, 89, 90, 95, 96, 97, 98, 99% or 100% nucleotide (DNA) sequence identity with any of SEQ ID's NO: Y, wherein SEQ ID NO: Y is any of the nucleotide (DNA) sequences 48-52.

Some organisms that could be a source of adhE enzymes that may be suitable for expression in the cell of the invention are mentioned in table 1.

TABLE 1

Organism with enzymes with alcohol/acetaldehyde dehydrogenase (adhE) activity

Organism

*Piromyces* sp E2
*Arthrospira platensis*
*Synechococcus* sp.
*Microcystis aeruginosa*
*Microcoleus chthonoplastes*
*Lyngbya* sp.
*Thermosynechococcus elongatus*
*Treponema phagedenis*
*Clostridium difficile*
*Clostridium carboxidivorans*
*Clostridium acetobutylicum*

Examples of suitable enzymes are adhE of *Escherichia coli*, acdH of *Lactobacillus plantarum*, eutE of *Escherichia coli*, Lin1129 of *Listeria innocua* and adhE from *Staphylococcus aureus*. See below tables 2(a) to 2(e) for BLAST of these enzymes, giving suitable alternative alcohol/acetaldehyde dehydrogenases that are tested in the examples below.

TABLE 2(a)

BLAST Query - adHE from *Escherichia coli*

| Description | Identity (%) | Accession number |
| --- | --- | --- |
| bifunctional acetaldehyde-CoA/alcohol dehydrogenase [*Escherichia coli* O157:H7 str. Sakai] | 100 | NP_309768.1 |
| bifunctional acetaldehyde-CoA/alcohol dehydrogenase [*Escherichia coli* UTI89] | 99 | YP_540449.1 |
| bifunctional acetaldehyde-CoA/alcohol dehydrogenase [*Enterobacter* sp. 638] | 95 | YP_001177024.1 |

TABLE 2(b)

BLAST Query - acdH from *Lactobacillus plantarum*

| Description | Identity (%) | Accession number |
| --- | --- | --- |
| acetaldehyde dehydrogenase [*Lactobacillus plantarum* WCFS1] | 100 | YP_004888365.1 |
| acetaldehyde dehydrogenase [*Lactobacillus pentosus* IG1] | 95 | CCC16763.1 |
| aldehyde-alcohol dehydrogenase [*Enterococcus cecorum*] | 58 | WP_016251441.1 |
| aldehyde-alcohol dehydrogenase 2 [*Enterococcus faecalis*] | 57 | WP_016623694.1 |
| bifunctional acetaldehyde-CoA/alcohol dehydrogenase [*Lactobacillus zeae*] | 55 | WP_010493695.1 |
| alcohol dehydrogenase [*Bacillus thuringiensis*] | 54 | WP_003280110.1 |
| bifunctional acetaldehyde-CoA/alcohol dehydrogenase, partial [*Listeria monocytogenes*] | 53 | WP_009931954.1 |

TABLE 2(c)

BLAST Query - eutE from *Escherichia coli*

| Description | Identity (%) | Accession number |
|---|---|---|
| aldehyde oxidoreductase, ethanolamine utilization protein [*Escherichia coli* str. K-12 substr. MG1655] | 100 | NP_416950.1 |
| ethanolamine utilization; acetaldehyde dehydrogenase [*Escherichia coli* O157:H7 str. EDL933] | 99 | NP_289007.1 |
| aldehyde dehydrogenase [*Escherichia albertii*] | 99 | WP_001075674.1 |

TABLE 2(d)

BLAST Query - Lin1129 from *Listeria innocua*

| Description | Identity (%) | Accession number |
|---|---|---|
| aldehyde dehydrogenase [*Listeria innocua*] >emb\|CAC96360.1\|lin1129 [*Listeria innocua* Clip11262] | 100 | NP_470466.1 |
| ethanolamine utilization protein EutE [*Listeria innocua*] | 99 | WP_003761764.1 |
| aldehyde dehydrogenase [*Listeria monocytogenes*] | 95 | AGR09081.1 |
| hypothetical protein [*Enterococcus malodoratus*] | 64 | WP_010739890.1 |
| aldehyde dehydrogenase [*Yersinia aldovae*] | 59 | WP_004699364.1 |
| aldehyde dehydrogenase EutE [*Klebsiella pneumoniae*] | 58 | WP_004205473.1 |

TABLE 2(e)

BLAST Query - adhE from *Staphylococcus aureus*

| Description | Identity (%) | Accession number |
|---|---|---|
| bifunctional acetaldehyde-CoA/alcohol dehydrogenase [*Staphylococcus aureus* subsp. *aureus* Mu50] | 100 | NP_370672.1 |
| aldehyde dehydrogenase family protein [*Staphylococcus aureus* CA-347] | 99 | YP_008127042.1 |
| bifunctional acetaldehyde-CoA/alcohol dehydrogenase [*Staphylococcus epidermidis*] | 85 | WP_002495347.1 |
| aldehyde-alcohol dehydrogenase 2 [*Enterococcus faecalis*] | 75 | WP_016623694.1 |

Feature b: one or more nucleotide sequence encoding a acetyl-CoA synthetase (E.C. 6.2.1.1);

Acetyl-CoA synthetase (also known as acetate-CoA ligase and acetyl-activating enzyme) is a ubiquitous enzyme, found in both prokaryotes and eukaryotes, which catalyses the formation of acetyl-CoA from acetate, coenzyme A (CoA) and ATP as shown below [PMID: 15316652]:

ATP+acetate+CoA=AMP+diphosphate+acetyl–CoA  (4)

The activity of this enzyme is crucial for maintaining the required levels of acetyl-CoA, a key intermediate in many important biosynthetic and catabolic processes. It is especially important in eukaryotic species as it is the only route for the activation of acetate to acetyl-CoA in these organisms (some prokaryotic species can also activate acetate by either acetate kinase/phosphotransacetylase or by ADP-forming acetyl-CoA synthase). Eukaryotes typically have two isoforms of acetyl-CoA synthase, a cytosolic form involved in biosynthetic processes and a mitochondrial form primarily involved in energy generation.

The crystal structures of a eukaryotic (e.g. from yeast) and bacterial (e.g. from *Salmonella*) form of this enzyme have been determined. The yeast enzyme is trimeric, while the bacterial enzyme is monomeric. The trimeric state of the yeast protein may be unique to this organism however, as the residues involved in the trimer interface are poorly conserved in other sequences. Despite differences in the oligomeric state of the two enzyme, the structures of the monomers are almost identical. A large N-terminal domain (~500 residues) containing two parallel beta sheets is followed by a small (~110 residues)C-terminal domain containing a three-stranded beta sheet with helices. The active site occurs at the domain interface, with its contents determining the orientation of the C-terminal domain.

When the cell is a yeast cell the endogenous ACS are preferred according to the invention, in an embodiment they are overexpressed in yeast cell.

Examples of suitable are listed in table 3. At the top of table 3 the ACS2 used in the examples and that is BLASTED is mentioned.

TABLE 3

BLAST Query - ACS2 from *Saccharomyces cerevisiae*

| Description | Identity (%) | Accession number |
|---|---|---|
| acetate--CoA ligase ACS2 [*Saccharomyces cerevisiae* S288c] | 100 | NP_013254.1 |
| acetyl CoA synthetase [*Saccharomyces cerevisiae* YJM789] | 99 | EDN59693.1 |
| acetate--CoA ligase [*Kluyveromyces lactis* NRRL Y- 1140] | 85 | XP_453827.1 |
| acetate--CoA ligase [*Candida glabrata* CBS 138] | 83 | XP_445089.1 |
| acetate--CoA ligase [*Scheffersomyces stipitis* CBS 6054] | 68 | XP_001385819.1 |
| acetyl-coenzyme A synthetase FacA [*Aspergillus fumigatus* A1163] | 63 | EDP50475.1 |
| acetate--CoA ligase facA-*Penicillium chrysogenum* [*Penicillium chrysogenum* Wisconsin 54-1255] | 62 | XP_002564696.1 |

The exogenous gene coding for an enzyme with ACS activity preferably comprises a nucleotide sequence coding for an amino acid sequence with at least 50, 60, 65, 70, 75, 80, 85, 90, 95, 98, 99% amino acid sequence identity with SEQ ID NO: 6. The exogenous gene coding for an enzyme with ACS activity may also comprises a nucleotide sequence coding for an amino acid sequence having one or several substitutions, insertions and/or deletions as compared to the amino acid sequence of SEQ ID's NO: 6. Preferably the amino acid sequence has no more than 420, 380, 300, 250, 200, 150, 100, 75, 50, 40, 30, 20, 10 or 5 amino acid substitutions, insertions and/or deletions as compared to SEQ ID's NO: 6.

The exogenous gene coding for an enzyme with ACS activity herein comprises a nucleotide sequence with at least 40, 50, 60, 65, 70, 75, 80, 85, 86, 87, 88, 89, 90, 95, 96, 97, 98, 99% or 100% nucleotide (DNA) sequence identity with SEQ ID's NO: 53.

Feature c): According to feature c), the cell comprises one or more nucleotide sequence encoding a glycerol dehydrogenase (E.C. 1.1.1.6). Glycerol dehydrogenase (EC 1.1.1.6) is an enzyme that catalyzes the chemical reaction $$glycerol+NAD^+ \rightleftharpoons glycerone+NADH+H^+ \quad (5)$$

Thus, the two substrates of this enzyme are glycerol and NAD+, whereas its three products are glycerone, NADH, and H+. Glyceron and dihydroxyacetone are herein synonyms.

This enzyme belongs to the family of oxidoreductases, specifically those acting on the CH—OH group of donor with NAD+ or NADP+ as acceptor. The systematic name of this enzyme class is glycerol:NAD+ 2-oxidoreductase. Other names in common use include glycerin dehydrogenase, and NAD+-linked glycerol dehydrogenase. This enzyme participates in glycerolipid metabolism. Structural studies have shown that the enzyme is zinc-dependent with the active site lying between the two domains of the protein.

Examples of suitable glycerol dehydrogenases are listed in table 4(a) to 4(d). At the top of each table the gldA used in the examples and that is BLASTED is mentioned.

TABLE 4(a)

BLAST Query - gldA from *Escherichia coli*

| Description | Identity (%) | Accession number |
|---|---|---|
| glycerol dehydrogenase, NAD [*Escherichia coli* str. K-12 substr. MG1655] | 100 | NP_418380.4 |
| glycerol dehydrogenase [*Escherichia coli* O127:H6 str. E2348/69] | 99 | YP_002331714.1 |
| glycerol dehydrogenase [*Citrobacter youngae*] | 94 | WP_006686227.1 |
| glycerol dehydrogenase [*Citrobacter freundii*] | 92 | WP_003840533.1 |

TABLE 4(b)

BLAST Query - gldA from *Klebsiella pneumoniae*

| Description | Identity (%) | Accession number |
|---|---|---|
| glycerol dehydrogenase [*Klebsiella pneumoniae* 342] | 100 | YP_002236495.1 |
| glycerol dehydrogenase [*Citrobacter freundii*] | 93 | WP_003024745.1 |
| Glycerol dehydrogenase (EC 1.1.1.6) [*Enterobacter aerogenes* EA1509E] | 92 | YP_004590977.1 |
| glycerol dehydrogenase [*Escherichia coli*] | 91 | WP_016241524.1 |
| glycerol dehydrogenase [*Enterococcus aerogenes*] | 87 | See examples herein strains with CAS15 |
| glycerol dehydrogenase [*Yersinia aldovae*] | 74 | WP_004701845.1 |
| glycerol dehydrogenase [Enterobacteriaceae bacterium LSJC7] | 61 | WP_017375113.1 |
| glycerol dehydrogenase [*Citrobacter youngae*] | 60 | WP_006686227.1 |

TABLE 4(c)

BLAST Query - gldA from *Enterococcus aerogenes*

| Description | Identity (%) | Accession number |
|---|---|---|
| glycerol dehydrogenase [*Enterobacter aerogenes* KCTC 2190] | 100 | YP_004591726.1 |
| Glycerol dehydrogenase (EC 1.1.1.6) [*Enterobacter aerogenes* EA1509E] | 99 | YP_007390021.1 |
| glycerol dehydrogenase [*Klebsiella pneumoniae*] | 92 | WP_004203683.1 |

TABLE 4(c)-continued

BLAST Query - gldA from *Enterococcus aerogenes*

| Description | Identity (%) | Accession number |
|---|---|---|
| glycerol dehydrogenase [*Escherichia coli*] | 88 | WP_001322519.1 See examples herein strains with CAS13 |
| glycerol dehydrogenase [*Enterobacter cloacae* subsp. *cloacae* ATCC 13047] | 87 | YP_003615506.1 |

TABLE 4(d)

BLAST Query - gldA from *Yersinia aldovae*

| Description | Identity (%) | Accession number |
|---|---|---|
| glycerol dehydrogenase [*Yersinia aldovae*] | 100 | WP_004701845.1 |
| glycerol dehydrogenase [*Yersinia intermedia*] | 95 | WP_005189747.1 |
| glycerol dehydrogenase [*Serratia liquefaciens* ATCC 27592] | 81 | YP_008232202.1 |
| glycerol dehydrogenase [*Escherichia coli*] | 76 | WP_016241524.1 See examples herein strains with CAS13. |
| hypothetical protein EAE_03845 [*Enterobacter aerogenes* KCTC 2190] | 75 | YP_004590977.1 |
| glycerol dehydrogenase [*Aeromonas hydrophila*] | 65 | WP_017410769.1 |

The exogenous gene coding for an enzyme with gldA activity preferably comprises a nucleotide sequence coding for an amino acid sequence with at least 50, 60, 65, 70, 75, 80, 85, 90, 95, 98, 99% amino acid sequence identity with any of SEQ ID's NO: 7 to SEQ ID NO: 10, preferably of SEQ ID NO:7 or SEQ ID NO: 9. The exogenous gene coding for an enzyme with acetaldehyde dehydrogenase activity may also comprises a nucleotide sequence coding for an amino acid sequence having one or several substitutions, insertions and/or deletions as compared to the amino acid sequence of any of SEQ ID's NO: 7 to SEQ ID NO: 10, preferably of SEQ ID NO:7 or SEQ ID NO: 9. Preferably the amino acid sequence has no more than 300, 250, 200, 150, 100, 75, 50, 40, 30, 20, 10 or 5 amino acid substitutions, insertions and/or deletions as compared to SEQ ID's NO: 7, SEQ ID NO:8, SEQ ID NO:9 or SEQ ID NO: 10 respectively, preferably to SEQ ID NO:7 or SEQ ID NO: 9 respectively.

The exogenous gene coding for an enzyme with gldA activity herein comprises a nucleotide sequence with at least 40, 50, 60, 65, 70, 75, 80, 85, 86, 87, 88, 89, 90, 95, 96, 97, 98, 99% or 100% nucleotide (DNA) sequence identity with any of SEQ ID's NO: 54-57.

Feature d): one or more heterologous nucleotide sequence encoding a dihydroxyacetone kinase (E.C. 2.7.1.28 or E.C. 2.7.1.29), The dihydroxyacetone kinase enzyme is involved in reactions:

EC 2.7.1.28

ATP + D-glyceraldehyde <=> ADP + D-glyceraldehyde 3-phosphate

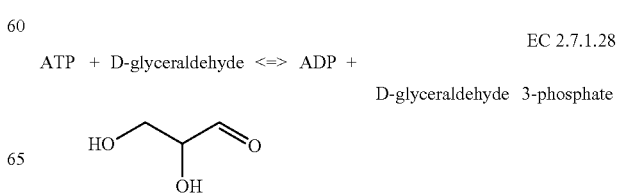

EC 2.7.1.29

ATP + glycerone <=> ADP + glycerone phosphate

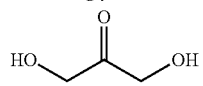
Glycerone = dihydroxyacetone.

This family consists of examples of the single chain form of dihydroxyacetone kinase (also called glycerone kinase) that uses ATP (EC 2.7.1.29 or EC 2.7.1.28) as the phosphate donor, rather than a phosphoprotein as in *Escherichia coli*. This form has separable domains homologous to the K and L subunits of the *E. coli* enzyme, and is found in yeasts and other eukaryotes and in some bacteria, including *Citrobacter freundii*. The member from tomato has been shown to phosphorylate dihydroxyacetone, 3,4-dihydroxy-2-butanone, and some other aldoses and ketoses. Members from mammals have been shown to catalyse both the phosphorylation of dihydroxyacetone and the splitting of ribonucleoside diphosphate-X compounds among which FAD is the best substrate. In yeast there are two isozymes of dihydroxyacetone kinase (Dak1 and Dak2). When the cell is a yeast cell the endogenous DAK's are preferred according to the invention, in an embodiment they are overexpressed in yeast cell.

Examples of suitable dihydroxyacetone kinases are listed in table 5(a) to 5(d). At the top of each table the DAK's used in the examples and that is BLASTED is mentioned.

TABLE 5(a)

BLAST Query - DAK1 from *Saccharomyces cerevisiae*

| Description | Identity (%) | Accession number |
|---|---|---|
| Dak1p [*Saccharomyces cerevisiae* S288c] | 100 | NP_013641.1 |
| dihydroxyacetone kinase [*Saccharomyces cerevisiae* YJM789] | 99 | EDN64325.1 |
| DAK1-like protein [*Saccharomyces kudriavzevii* IFO 1802] | 95 | EJT44075.1 |
| ZYBA0S11-03576g1_1 [*Zygosaccharomyces bailii* CLIB 213] | 77 | CDF91470.1 |
| hypothetical protein [*Kluyveromyces lactis* NRRL Y-1140] | 70 | XP_451751.1 |
| hypothetical protein [*Candida glabrata* CBS 138] | 63 | XP_449263.1 |
| Dak2p [*Saccharomyces cerevisiae* S288c] | 44 | NP_116602.1 |
| DAK1 [*Yarrowia lipolytica*] | 41 | See examples herein strains with CAS23 |

TABLE 5(b)

BLAST Query - dhaK from *Klebsiella pneumoniae*

| Description | Identity (%) | Accession number |
|---|---|---|
| dihydroxyacetone kinase subunit DhaK [*Klebsiella pneumoniae* 342] | 100 | YP_002236493.1 |
| dihydroxyacetone kinase subunit K [*Klebsiella pneumoniae*] | 99 | WP_004149886.1 |
| dihydroxyacetone kinase subunit K [*Enterobacter aerogenes*] | 96 | WP_020077889.1 |
| dihydroxyacetone kinase subunit DhaK [*Escherichia coli* IAI39] | 88 | YP_002407536.1 |
| dihydroxyacetone kinase, DhaK subunit [*Escherichia coli*] | 87 | WP_001398949.1 |

TABLE 5(c)

BLAST Query - DAK1 from *Yarrowia lipolytica*

| Description | Identity (%) | Accession number |
|---|---|---|
| YALI0F09273p [*Yarrowia lipolytica*] | 100 | XP_505199.1 |
| dihydroxyacetone kinase [*Schizosaccharomyces pombe*] | 46 | AAC83220.1 |
| dihydroxyacetone kinase Dak1 [*Schizosaccharomyces pombe* 972h-] | 45 | NP_593241.1 |
| dihydroxyacetone kinase [*Saccharomyces cerevisiae* RM11-1a] | 44 | EDV12567.1 |
| Dak2p [*Saccharomyces cerevisiae* JAY291] | 44 | EEU04233.1 |
| BN860_19306g1_1 [*Zygosaccharomyces bailii* CLIB 213] | 44 | CDF87998.1 |
| Dak1p [*Saccharomyces cerevisiae* CEN.PK113-7D] | 42 | EIW08612.1 See examples herein strains with CAS21 |

TABLE 5(d)

BLAST Query - DAK1 from *Schizosaccharomyces pombe*

| Description | Identity (%) | Accession number |
|---|---|---|
| dihydroxyacetone kinase Dak1 [*Schizosaccharomyces pombe* 972h-] | 100 | NP_593241.1 |
| putative dihydroxyacetone kinase protein [*Botryotinia fuckeliana* BcDW1] | 48 | EMR88164.1 |
| Dihydroxyacetone kinase 1 [*Fusarium oxysporum* f. sp. *cubense* race 1] | 48 | ENH64704.1 |
| Dak1p [*Saccharomyces cerevisiae* CEN.PK113-7D] | 46 | EIW08612.1 |
| Dak2p [*Saccharomyces cerevisiae* JAY291] | 44 | EEU04233.1 |
| dihydroxyacetone kinase [*Exophiala dermatitidis* NIH/UT8656] | 42 | EHY55064.1 |

The exogenous gene coding for an enzyme with DAK activity preferably comprises a nucleotide sequence coding for an amino acid sequence with at least 40, 50, 60, 65, 70, 75, 80, 85, 90, 95, 98, 99% amino acid sequence identity with any of SEQ ID's NO: 11 to SEQ ID NO: 14, preferably SEQ ID NO: 11 or SEQ ID NO: 13. The exogenous gene coding for an enzyme with acetaldehyde dehydrogenase activity may also comprises a nucleotide sequence coding for an amino acid sequence having one or several substitutions, insertions and/or deletions as compared to the amino acid sequence of any of SEQ ID's NO: 11 to SEQ ID NO: 14, preferably SEQ ID NO: 11 or SEQ ID NO: 13. Preferably the amino acid sequence has no more than 420, 380, 300, 250, 200, 150, 100, 75, 50, 40, 30, 20, 10 or 5 amino acid substitutions, insertions and/or deletions as compared to SEQ ID NO: 11, SEQ NO: 12, SEQ ID NO; 13 or SEQ ID NO: 14 respectively, preferably to SEQ ID NO: 11 or SEQ ID NO: 13 respectively.

The exogenous gene coding for an enzyme with DAK activity herein comprises a nucleotide sequence with at least 40, 50, 60, 65, 70, 75, 80, 85, 86, 87, 88, 89, 90, 95, 96, 97, 98, 99% or 100% nucleotide (DNA) sequence identity with any of SEQ ID's NO: 58-61.

In an embodiment, the cell comprises a deletion or disruption of one or more endogenous nucleotide sequence encoding a glycerol 3-phosphate phosphohydrolase and/or encoding a glycerol 3-phosphate dehydrogenase gene:

Herein in the cell, enzymatic activity needed for the NADH-dependent glycerol synthesis is reduced or deleted. The reduction or deleted of this enzymatic activity can be achieved by modifying one or more genes encoding a NAD-dependent glycerol 3-phosphate dehydrogenase activity (GPD) or one or more genes encoding a glycerol phosphate phosphatase activity (GPP), such that the enzyme is expressed considerably less than in the wild-type or such that the gene encoded a polypeptide with reduced activity.

Such modifications can be carried out using commonly known biotechnological techniques, and may in particular include one or more knock-out mutations or site-directed mutagenesis of promoter regions or coding regions of the structural genes encoding GPD and/or GPP. Alternatively, yeast strains that are defective in glycerol production may be obtained by random mutagenesis followed by selection of strains with reduced or absent activity of GPD and/or GPP. S. cerevisiae GPD1, GPD2, GPP1 and GPP2 genes are shown in WO2011010923, and are disclosed in SEQ ID NO: 24-27 of that application.

Preferably at least one gene encoding a GPD or at least one gene encoding a GPP is entirely deleted, or at least a part of the gene is deleted that encodes a part of the enzyme that is essential for its activity. In particular, good results have been achieved with a S. cerevisiae cell, wherein the open reading frames of the GPD1 gene and of the GPD2 gene have been inactivated. Inactivation of a structural gene (target gene) can be accomplished by a person skilled in the art by synthetically synthesizing or otherwise constructing a DNA fragment consisting of a selectable marker gene flanked by DNA sequences that are identical to sequences that flank the region of the host cell's genome that is to be deleted. In particular, good results have been obtained with the inactivation of the GPD1 and GPD2 genes in Saccharomyces cerevisiae by integration of the marker genes kanMX and hphMX4. Subsequently this DNA fragment is transformed into a host cell. Transformed cells that express the dominant marker gene are checked for correct replacement of the region that was designed to be deleted, for example by a diagnostic polymerase chain reaction or Southern hybridization.

Thus, in the cells of the invention, the specific glycerol 3-phosphate phosphohydrolase and/or encoding a glycerol 3-phosphate dehydrogenase gene is reduced. In the cells of the invention, the specific glycerolphosphate dehydrogenase activity is preferably reduced by at least a factor 0.8, 0.5, 0.3, 0.1, 0.05 or 0.01 as compared to a strain which is genetically identical except for the genetic modification causing the reduction in specific activity, preferably under anaerobic conditions. Glycerolphosphate dehydrogenase activity may be determined as described by Overkamp et al. (2002, Yeast 19:509-520).

Preferably, the genetic modifications reduce or inactivate the expression of each endogenous copy of the gene encoding a specific glycerolphosphate dehydrogenase in the cell's genome. A given cell may comprise multiple copies of the gene encoding a specific glycerolphosphate dehydrogenase with one and the same amino acid sequence as a result of di-, poly- or aneuploidy. In such instances preferably the expression of each copy of the specific gene that encodes the glycerolphosphate dehydrogenase is reduced or inactivated. Alternatively, a cell may contain several different (iso) enzymes with glycerolphosphate dehydrogenase activity that differ in amino acid sequence and that are each encoded by a different gene. In such instances, in some embodiments of the invention it may be preferred that only certain types of the isoenzymes are reduced or inactivated while other types remain unaffected. Preferably, however, expression of all copies of genes encoding (iso)enzymes with glycerolphosphate dehydrogenase activity is reduced or inactivated.

Preferably, a gene encoding glycerolphosphate dehydrogenase activity is inactivated by deletion of at least part of the gene or by disruption of the gene, whereby in this context the term gene also includes any non-coding sequence up- or down-stream of the coding sequence, the (partial) deletion or inactivation of which results in a reduction of expression of glycerolphosphate dehydrogenase activity in the host cell.

A preferred gene encoding a glycerolphosphate dehydrogenase whose activity is to be reduced or inactivated in the cell of the invention is the S. cerevisiae GPD1 as described by van den Berg and Steensma (1997, Yeast 13:551-559), encoding the amino acid sequence GPD1 and orthologues thereof in other species.

Suitable examples of organisms (hosts) comprising an enzyme with glycerolphosphate dehydrogenase activity belonging to the genus Saccharomyces, Naumovozyna, Candida Vanderwaltozyma and Zygosaccharomyces are provided in Table 6.

TABLE 6

Enzymes with glycerophosphate dehydrogenase (GPD1) activity

| Organism | Amino acid identity (%) |
|---|---|
| S. cerevisiae | 100% |
| Naumovozyma dairenensis | 79% |
| Naumovozyma castellii | 80% |
| Candida glabrata | 77% |
| Vanderwaltozyma polyspora | 77% |
| Zygosaccharomyces rouxii | 74% |
| Saccharomycopsis fibuligera | 61% |

However, in some strains e.g. of Saccharomyces, Candida and Zygosaccharomyces a second gene encoding a glycerolphosphate dehydrogenase is active, i.e. the GPD2, see e.g. Overkamp et al. (2002, supra). Another preferred gene encoding a glycerolphosphate dehydrogenase whose activity is to be reduced or inactivated in the cell of the invention therefore is an S. cerevisiae GPD2 as described by Overkamp et al. (2002, supra), encoding the amino acid sequence GPD2 and orthologues thereof in other species.

Suitable examples of organisms (hosts) comprising an enzyme with glycerolphosphate dehydrogenase activity belonging to the genus (Zygo) Saccharomyces and Candida are provided in Table 7.

TABLE 7

Enzymes with glycerol phosphate dehydrogenase (GPD2) activity

| Organism | Amino acid identity (%) |
|---|---|
| S. cerevisiae | 100% |
| Candida glabrata | 75% |
| Zygosaccharomyces rouxii | 73% |
| Spathaspora passalidarum | 62% |
| Scheffersomyces stipitis | 61% |

In an embodiment, the cell is a yeast wherein the genome of the yeast cell comprises a mutation in at least one gene selected from the group of GPD1, GPD2, GPP1 and GPP2, which mutation may be a knock-out mutation, which knock-out mutation may be a complete deletion of at least one of said genes in comparison to the yeast cell's corresponding wild-type yeast gene.

To increase the likelihood that the enzyme activities herein are expressed at sufficient levels and in active form in the transformed host cells of the invention, the nucleotide sequence encoding these enzymes, and other enzymes of the invention (see below), are preferably adapted to optimise their codon usage to that of the host cell in question. The adaptiveness of a nucleotide sequence encoding an enzyme to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51). An adapted nucleotide sequence preferably has a CAI of at least 0.2, 0.3, 0.4, 0.5, 0.6, 0.7, 0.8 or 0.9. Most preferred are the sequences which have been codon optimised for expression in the fungal host cell in question such as e.g. S. cerevisiae cells.

Strain construction. The strain construction approach used herein in the examples is described in patent application PCT/EP2013/056623. It describes the techniques enabling the construction of expression cassettes from various genes of interest in such a way, that these cassettes are combined into a pathway and integrated in a specific locus of the yeast genome upon transformation of this yeast.

An overview of strain construction approach used in the examples is given in FIG. 2. FIG. 2 shows a schematic display of the strain construction approach. INT (integration) flanks and expression cassettes (CAS), including selectable marker, are amplified using PCR and transferred into yeast. Recombination will take place between the connectors (designated 5, a, b, c and 3 respectively in FIG. 2) resulting in the integration of the pathway in the desired location in the yeast genome (in this case, INT1). The number of genes of interest may be extended, as described in the examples. Unique connectors were used to facilitate recombination of the separate expression cassettes and integration into the genome of the recipient cell. Any other strain construction methods according to the prior art may equally be used to construct the strains of the invention.

Homology & Identity.

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" is frequently used interchangeably.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch. C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp276-277, http://emboss.bioinformatics.nl/). For protein sequences, EBLOSUM62 as is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

Global Homology Definition

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

Longest Identity Definition

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity".

The various embodiments of the invention described herein may be cross-combined.

Further embodiments of the invention.

In an embodiment, the yeast cell comprises one or more nucleic acid sequences encoding encoding NAD+-dependent alcohol dehydrogenase activity (EC 1.1.1.1). This enzyme catalyses the conversion of acetaldehyde into ethanol. The yeast cell may naturally comprise a gene encoding such a dehydrogenase, as is the case with S. cerevisiae (ADH1-5), see 'Lutstorf and Megnet. 1968 Arch. Biochem. Biophys. 126:933-944', or 'Ciriacy, 1975, Mutat. Res. 29:315-326'), or a host cell may be provided with one or more heterologous gene(s) encoding this activity, e.g. any or each of the ADH1-5 genes of S. cerevisiae or functional homologues thereof may be incorporated into a cell according to the invention.

In an embodiment, the yeast cell is selected from Saccharomycetaceae, in particular from the group of Saccharomyces, such as Saccharomyces cerevisiae; Kluyveromyces, such as Kluyveromyces marxianus; Pichia, such as Pichia stipitis or Pichia angusta; Zygosaccharomyces, such as Zygosaccharomyces bailii; and Brettanomyces, such as Brettanomyces intermedius, Issatchenkia, such as Issatchenkia orientalis and Hansenula.

In an embodiment, the cell is a prokaryotic cell. In an embodiment the cell is selected from the list consisting of Clostridium, Zymomonas, Thermobacter Escherichia, Lactobacillus, Geobacillus and Bacillus.

The invention further relates to the use of a yeast cell according to the invention for the preparation of fermentation product, preferably ethanol. The invention further provides a process for preparing fermentation product, comprising preparing fermentation product from acetate and from a fermentable carbohydrate—in particular a carbohydrate selected from the group of glucose, fructose, sucrose, maltose, xylose, arabinose, galactose and mannose—which preparation is carried out under anaerobic conditions using a yeast cell according to the invention. In an embodiment, the preparation is carried out in a fermentation medium comprising the acetate and the carbohydrate in a molar ratio is 0.7 or less, in particular at least 0.004 to 0.5, more in particular 0.05 to 0.3. In an embodiment of the preparation of fermentation product, at least part of the carbohydrate and at least part of the acetate has been obtained by hydrolysing a polysaccharide selected from the group of lignocelluloses, celluloses, hemicelluloses, and pectins. The lignocellulose is preferably lignocellulosic biomass that has been hydrolysed thereby obtaining the fermentable carbohydrate and acetate.

In an embodiment, the ligno-cellulosic or hemi-cellulosic material is contacted with an enzyme composition, wherein one or more sugar is produced, and wherein the produced sugar is fermented to give a fermentation product, wherein the fermentation is conducted with a yeast cell according to the invention.

The fermentation product of the invention may be any useful product. In one embodiment, it is a product selected from the group consisting of ethanol, n-butanol, isobutanol, lactic acid, 3-hydroxy-propionic acid, acrylic acid, acetic acid, succinic acid, adipic acid, fumaric acid, malic acid, itaconic acid, maleic acid, citric acid, adipic acid, an amino acid, such as lysine, methionine, tryptophan, threonine, and aspartic acid, 1,3-propane-diol, ethylene, glycerol, a β-lactam antibiotic and a cephalosporin, vitamins, pharmaceuticals, animal feed supplements, specialty chemicals, chemical feedstocks, plastics, solvents, fuels, including biofuels and biogas or organic polymers, and an industrial enzyme, such as a protease, a cellulase, an amylase, a glucanase, a lactase, a lipase, a lyase, an oxidoreductases, a transferase or a xylanase.

In an embodiment, the fermentation product may be one or more of ethanol, butanol, lactic acid, a plastic, an organic acid, a solvent, an animal feed supplement, a pharmaceutical, a vitamin, an amino acid, an enzyme or a chemical feedstock.

In a preferred embodiment the cell is grown anaerobically. Anaerobic growth conditions are herein anaerobic or oxygen limited. Anaerobic is here defined as a growth process run in the absence of oxygen or in which substantially no oxygen is consumed, preferably less than about 5, about 2.5 or about 1 mmol/L/h, and wherein organic molecules serve as both electron donor and electron acceptors.

An oxygen-limited growth process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6, such as at least 7 mmol/L/h. A process of the invention comprises recovery of the fermentation product. During fermentation, when acetic acid is present, the ratio of acetic acid/acetate will depend on pH. The concentration of acetate in step d) may be chosen similar to the concentration the yeast strain meets in its end use (e.g. in fermentation of lignocellulosic hydrolysate to fermentation product, such hydrolyate may contain 1-10 g/l acetate, e.g. 2 g/l acetate.

Advantageously, when in accordance with the invention ethanol is produced, it is produced in a molar ratio of glycerol:ethanol of less than 0.04:1, in particular of less than 0.02:1, preferably of less than 0.01:1. Glycerol production may be absent (undetectable), although at least in some embodiments (wherein NADH-dependent glycerol synthesis is reduced yet not completely prohibited) some glycerol may be produced as a side product, e.g. in a ratio glycerol to ethanol of 0.001:1 or more.

The present invention allows complete elimination of glycerol production, or at least a significant reduction thereof, by providing a recombinant yeast cell, in particular S. cerevisiae, such that it can reoxidise NADH by the reduction of acetic acid to ethanol via NADH-dependent reactions.

This is not only advantageous in that glycerol production is avoided or at least reduced, but since the product formed in the re-oxidation of NADH is also the desired product, namely ethanol, a method of the invention may also offer an increased product yield (determined as the wt. % of converted feedstock, i.e. carbohydrate plus acetic acid, that is converted into ethanol). Since acetic acid is generally available at significant amounts in lignocellulosic hydrolysates, this makes the present invention particularly advantageous for the preparation of ethanol using lignocellulosic biomass as a source for the fermentable carbohydrate. Further, carbohydrate sources that may contain a considerable amount of acetate include sugar beet molasses (hydrolysates of) and starch containing (e.g. waste products from corn dry milling processes, from corn wet milling processes; from starch wastes processes. e.g. with stillage recycles).

In a further preferred embodiment, the host cell of the invention has at least one of: a) the ability of isomerising xylose to xylulose; and, b) the ability to convert L-arabinose into D-xylulose 5-phosphate. For a) the yeast cell preferably has a functional exogenous xylose isomerase gene, which gene confers to the yeast cell the ability to isomerise xylose into xylulose. For b) the yeast cell preferably has functional exogenous genes coding for a L-arabinose isomerase, a L-ribulokinase and a L-ribulose-5-phosphate 4-epimerase, which genes together confers to the yeast cell the ability to isomerise convert L-arabinose into D-xylulose 5-phosphate.

Fungal host cells having the ability of isomerising xylose to xylulose as e.g. described in WO 03/0624430 and in WO 06/009434. The ability of isomerising xylose to xylulose is preferably conferred to the yeast cell by transformation with a nucleic acid construct comprising a nucleotide sequence encoding a xylose isomerase. Preferably the yeast cell thus acquires the ability to directly isomerise xylose into xylulose. More preferably the yeast cell thus acquires the ability to grow aerobically and/or anaerobically on xylose as sole energy and/or carbon source though direct isomerisation of xylose into xylulose (and further metabolism of xylulose). It is herein understood that the direct isomerisation of xylose into xylulose occurs in a single reaction catalysed by a xylose isomerase, as opposed to the two step conversion of xylose into xylulose via a xylitol intermediate as catalysed by xylose reductase and xylitol dehydrogenase, respectively.

Several xylose isomerases (and their amino acid and coding nucleotide sequences) that may be successfully used to confer to the yeast cell of the invention the ability to directly isomerise xylose into xylulose have been described in the art. These include the xylose isomerases of *Piromyces* sp. and of other anaerobic fungi that belongs to the families Neocallimastix, Caecomyces, Piromyces or Ruminomyces (WO 03/0624430), *Cyllamyces aberensis* (US 20060234364), *Orpinomyces* (Madhavan et al., 2008, DOI 10.1007/s00253-008-1794-6), the xylose isomerase of the bacterial genus *Bacteroides*, including e.g. *B. thetaiotaomicron* (WO 06/009434), *B. fragilis*, and *B. uniformis* (WO 09/109633), the xylose isomerase of the anaerobic bacterium *Clostridium phytofermentans* (Brat et al., 2009, Appl. Environ. Microbiol. 75:2304-2311), and the xylose isomerases of *Clostridium difficile, Ciona intestinales* and *Fusobacterium mortiferum* (WO 10/074577).

Fungal host cells having the ability to convert L-arabinose into D-xylose 5-phosphate as e.g. described in Wisselink et al. (2007, Appl. Environ. Microbiol. doi:10.1128/AEM.00177-07) and in EP 1 499 708. The ability of to converting L-arabinose into D-xylose 5-phosphate is preferably conferred to the yeast cell by transformation with a nucleic acid construct(s) comprising nucleotide sequences encoding a) an arabinose isomerase; b) a ribulokinase, preferably a L-ribulokinase a xylose isomerase; and c) a ribulose-5-P-4-epimerase, preferably a L-ribulose-5-P-4-epimerase. Preferably, in the yeast cells of the invention, the ability to convert L-arabinose into D-xylose 5-phosphate is the ability to convert L-arabinose into D-xylose 5-phosphate through the subsequent reactions of 1) isomerisation of arabinose into ribulose; 2) phosphorylation of ribulose to ribulose 5-phosphate; and, 3) epimerisation of ribulose 5-phosphate into D-xylulose 5-phosphate. Suitable nucleotide sequences encoding arabinose isomerases, a ribulokinases and ribulose-5-P-4-epimerases may be obtained from *Bacillus subtilis, Escherichia coli* (see e.g. EP 1 499 708), *Lactobacilli*, e.g. *Escherichia coli* (see e.g. Wisselink et al. supra; WO2008/041840), or species of *Clavibacter. Arthrobacter* and *Gramella*, of which preferably Clavibacter *michiganensis, Arthrobacter aurescens* and *Gramella forsetii* (see WO2009/011591).

The transformed cell of the invention further preferably comprises xylulose kinase activity so that xylulose isomerised from xylose may be metabolised to pyruvate. Preferably, the yeast cell contains endogenous xylulose kinase activity. More preferably, a cell of the invention comprises a genetic modification that increases the specific xylulose kinase activity. Preferably the genetic modification causes overexpression of a xylulose kinase, e.g. by overexpression of a nucleotide sequence encoding a xylulose kinase. The gene encoding the xylulose kinase may be endogenous to the yeast cell or may be a xylulose kinase that is heterologous to the yeast cell. A nucleotide sequence that may be used for overexpression of xylulose kinase in the yeast cells of the invention is e.g. the xylulose kinase gene from *S. cerevisiae* (XKS1) as described by Deng and Ho (1990, Appl. Biochem. Biotechnol. 24-25: 193-199). Another preferred xylulose kinase is a xylose kinase that is related to the xylulose kinase from *Piromyces* (xyIB; see WO 03/0624430). This *Piromyces* xylulose kinase is actually more related to prokaryotic kinase than to all of the known eukaryotic kinases such as the yeast kinase. The eukaryotic xylulose kinases have been indicated as non-specific sugar kinases, which have a broad substrate range that includes xylulose. In contrast, the prokaryotic xylulose kinases, to which the *Piromyces* kinase is most closely related, have been indicated to be more specific kinases for xylulose, i.e. having a narrower substrate range. In the yeast cells of the invention, a xylulose kinase to be overexpressed is overexpressed by at least a factor 1.1, 1.2, 1.5, 2, 5, 10 or 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

A cell of the invention further preferably comprises a genetic modification that increases the flux of the pentose phosphate pathway as described in WO 06/009434. In an embodiment, the genetic modification comprises overexpression of at least one enzyme of the (non-oxidative part) pentose phosphate pathway. Preferably the enzyme is selected from the group consisting of the enzymes encoding for ribulose-5-phosphate isomerase, ribulose-5-phosphate 3-epimerase, transketolase and transaldolase.

A further preferred cell of the invention comprises a genetic modification that reduces unspecific aldose reductase activity in the yeast cell. Preferably, unspecific aldose reductase activity is reduced in the host cell by one or more genetic modifications that reduce the expression of or inactivates a gene encoding an unspecific aldose reductase. Preferably, the genetic modifications reduce or inactivate the expression of each endogenous copy of a gene encoding an unspecific aldose reductase that is capable of reducing an aldopentose, including, xylose, xylulose and arabinose, in the yeast cell's genome. A given cell may comprise multiple copies of genes encoding unspecific aldose reductases as a result of di-, poly- or aneuploidy, and/or a cell may contain several different (iso)enzymes with aldose reductase activity that differ in amino acid sequence and that are each encoded by a different gene. Also in such instances preferably the expression of each gene that encodes an unspecific aldose reductase is reduced or inactivated. Preferably, the gene is inactivated by deletion of at least part of the gene or by disruption of the gene, whereby in this context the term gene also includes any non-coding sequence up- or down-stream of the coding sequence, the (partial) deletion or inactivation of which results in a reduction of expression of unspecific aldose reductase activity in the host cell. A nucleotide sequence encoding an aldose reductase whose activity is to be reduced in the yeast cell of the invention and amino acid sequences of such aldose reductases are described in WO 06/009434 and include e.g. the (unspecific) aldose reductase genes of *S. cerevisiae* GRE3 gene (Träff et al., 2001, Appl. Environm. Microbiol. 67: 5668-5674) and orthologues thereof in other species.

In an embodiment, the yeast cell according to the invention may comprise further genetic modifications that result in one or more of the characteristics selected from the group consisting of (a) increased transport of xylose and/or arabinose into the yeast cell; (b) decreased sensitivity to catabolite repression; (c) increased tolerance to ethanol, osmolarity or organic acids; and, (d) reduced production of by-products. By-products are understood to mean carbon-containing molecules other than the desired fermentation product and include e.g. xylitol, arabinitol, glycerol and/or acetic acid. Any genetic modification described herein may be introduced by classical mutagenesis and screening and/or selection for the desired mutant, or simply by screening and/or selection for the spontaneous mutants with the desired characteristics. Alternatively, the genetic modifications may consist of overexpression of endogenous genes and/or the inactivation of endogenous genes. Genes the overexpression of which is desired for increased transport of arabinose and/or xylose into the yeast cell are preferably chosen form genes encoding a hexose or pentose transporter. In *S. cerevisiae* and other yeasts these genes include HXT1, HXT2, HXT3, HXT4, HXT5, HXT7 and GAL2, of which HXT7, HXT5 and GAL2 are most preferred (see Sedlack and Ho, Yeast 2004; 21: 671-684). Another preferred transporter for expression in yeast is the glucose transporter encoded by the *P. stipitis* SUT1 gene (Katahira et al., 2008, Enzyme Microb. Technol. 43: 115-119). Similarly orthologues of these transporter genes in other species may be overexpressed. Other genes that may be overexpressed in the yeast cells of the invention include genes coding for glycolytic enzymes and/or ethanologenic enzymes such as alcohol dehydrogenases. Preferred endogenous genes for inactivation include hexose kinase genes e.g. the *S. cerevisiae* HXK2 gene (see Diderich et al., 2001, Appl. Environ. Microbiol. 67: 1587-1593); the *S. cerevisiae* MIG1 or MIG2 genes; genes coding for enzymes involved in glycerol metabolism such as the *S. cerevisiae* glycerol-phosphate dehydrogenase 1 and/or 2 genes; or (hybridising) orthologues of these genes in other species. Other preferred further modifications of host cells for xylose fermentation are described in van Maris et al. (2006, Antonie van Leeuwenhoek 90:391-418), WO2006/009434, WO2005/023998, WO2005/111214, and WO2005/091733. Any of the genetic modifications of the yeast cells of the invention as described herein are, in as far as possible, preferably introduced or modified by self-cloning genetic modification.

A preferred host cell according to the invention has the ability to grow on at least one of xylose and arabinose as carbon/energy source, preferably as sole carbon/energy source, and preferably under anaerobic conditions, i.e. conditions as defined herein below for anaerobic fermentation process. Preferably, when grown on xylose as carbon/energy source the host cell produces essentially no xylitol, e.g. the xylitol produced is below the detection limit or e.g. less than 5, 2, 1, 0.5, or 0.3% of the carbon consumed on a molar basis. Preferably, when grown on arabinose as carbon/energy source, the yeast cell produces essentially no arabinitol, e.g. the arabinitol produced is below the detection limit or e.g. less than 5, 2, 1, 0.5, or 0.3% of the carbon consumed on a molar basis.

A preferred cell of the invention has the ability to grow on at least one of a hexose, a pentose, glycerol, acetic acid and combinations thereof at a rate of at least 0.01, 0.02, 0.05, 0.1, 0.2, 0.25 or 0.3 $h^{-1}$ under aerobic conditions, or, more preferably, at a rate of at least 0.005, 0.01, 0.02, 0.05, 0.08, 0.1, 0.12, 0.15 or 0.2 $h^{-1}$ under anaerobic conditions. Therefore, preferably the host cell has the ability to grow on at least one of xylose and arabinose as sole carbon/energy source at a rate of at least 0.01, 0.02, 0.05, 0.1, 0.2, 0.25 or 0.3 $h^{-1}$ under aerobic conditions, or, more preferably, at a rate of at least 0.005, 0.01, 0.02, 0.05, 0.08, 0.1, 0.12, 0.15 or 0.2 $h^{-1}$ under anaerobic conditions. More preferably, the host cell has the ability to grow on a mixture of a hexose (e.g. glucose) and at least one of xylose and arabinose (in a 1:1 weight ratio) as sole carbon/energy source at a rate of at least 0.01, 0.02, 0.05, 0.1, 0.2, 0.25 or 0.3 $h^{-1}$ under aerobic conditions, or, more preferably, at a rate of at least 0.005, 0.01, 0.02, 0.05, 0.08, 0.1, 0.12, 0.15 or 0.2 $h^{-1}$ under anaerobic conditions. Most preferably, the host cell has the ability to grow on a mixture of a hexose (e.g. glucose), at least one of xylose and arabinose and glycerol (in a 1:1:1 weight ratio) as sole carbon/energy source at a rate of at least 0.01, 0.02, 0.05, 0.1, 0.2, 0.25 or 0.3 $h^{-1}$ under aerobic conditions, or, more preferably, at a rate of at least 0.005, 0.01, 0.02, 0.05, 0.08, 0.1, 0.12, 0.15 or 0.2 $h^{-1}$ under anaerobic conditions.

Over the years suggestions have been made for the introduction of various organisms for the production of bio-ethanol from crop sugars. In practice, however, all major bio-ethanol production processes have continued to use the yeasts of the genus *Saccharomyces* as ethanol producer. This is due to the many attractive features of *Saccharomyces* species for industrial processes, i. e., a high acid-, ethanol- and osmo-tolerance, capability of anaerobic growth, and of course its high alcoholic fermentative capacity. Preferred yeast species as host cells include *S. cerevisiae*, *S. bulderi*, *S. bametti*, *S. exiguus*, *S. uvarum*, *S. diastaticus*, *K. lactis*, *K. marxianus* or *K. fragilis*.

A yeast cell of the invention may be able to convert plant biomass, celluloses, hemicelluloses, pectins, rhamnose, galactose, frucose, maltose, maltodextrines, ribose, ribulose, or starch, starch derivatives, sucrose, lactose and glycerol, for example into fermentable sugars. Accordingly, a cell of the invention may express one or more enzymes such as a cellulase (an endocellulase or an exocellulase), a hemicellulase (an endo- or exo-xylanase or arabinase) necessary for the conversion of cellulose into glucose monomers and hemicellulose into xylose and arabinose monomers, a pectinase able to convert pectins into glucuronic acid and galacturonic acid or an amylase to convert starch into glucose monomers.

The yeast cell further preferably comprises those enzymatic activities required for conversion of pyruvate to a desired fermentation product, such as ethanol, butanol, lactic acid, 3-hydroxy-propionic acid, acrylic acid, acetic acid, succinic acid, citric acid, fumaric acid, malic acid, itaconic acid, an amino acid, 1,3-propane-diol, ethylene, glycerol, a β-lactam antibiotic or a cephalosporin.

A preferred cell of the invention is a cell that is naturally capable of alcoholic fermentation, preferably, anaerobic alcoholic fermentation. A cell of the invention preferably has a high tolerance to ethanol, a high tolerance to low pH (i.e. capable of growth at a pH lower than about 5, about 4, about 3, or about 2.5) and towards organic acids like lactic acid, acetic acid or formic acid and/or sugar degradation products such as furfural and hydroxy-methylfurfural and/or a high tolerance to elevated temperatures.

Any of the above characteristics or activities of a cell of the invention may be naturally present in the yeast cell or may be introduced or modified by genetic modification.

A cell of the invention may be a cell suitable for the production of ethanol. A cell of the invention may, however, be suitable for the production of fermentation products other than ethanol. Such non-ethanolic fermentation products include in principle any bulk or fine chemical that is producible by a eukaryotic microorganism such as a yeast or a filamentous fungus.

The fermentation process is preferably run at a temperature that is optimal for the yeast cell. Thus, for most yeasts or fungal host cells, the fermentation process is performed at a temperature which is less than about 42° C., preferably less than about 38° C. For yeast or filamentous fungal host cells, the fermentation process is preferably performed at a temperature which is lower than about 35, about 33, about 30 or about 28° C. and at a temperature which is higher than about 20, about 22, or about 25° C.

The ethanol yield on xylose and/or glucose in the process preferably is at least about 50, about 60, about 70, about 80, about 90, about 95 or about 98%. The ethanol yield is herein defined as a percentage of the theoretical maximum yield.

The invention also relates to a process for producing a fermentation product.

The fermentation processes may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity.

The fermentation process according to the present invention may be run under aerobic and anaerobic conditions. Preferably, the process is carried out under micro-aerophilic or oxygen limited conditions.

An anaerobic fermentation process is herein defined as a fermentation process run in the absence of oxygen or in which substantially no oxygen is consumed, preferably less than about 5, about 2.5 or about 1 mmol/L/h, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6, such as at least 7 mmol/L/h. A process of the invention comprises recovery of the fermentation product.

For the recovery of the fermentation product existing technologies are used. For different fermentation products different recovery processes are appropriate. Existing methods of recovering ethanol from aqueous mixtures commonly use fractionation and adsorption techniques. For example, a beer still can be used to process a fermented product, which contains ethanol in an aqueous mixture, to produce an enriched ethanol-containing mixture that is then subjected to fractionation (e.g., fractional distillation or other like techniques). Next, the fractions containing the highest concentrations of ethanol can be passed through an adsorber to remove most, if not all, of the remaining water from the ethanol.

All patent and literature references cited in the present specification are hereby incorporated by reference in their entirety.

The following examples are offered for illustrative purposes only, and are not intended to limit the scope of the present invention in any way.

EXAMPLES

In order to improve the anaerobic (co-)conversion of glycerol and acetic acid both in terms of rate and amount, alternative gene combinations were tested. For a number of enzymes in the pathway, i.e. glycerol dehydrogenase, dihydroxyacetone kinase and acetaldehyde dehydrogenase, multiple alternative genes were tested that could further enhance the ability of the yeast strain to convert glycerol and acetic acid, next to pentose and hexose sugars, into ethanol under anaerobic conditions.

The selected enzyme candidates are given in table 8.

TABLE 8

Selected enzyme candidates, encoding desired enzyme activities and reference to the protein sequence (SEQ ID NO's are given in the table)

| Gene | Source organism | Enzyme activity | SEQ ID NO: |
|---|---|---|---|
| adhE | *Escherichia coli* | Bifunctional acetaldehyde-CoA/alcohol dehydrogenase | 1 |

TABLE 8-continued

Selected enzyme candidates, encoding desired enzyme activities and reference to the protein sequence (SEQ ID NO's are given in the table)

| Gene | Source organism | Enzyme activity | SEQ ID NO: |
|---|---|---|---|
| acdH | *Lactobacillus plantarum* | Acetaldehyde dehydrogenase | 2 |
| eutE | *Escherichia coli* | Ethanolamine utilization protein | 3 |
| Lin1129 | *Listeria innocua* | Aldehyde dehydrogenase | 4 |
| adhE | *Staphylococcus aureus* | Bifunctional acetaldehyde-CoA/alcohol dehydrogenase | 5 |
| ACS2 | *Saccharomyces cerevisiae* | Acetyl-CoA ligase | 6 |
| gldA | *Escherichia coli* | Glycerol dehydrogenase | 7 |
| gldA | *Klebsiella pneumoniae* | Glycerol dehydrogenase | 8 |
| gldA | *Enterococcus aerogenes* | Glycerol dehydrogenase | 9 |
| gldA | *Yersinia aldovae* | Glycerol dehydrogenase | 10 |
| DAK1 | *Saccharomyces cerevisiae* | Dihydroxyacetone kinase | 11 |
| dhaK | *Klebsiella pneumonia* | Dihydroxyacetone kinase | 12 |
| DAK1 | *Yarrowia lipolytica* | Dihydroxyacetone kinase | 13 |
| DAK1 | *Schizosaccharomyces pombe* | Dihydroxyacetone kinase | 14 |

The genes were codon-pair-optimized for optimal expression in *S. cerevisiae*, as described in WO 2008/000632. The SEQ ID NO: of the protein sequence is indicated in table 8.

Four categories of genes were defined: A) the AADH-group, consisting of SEQ ID NO:'s 1-5; B) the ACS-group, consisting of SEQ ID NO:6; C) the GLD-group, consisting of SEQ ID NO:'s 7-10 and D) the DAK-group, consisting of SEQ ID NO:'s 11-14.

Expression constructs were made, allowing each gene to be expressed at a high level and at a medium/low level.

For group A, the TDH3- and the TDH1-promoters were chosen (SEQ ID NO:'s 15 and 16, respectively). The terminator of these genes was the PGK1-terminator (SEQ ID NO: 17), in all cases For group B, the PGK1- and the PRE3-promoters were chosen (SEQ ID NO:'s 18 and 19, respectively). The terminator of these genes was the PGI1-terminator (SEQ ID NO: 20), in all cases For group C, the ENO1- and the ACT1-promoters were chosen (SEQ ID NO:'s 21 and 22, respectively). The terminator of these genes was the CYC1-terminator (SEQ ID NO: 23), in all cases.

For group D, the TPI1- and the ATG7-promoters were chosen (SEQ ID NO:'s 24 and 25, respectively). The terminator of these genes was the ENO1-terminator (SEQ ID NO: 26), in all cases.

In total, 28 different expression cassettes were assembled, as indicated in table 9.

TABLE 9

Outline of all assembled expression cassettes (ASS) that were generated in a backbone plasmid vector (see Materials and Methods for details). The first SEQ ID NO: defines the used promoter, the second SEQ ID NO: defines the ORF and the third SEQ ID NO: defines the transcription terminator. The ASS-number is generated for easier reference.

| Group A | SEQ ID NO: 15-SEQ ID NO: 1-SEQ ID NO: 17 | ASS01 |
|---|---|---|
| | SEQ ID NO: 15-SEQ ID NO: 2-SEQ ID NO: 17 | ASS02 |
| | SEQ ID NO: 15-SEQ ID NO: 3-SEQ ID NO: 17 | ASS03 |
| | SEQ ID NO: 15-SEQ ID NO: 4-SEQ ID NO: 17 | ASS04 |
| | SEQ ID NO: 15-SEQ ID NO: 5-SEQ ID NO: 17 | ASS05 |
| | SEQ ID NO: 16-SEQ ID NO: 1-SEQ ID NO: 17 | ASS06 |
| | SEQ ID NO: 16-SEQ ID NO: 2-SEQ ID NO: 17 | ASS07 |

TABLE 9-continued

Outline of all assembled expression cassettes (ASS) that were generated in a backbone plasmid vector (see Materials and Methods for details). The first SEQ ID NO: defines the used promoter, the second SEQ ID NO: defines the ORF and the third SEQ ID NO: defines the transcription terminator. The ASS-number is generated for easier reference.

|  | | | |
|---|---|---|---|
|  | SEQ ID NO: 16-SEQ ID NO: 3-SEQ ID NO: 17 | ASS08 |
|  | SEQ ID NO: 16-SEQ ID NO: 4-SEQ ID NO: 17 | ASS09 |
|  | SEQ ID NO: 16-SEQ ID NO: 5-SEQ ID NO: 17 | ASS10 |
| Group B | SEQ ID NO: 18-SEQ ID NO: 6-SEQ ID NO: 20 | ASS11 |
|  | SEQ ID NO: 19-SEQ ID NO: 6-SEQ ID NO: 20 | ASS12 |
| Group C | SEQ ID NO: 21-SEQ ID NO: 7-SEQ ID NO: 23 | ASS13 |
|  | SEQ ID NO: 21-SEQ ID NO: 8-SEQ ID NO: 23 | ASS14 |
|  | SEQ ID NO: 21-SEQ ID NO: 9-SEQ ID NO: 23 | ASS15 |
|  | SEQ ID NO: 21-SEQ ID NO: 10-SEQ ID NO: 23 | ASS16 |
|  | SEQ ID NO: 22-SEQ ID NO: 7-SEQ ID NO: 23 | ASS17 |
|  | SEQ ID NO: 22-SEQ ID NO: 8-SEQ ID NO: 23 | ASS18 |
|  | SEQ ID NO: 22-SEQ ID NO: 9-SEQ ID NO: 23 | ASS19 |
|  | SEQ ID NO: 22-SEQ ID NO: 10-SEQ ID NO: 23 | ASS20 |
| Group D | SEQ ID NO: 24-SEQ ID NO: 11-SEQ ID NO: 26 | ASS21 |
|  | SEQ ID NO: 24-SEQ ID NO: 12-SEQ ID NO: 26 | ASS22 |
|  | SEQ ID NO: 24-SEQ ID NO: 13-SEQ ID NO: 26 | ASS23 |
|  | SEQ ID NO: 24-SEQ ID NO: 14-SEQ ID NO: 26 | ASS24 |
|  | SEQ ID NO: 25-SEQ ID NO: 11-SEQ ID NO: 26 | ASS25 |
|  | SEQ ID NO: 25-SEQ ID NO: 12-SEQ ID NO: 26 | ASS26 |
|  | SEQ ID NO: 25-SEQ ID NO: 13-SEQ ID NO: 26 | ASS27 |
|  | SEQ ID NO: 25-SEQ ID NO: 14-SEQ ID NO: 26 | ASS28 |

The assembled expression cassettes (ASS) were amplified by PCR using primers with connectors at each flank, as depicted in FIG. 2. The PCR-product is designated a CAS. The CAS elements overlap partly with either an integration flank and/or another CAS and/or a selectable marker, allowing upon introduction in competent yeast cells recombination of the genetic elements into the genome of the transformation competent yeast strain, as depicted in FIG. 2.

In a multifactoial pathway design, all possible combinations of the individual members of the four categories (group A, B, C and D) were combined, using the technology described in patent application PCT/EP2013/056623. All 1280 different possible combinations of expression cassettes were generated and used to transform strain RN1069, a gpd1gpd2 double deletion strain (see Material and Methods).

As depicted in FIG. 2, an antibiotic resistance marker was included in the multifactorial pathway design, in order to enable selection of yeast transformants that had successfully integrated the desired pathway into their genome by recombination. The sequence of the selection marker is given as SEQ ID NO: 27.

In addition, two integration flanks, designated 5'-INT1 and 3'-INT1 in FIG. 2, were included in the transformation mixture. The sequences of these two flanking regions are generated in a PCR reaction using genomic DNA of the host strain as template and primer combination SEQ ID NO: 30 and 31 for the 5'-flank of INT1 (FIG. 2) and primer combination SEQ ID NO: 42 and 43 for the 3'-INT1 flank (FIG. 2).

Materials and Methods
General Molecular Biology Techniques

Unless indicated otherwise, the methods used are standard biochemical techniques. Examples of suitable general methodology textbooks include Sambrook et al., Molecular Cloning, a Laboratory Manual (1989) and Ausubel et al., Current Protocols in Molecular Biology (1995), John Wiley & Sons, Inc.

Media

The media used in the experiments was either YEP-medium (10 g/l yeast extract, 20 g/l peptone) or solid YNB-medium (6.7 g/l yeast nitrogen base, 15 g/l agar), supplemented with sugars as indicated in the examples. For solid YEP medium, 15 g/l agar was added to the liquid medium prior to sterilization.

In the anaerobic screening experiment. Mineral Medium was used. The composition of Mineral Medium has been described by Verduyn et al. (Yeast (1992), Volume 8, 501-517). The use of ammoniumsulfate was however omitted; instead, as a nitrogen source, 2.3 g/l urea was used. In addition, ergosterol (0.01 g/L), Tween80 (0.42 g/L) and sugars (as indicated) were added.

Transformants of strain RN1069 (by integration of DNA constructs) are histidine auxotrophic.

Strains

The strains used in the experiments were RN1041 and RN1069. RN1041 has been described in WO 2012/067510. This strain has the following genotype:

MAT a, ura3-52, leu2-112, his3::loxP, gre3::loxP, loxP-pTPI1::TAL1, loxP-pTPI1::RKI1, loxP-pTPI1-TKL1, loxP-pTPI1-RPE1, delta::pADH1-XKS1-tCYC1-LEU2, delta::URA3-pTPI1-xylA-tCYC1

MAT a=mating type a ura3-52, leu2-112, HIS3::loxP mutations in the URA3, LEU2 and HIS3 genes respectively. The ura3-52 mutation is complemented by the URA3 gene on the *Piromyces* xylA overexpression construct; the leu2-112 mutation is complemented by the LEU2 gene on the XKS1 overexpression construct. The deletion of the HIS3-gene causes a histidine auxotrophy. For this reason, RN1041 needs histidine in the medium for growth.

gre3::loxP is a deletion of the GRE3 gene, encoding aldose reductase. The loxP site is left behind in the genome after marker removal.

loxP-pTPI1 designates the overexpression of genes of, in the experiments described herein, the non-oxidative pentose phosphate pathway by replacement of the native promoter by the promoter of the TPI1 gene. The loxP site upstream of the strong, constitutive TPI1 promoter remains in the genome after marker removal (Kuyper et al, FEMS Yeast Research 5 (2005) 925-934).

delta:: means chromosomal integration of the construct after recombination on the long terminal repeats of the Ty1 retrotransposon.

Strain RN1001 is the parent strain of strain RN1041, i.e. before deletion of the HIS3-gene.

Strain RN1069 is derived from RN1041: the GPD1 and GPD2 genes were disrupted by gene replacement. To this end, dominant antibiotic resistance markers, flanked by sequences homologous to the sequences just beside the open reading frame (ORF) of GPD1 or GPD2, were constructed by PCR and used to transform strain RN1041. These gene disruption cassettes have been included in the sequence listing as SEQ ID NO: 28 and 29 respectively. The construction of strain RN1069 is also described in detail in WO2013/081456. The genotype of strain RN1069 is: MAT a, ura3-52, leu2-112, his3::loxP, gre3::loxP, loxP-pTPI1::TAL1, loxP-pTPI1::RKI1, loxP-pTPI1-TKL1, loxP-pTPI1-RPE1, delta::pADH1-XKS1-tCYC1-LEU2, delta::URA3-pTPI1-xylA-tCYC1 gpd1::hphMX, gpd2::natMX.

Strain RN1189 was used as a reference strain. Strain RN1189 is described in WO2013/081456. In short, strain RN1189 was constructed by transformation of strain RN1069 with plasmid pRN977. Plasmid pRN977 is a 2μ plasmid and contains the following features: the HIS3-gene for selection of transformants, the ampicillin resistance marker for selection in *E. coli*, the adhE-gene from *E. coli* under control of the PGK1-promoter and the ADH1-terminator, the DAK1-gene from *S. cerevisiae* under control of the TPI1-promoter and the PGI1-terminator and the *E. coli* gldA-gene, under control of the ACT1-promoter and CYC1-terminator. All promoters and terminators are from *S. cerevisiae*.

Strain Construction

The strain construction approach is described in patent application PCT/EP2013/056623. It describes the techniques enabling the construction of expression cassettes from various genes of interest in such a way, that these cassettes are combined into a pathway and integrated in a specific locus of the yeast genome upon transformation of this yeast. A schematic representation is depicted in FIG. 2.

Firstly, an integration site in the yeast genome is chosen (e.g. INT1). A DNA fragment of approximately 500 bp of the up- and downstream part of the integration locus is amplified using PCR, flanked by a connector. These connectors are 50 bp sequences that allow for correct in vivo recombination of the pathway upon transformation in yeast (Saccharomyces cerevisiae e.g.). The genes of interest, as well as a selectable resistance marker (e.g. kanMX), are generated by PCR, incorporating a different connector at each flank, as is displayed in FIG. 2. Upon transformation of yeast cells with the DNA fragments, in vivo recombination and integration into the genome takes place at the desired location. This technique allows for pathway tuning, as one or more genes from the pathway can be replaced with (an)other gene(s) or genetic element(s), as long as that the connectors that allow for homologous recombination remain constant (patent application PCT/EP2013/056623).

Expression Cassette Construction

The open reading frames (ORFs), promoter sequences and terminators were synthesized at DNA 2.0 (Menlo Park, Calif. 94025, USA). The sequences of these genetic elements are listed as SEQ ID NO:'s 1 until and including 26. The promoter, ORF and terminator sequences were assembled by using the Golden Gate technology, as described by Engler et al (2011) and references therein. The assembled expression cassettes were ligated into Bsal-digested backbone vectors; group A (table 2) into p5Abbn (SEQ ID NO: 44), group B (table 2) into pBCbbn (SEQ ID NO: 45), group C (table 2) into pCDbbn (SEQ ID NO: 46) and group D (table 2) into pD3bbn (SEQ ID NO: 47).

Expression Cassette Amplification

The assembled expression cassettes that were generated as described above (section "Expression cassette construction"), the integration flanks and the selective marker were amplified by PCR using the primers described as SEQ ID NO:'s 30-43 (see below). The kanMX-marker, as G418 resistance marker for selection in yeast, was amplified from a plasmid containing this marker. The sequence of the marker is described as SEQ ID NO: 27.

The INT1-flanks were amplified from genomic DNA from strain CEN.PK113-7D using the SEQ ID NO:'s 30 and 31 (5'-INT1 flank) and 42 and 43 (3'-INT1 flank).

TABLE 10

Overview of primers use to amplify CAS (expression cassettes with overlapping sequences for homologous recombination in yeast) from ASS (assembled expression cassettes). The corresponding number are used (e.g. CAS01 is from ASS01).

| CAS | Element | Forward primer | Reverse primer |
|---|---|---|---|
| — | 5'-INT1 (SEQ ID NO: 28) | SEQ ID NO: 30 | SEQ ID NO: 31 |
| CAS01-CAS10 | AADH in p5Abbn | SEQ ID NO: 32 | SEQ ID NO: 33 |
| — | marker (SEQ ID NO: 27) | SEQ ID NO: 34 | SEQ ID NO: 35 |
| CAS11-CAS12 | ACS in pBCbbn | SEQ ID NO: 36 | SEQ ID NO: 37 |
| CAS13-CAS20 | GLDA in pCDbbn | SEQ ID NO: 38 | SEQ ID NO: 39 |
| CAS21-CAS28 | DAK in pD3bbn | SEQ ID NO: 40 | SEQ ID NO: 41 |
| — | 3'-INT1 (SEQ ID NO: 29) | SEQ ID NO: 42 | SEQ ID NO: 43 |

Transformation of Yeast Cells

Yeast transformation was done according to the method described by Schiestl and Gietz (Current Genetics (1989), Volume 16, 339-346).

Anaerobic Growth Experiments in Microolates

Growth experiments were performed in flat bottom NUNC microplates (MTPs). 275 µl of medium was filled out in each well. The composition of the medium was as follows:
Mineral medium (based on Verduyn et al (1992), urea instead of ammoniumsulfate)
2% glucose
2% xylose
1% glycerol
2 g/l acetic acid
200 µg/ml histidine (in case of strain RN1069 and derivatives, which are his3::loxP) pH 4.5

All MTPs were sealed with an aluminum seal. The MTPs were then placed in the anaerobic incubator (Infors). After 48 hours of growth, the MTPs were removed from the anaerobic Infors. The plates were then spun down 10 minutes @2750 rpm in a microplate centrifuge. 150 µl of the supernatant was then transferred to a MTP suitable for NMR analysis.

NMR analysis

For the quantification of glucose, xylose, glycerol, acetic acid and ethanol in the sample, 150 µl sample is transferred accurately into a suitable vial. Subsequently 100 µl internal standard solution, containing maleic acid (20 g/l), EDTA (40 g/l) and trace amounts of DSS (4,4-dimethyl-4-silapentane-1-sulfonic acid) in $D_2O$, and 450 µL $D_2O$ is added.

1D $^1H$ NMR spectra are recorded on a Bruker Avance III 700 MHz, equipped with a cryo-probe, using a pulse program with water suppression (power corresponding to 3 Hz) at a temperature of 27° C.

The analyte concentrations are calculated based on the following signals (5 relative to DSS):
α-glucose peak at 5.22 ppm (d, 0.38H, J=4 Hz),
α-xylose peak at 5.18 ppm (d, 0.37H, J=4 Hz),
glycerol peak at 3.55 ppm (dd, 2H, $J_{1,2}$=6 Hz and $J_{1a,1b}$=12 Hz)
acetic acid peak at 1.91 ppm (s, 3H)
ethanol peak at 1.17 ppm (t, 3H, J=7 Hz)
The signal user for the standard:
Maleic acid peak at 6.05 ppm (s, 2H)

Example 1

Construction of the Full Combinatorial Array of Yeast Transformants

The full combinatorial array of strains was constructed as described above. To this end, strain RN1069 was transformed with all 1280 mixes of genes (vide supra). Transformation mixes were plated on YEP-agar containing 20 g glucose per liter and 200 µg G418/ml.

From each transformation, two independent transformants were selected and transferred to YEPD agar in microplates (one colony per well). On each microplate, a reference strains was inoculated as well: RN1189.

Example 2

Growth Experiment and Analysis of the Results

The array of selected colonies and strains (Example 1) was tested in the experimental set-up described in the Material and Methods.

In short, the strains in the microplate with YEPD-agar were used to inoculate, 275 µl Mineral Medium containing 200 µg histidine per ml, 2% glucose, 2% xylose, 1% glycerol and 2 g/l acetic acid, in microplates. The pH of the medium was set at 4.5, below the pKa of acetic acid. The microplate was sealed and incubated for 48 hours under anaerobic conditions. Cells were spun down by centrifugation and the supernatant was analyzed by NMR. The top 150 results are given in table 11.

TABLE 11

Results of the growth experiments of the 150 best strains (top 150). In the first two columns the identification of the strain experiments is given. In columns 3-6, the construct of the strain is given, for AADH, ACS, GLDA and DAK1. Columns 7-11 indicates the results of the fermentation, concentrations (g/l) of glucose, xylose, glycerol, acetate and ethanol, respectively. Columns 12-14 give the ranking of strains for each product (glycerol and acetate consumption) and ethanol production. Column 15 gives total ranking based on the rankings in column 12-14.

| Num | Expno | AADH | ACS | GLDA | DAK1 | glucose | xylose | glycerol | acetate | ethanol | Glycerol Rank | Acetate Rank | EtOH Rank | Total Rank |
|---|---|---|---|---|---|---|---|---|---|---|---|---|---|---|
| 355 | 67 | CAS2 | CAS11 | CAS13 | CAS21 | 0.0 | 0.8 | 7.0 | 0.3 | 18.9 | 2 | 2 | 11 | 1 |
| 1131 | 75 | CAS5 | CAS11 | CAS15 | CAS24 | 0.1 | 2.1 | 7.6 | 0.5 | 18.4 | 27 | 12 | 20 | 2 |
| 820 | 52 | CAS3 | CAS12 | CAS18 | CAS23 | 0.1 | 1.1 | 7.8 | 0.4 | 18.2 | 41 | 3 | 17 | 3 |
| 386 | 2 | CAS2 | CAS11 | CAS15 | CAS21 | 0.1 | 2.2 | 7.3 | 0.4 | 17.2 | 5 | 4 | 54 | 4 |
| 354 | 66 | CAS2 | CAS11 | CAS13 | CAS21 | 0.1 | 1.1 | 7.6 | 0.6 | 18.5 | 23 | 30 | 14 | 5 |
| 1696 | 64 | CAS7 | CAS12 | CAS15 | CAS23 | 0.1 | 2.0 | 7.6 | 0.6 | 18.6 | 22 | 28 | 18 | 6 |
| 787 | 19 | CAS3 | CAS12 | CAS16 | CAS23 | 0.1 | 0.5 | 7.8 | 0.5 | 18.3 | 51 | 7 | 13 | 7 |
| 1130 | 74 | CAS5 | CAS11 | CAS15 | CAS24 | 0.1 | 3.8 | 7.4 | 0.7 | 21.5 | 10 | 54 | 8 | 8 |
| 519 | 39 | CAS2 | CAS12 | CAS15 | CAS23 | 0.1 | 2.9 | 7.3 | 0.6 | 17.8 | 4 | 32 | 42 | 9 |
| 2571 | 75 | CAS2 | CAS11 | CAS19 | CAS25 | 0.2 | 2.0 | 7.6 | 0.6 | 17.4 | 24 | 26 | 33 | 10 |
| 520 | 40 | CAS2 | CAS12 | CAS15 | CAS23 | 0.1 | 1.5 | 7.6 | 0.6 | 18.0 | 26 | 38 | 21 | 11 |
| 608 | 32 | CAS3 | CAS11 | CAS13 | CAS21 | 0.1 | 2.4 | 7.4 | 0.4 | 16.9 | 7 | 6 | 73 | 12 |
| 522 | 42 | CAS2 | CAS12 | CAS15 | CAS24 | 0.1 | 1.1 | 7.6 | 0.6 | 17.7 | 21 | 43 | 23 | 13 |
| 1682 | 50 | CAS7 | CAS12 | CAS14 | CAS23 | 0.1 | 2.6 | 7.4 | 0.7 | 18.2 | 11 | 50 | 28 | 14 |
| 1697 | 65 | CAS7 | CAS12 | CAS15 | CAS24 | 0.1 | 1.6 | 7.7 | 0.6 | 18.6 | 30 | 44 | 15 | 14 |
| 359 | 71 | CAS2 | CAS11 | CAS13 | CAS23 | 0.1 | 2.9 | 7.1 | 0.5 | 16.7 | 3 | 10 | 86 | 16 |
| 1098 | 42 | CAS5 | CAS11 | CAS13 | CAS21 | 0.1 | 1.4 | 7.5 | 0.5 | 16.3 | 15 | 9 | 77 | 17 |
| 632 | 56 | CAS3 | CAS11 | CAS14 | CAS24 | 0.1 | 2.0 | 7.4 | 0.6 | 16.8 | 12 | 23 | 68 | 18 |
| 1119 | 63 | CAS5 | CAS11 | CAS14 | CAS24 | 0.1 | 3.1 | 7.8 | 0.6 | 17.8 | 46 | 19 | 46 | 19 |
| 614 | 38 | CAS3 | CAS11 | CAS13 | CAS24 | 0.1 | 1.3 | 7.9 | 0.6 | 17.6 | 57 | 31 | 27 | 20 |
| 506 | 26 | CAS2 | CAS12 | CAS14 | CAS24 | 0.1 | 2.3 | 7.6 | 0.6 | 17.4 | 28 | 45 | 50 | 21 |
| 739 | 67 | CAS3 | CAS12 | CAS13 | CAS23 | 0.1 | 2.4 | 7.7 | 0.6 | 16.8 | 35 | 20 | 74 | 22 |
| 1677 | 45 | CAS7 | CAS12 | CAS14 | CAS21 | 0.1 | 1.4 | 7.8 | 0.7 | 17.3 | 47 | 55 | 31 | 23 |
| 1539 | 3 | CAS7 | CAS11 | CAS13 | CAS23 | 0.1 | 4.4 | 7.5 | 0.6 | 17.4 | 14 | 27 | 96 | 24 |
| 784 | 16 | CAS3 | CAS12 | CAS16 | CAS21 | 0.1 | 1.6 | 8.1 | 0.6 | 18.2 | 100 | 21 | 19 | 25 |
| 1695 | 63 | CAS7 | CAS12 | CAS15 | CAS23 | 0.1 | 4.4 | 7.6 | 0.6 | 17.2 | 18 | 37 | 103 | 26 |
| 2263 | 55 | CAS9 | CAS11 | CAS14 | CAS24 | 0.1 | 1.6 | 7.7 | 0.6 | 16.0 | 36 | 29 | 94 | 27 |
| 2452 | 52 | CAS10 | CAS12 | CAS15 | CAS21 | 0.1 | 3.8 | 7.5 | 0.6 | 16.6 | 17 | 22 | 134 | 28 |
| 1043 | 83 | CAS4 | CAS12 | CAS16 | CAS21 | 0.1 | 1.3 | 8.0 | 0.7 | 17.6 | 88 | 64 | 26 | 29 |
| 630 | 54 | CAS3 | CAS11 | CAS14 | CAS23 | 0.0 | 1.6 | 8.0 | 0.7 | 17.3 | 79 | 63 | 37 | 30 |
| 1707 | 75 | CAS7 | CAS12 | CAS16 | CAS21 | 0.1 | 3.8 | 7.8 | 0.7 | 17.9 | 53 | 73 | 57 | 31 |
| 641 | 65 | CAS3 | CAS11 | CAS15 | CAS21 | 0.0 | 2.1 | 7.9 | 0.7 | 17.4 | 71 | 70 | 47 | 32 |
| 615 | 39 | CAS3 | CAS11 | CAS13 | CAS24 | 0.1 | 3.2 | 7.9 | 0.7 | 16.7 | 56 | 60 | 95 | 33 |
| 214 | 22 | CAS1 | CAS12 | CAS13 | CAS23 | 0.2 | 4.9 | 6.3 | 0.3 | 16.5 | 1 | 1 | 211 | 34 |
| 1233 | 81 | CAS5 | CAS12 | CAS15 | CAS21 | 0.1 | 4.1 | 7.4 | 0.5 | 16.2 | 8 | 13 | 198 | 35 |
| 358 | 70 | CAS2 | CAS11 | CAS13 | CAS23 | 0.1 | 2.6 | 7.9 | 0.8 | 17.1 | 62 | 98 | 67 | 36 |
| 1252 | 4 | CAS5 | CAS12 | CAS16 | CAS23 | 0.1 | 4.2 | 8.0 | 0.6 | 17.3 | 89 | 48 | 93 | 37 |
| 488 | 8 | CAS2 | CAS12 | CAS13 | CAS23 | 0.1 | 2.3 | 7.8 | 0.6 | 15.6 | 40 | 40 | 152 | 38 |
| 1105 | 49 | CAS5 | CAS11 | CAS13 | CAS24 | 0.1 | 2.2 | 8.2 | 0.8 | 26.0 | 139 | 93 | 1 | 39 |
| 1540 | 4 | CAS7 | CAS11 | CAS13 | CAS23 | 0.1 | 3.5 | 7.4 | 0.5 | 15.8 | 13 | 15 | 208 | 40 |
| 2564 | 68 | CAS2 | CAS11 | CAS19 | CAS21 | 0.1 | 2.2 | 7.9 | 0.6 | 15.9 | 65 | 46 | 126 | 41 |
| 783 | 15 | CAS3 | CAS12 | CAS16 | CAS21 | 0.2 | 2.6 | 8.3 | 0.7 | 17.6 | 145 | 58 | 36 | 42 |
| 536 | 56 | CAS2 | CAS12 | CAS16 | CAS24 | 0.0 | 2.0 | 8.1 | 0.8 | 17.3 | 105 | 96 | 48 | 43 |
| 2555 | 59 | CAS2 | CAS11 | CAS18 | CAS25 | 0.0 | 1.7 | 7.6 | 0.6 | 14.9 | 19 | 17 | 215 | 44 |
| 500 | 20 | CAS2 | CAS12 | CAS14 | CAS21 | 0.1 | 2.1 | 8.0 | 0.7 | 16.3 | 85 | 82 | 89 | 45 |
| 2187 | 75 | CAS9 | CAS12 | CAS14 | CAS23 | 0.1 | 2.9 | 8.0 | 0.8 | 17.0 | 77 | 104 | 76 | 46 |
| 626 | 50 | CAS3 | CAS11 | CAS14 | CAS21 | 0.1 | 1.9 | 8.2 | 0.7 | 17.0 | 120 | 85 | 53 | 47 |
| 837 | 69 | CAS3 | CAS12 | CAS19 | CAS23 | 0.0 | 0.9 | 8.4 | 0.7 | 18.2 | 184 | 62 | 16 | 48 |
| 535 | 55 | CAS2 | CAS12 | CAS16 | CAS24 | 0.1 | 2.7 | 8.1 | 0.8 | 17.6 | 102 | 124 | 43 | 49 |
| 774 | 6 | CAS3 | CAS12 | CAS15 | CAS24 | 0.2 | 4.5 | 7.9 | 0.6 | 16.4 | 61 | 18 | 194 | 50 |
| 736 | 64 | CAS3 | CAS12 | CAS13 | CAS21 | 0.2 | 4.0 | 7.9 | 0.7 | 16.6 | 66 | 78 | 135 | 51 |
| 2168 | 56 | CAS9 | CAS12 | CAS13 | CAS21 | 0.1 | 1.9 | 7.9 | 0.8 | 15.9 | 70 | 99 | 111 | 52 |
| 1207 | 55 | CAS5 | CAS12 | CAS13 | CAS24 | 0.0 | 2.2 | 7.5 | 0.5 | 14.8 | 16 | 11 | 265 | 53 |
| 503 | 23 | CAS2 | CAS12 | CAS14 | CAS23 | 0.1 | 2.3 | 7.9 | 0.7 | 15.7 | 74 | 75 | 148 | 54 |
| 2552 | 56 | CAS2 | CAS11 | CAS18 | CAS23 | 0.1 | 3.8 | 7.4 | 0.6 | 15.6 | 6 | 24 | 269 | 55 |
| 839 | 71 | CAS3 | CAS12 | CAS19 | CAS24 | 0.2 | 3.9 | 8.0 | 0.7 | 16.5 | 87 | 71 | 144 | 56 |
| 521 | 41 | CAS2 | CAS12 | CAS15 | CAS24 | 0.1 | 3.8 | 8.1 | 0.8 | 17.0 | 99 | 109 | 98 | 57 |
| 740 | 68 | CAS3 | CAS12 | CAS13 | CAS23 | 0.1 | 4.0 | 7.9 | 0.7 | 16.3 | 76 | 59 | 176 | 58 |
| 2086 | 70 | CAS9 | CAS11 | CAS15 | CAS24 | 0.1 | 3.1 | 7.7 | 0.7 | 15.7 | 38 | 84 | 192 | 59 |
| 2565 | 69 | CAS2 | CAS11 | CAS19 | CAS22 | 0.1 | 4.5 | 7.9 | 0.6 | 16.2 | 58 | 41 | 225 | 60 |
| 2276 | 68 | CAS9 | CAS11 | CAS15 | CAS23 | 0.1 | 2.1 | 8.2 | 0.7 | 15.7 | 115 | 81 | 136 | 61 |
| 406 | 22 | CAS2 | CAS11 | CAS16 | CAS23 | 0.1 | 1.8 | 8.2 | 0.7 | 15.6 | 137 | 67 | 132 | 62 |
| 758 | 86 | CAS3 | CAS12 | CAS14 | CAS24 | 0.0 | 2.2 | 7.8 | 0.5 | 14.6 | 44 | 8 | 298 | 63 |
| 2440 | 40 | CAS10 | CAS12 | CAS14 | CAS23 | 0.1 | 3.5 | 8.0 | 0.7 | 16.0 | 86 | 90 | 174 | 63 |

TABLE 11-continued

Results of the growth experiments of the 150 best strains (top 150). In the first two columns the identification of the strain experiments is given. In columns 3-6, the construct of the strain is given, for AADH, ACS, GLDA and DAK1. Columns 7-11 indicates the results of the fermentation, concentrations (g/l) of glucose, xylose, glycerol, acetate and ethanol, respectively. Columns 12-14 give the ranking of strains for each product (glycerol and acetate consumption) and ethanol production. Column 15 gives total ranking based on the rankings in column 12-14.

| Num | Expno | AADH | ACS | GLDA | DAK1 | glucose | xylose | glycerol | acetate | ethanol | Glycerol Rank | Acetate Rank | EtOH Rank | Total Rank |
|---|---|---|---|---|---|---|---|---|---|---|---|---|---|---|
| 2553 | 57 | CAS2 | CAS11 | CAS18 | CAS24 | 0.2 | 5.3 | 7.7 | 0.6 | 15.8 | 29 | 16 | 328 | 65 |
| 790 | 22 | CAS3 | CAS12 | CAS16 | CAS24 | 0.1 | 2.9 | 8.5 | 0.7 | 17.3 | 230 | 79 | 66 | 66 |
| 631 | 55 | CAS3 | CAS11 | CAS14 | CAS24 | 0.2 | 4.2 | 8.1 | 0.7 | 16.1 | 101 | 77 | 201 | 67 |
| 407 | 23 | CAS2 | CAS11 | CAS16 | CAS23 | 0.0 | 1.4 | 8.0 | 0.7 | 14.5 | 78 | 61 | 244 | 68 |
| 751 | 79 | CAS3 | CAS12 | CAS14 | CAS21 | 0.1 | 3.5 | 8.3 | 0.8 | 16.3 | 147 | 92 | 149 | 69 |
| 2549 | 53 | CAS2 | CAS11 | CAS18 | CAS22 | 0.2 | 4.7 | 7.4 | 0.6 | 15.5 | 9 | 39 | 341 | 70 |
| 499 | 19 | CAS2 | CAS12 | CAS14 | CAS21 | 0.1 | 3.3 | 8.1 | 0.8 | 16.2 | 111 | 135 | 156 | 71 |
| 655 | 79 | CAS3 | CAS11 | CAS15 | CAS28 | 0.1 | 1.4 | 8.7 | 0.7 | 16.8 | 286 | 66 | 55 | 72 |
| 1303 | 55 | CAS5 | CAS12 | CAS19 | CAS24 | 0.1 | 5.3 | 8.0 | 0.7 | 16.4 | 84 | 72 | 261 | 73 |
| 788 | 20 | CAS3 | CAS12 | CAS16 | CAS23 | 0.1 | 5.5 | 7.8 | 0.4 | 15.9 | 50 | 5 | 363 | 74 |
| 1138 | 82 | CAS5 | CAS11 | CAS16 | CAS21 | 0.1 | 2.5 | 8.2 | 0.9 | 16.0 | 130 | 159 | 129 | 74 |
| 2056 | 40 | CAS9 | CAS11 | CAS13 | CAS24 | 0.1 | 3.3 | 7.9 | 0.8 | 15.6 | 73 | 123 | 229 | 76 |
| 2069 | 53 | CAS9 | CAS11 | CAS14 | CAS23 | 0.0 | 3.6 | 7.9 | 0.8 | 15.6 | 63 | 120 | 249 | 77 |
| 735 | 63 | CAS3 | CAS12 | CAS13 | CAS21 | 0.2 | 4.3 | 8.3 | 0.8 | 16.6 | 154 | 128 | 154 | 78 |
| 1458 | 18 | CAS6 | CAS12 | CAS15 | CAS21 | 0.1 | 4.6 | 8.1 | 0.7 | 16.0 | 96 | 76 | 268 | 79 |
| 815 | 47 | CAS3 | CAS12 | CAS17 | CAS28 | 0.1 | 2.1 | 8.9 | 0.7 | 17.6 | 344 | 68 | 32 | 80 |
| 1216 | 64 | CAS5 | CAS12 | CAS14 | CAS21 | 0.1 | 4.6 | 8.1 | 0.8 | 16.1 | 108 | 102 | 236 | 81 |
| 1276 | 28 | CAS5 | CAS12 | CAS17 | CAS27 | 0.1 | 2.3 | 8.4 | 1.0 | 17.0 | 188 | 218 | 65 | 82 |
| 629 | 53 | CAS3 | CAS11 | CAS14 | CAS23 | 0.1 | 4.2 | 8.3 | 0.8 | 16.1 | 142 | 118 | 218 | 83 |
| 836 | 68 | CAS3 | CAS12 | CAS19 | CAS23 | 0.1 | 2.0 | 8.8 | 0.8 | 17.4 | 303 | 137 | 38 | 83 |
| 642 | 66 | CAS3 | CAS11 | CAS15 | CAS21 | 0.2 | 5.0 | 8.0 | 0.8 | 16.0 | 92 | 107 | 282 | 85 |
| 1553 | 17 | CAS7 | CAS11 | CAS14 | CAS23 | 0.1 | 3.1 | 7.6 | 0.7 | 14.4 | 25 | 49 | 413 | 86 |
| 998 | 38 | CAS4 | CAS12 | CAS13 | CAS23 | 0.1 | 2.8 | 8.5 | 1.0 | 17.3 | 201 | 245 | 62 | 87 |
| 1031 | 71 | CAS4 | CAS12 | CAS15 | CAS23 | 0.1 | 3.6 | 8.3 | 0.9 | 16.2 | 161 | 189 | 160 | 88 |
| 613 | 37 | CAS3 | CAS11 | CAS13 | CAS23 | 0.1 | 3.0 | 8.3 | 0.7 | 15.1 | 169 | 65 | 280 | 89 |
| 821 | 53 | CAS3 | CAS12 | CAS18 | CAS23 | 0.1 | 2.0 | 8.8 | 0.9 | 17.2 | 326 | 141 | 49 | 90 |
| 1016 | 56 | CAS4 | CAS12 | CAS14 | CAS23 | 0.1 | 2.6 | 8.4 | 1.0 | 16.6 | 175 | 261 | 87 | 91 |
| 1713 | 81 | CAS7 | CAS12 | CAS16 | CAS24 | 0.1 | 3.9 | 7.9 | 0.7 | 14.9 | 68 | 74 | 387 | 92 |
| 755 | 83 | CAS3 | CAS12 | CAS14 | CAS23 | 0.1 | 4.1 | 7.7 | 0.6 | 14.5 | 31 | 25 | 486 | 93 |
| 1666 | 34 | CAS7 | CAS12 | CAS13 | CAS24 | 0.1 | 3.3 | 8.1 | 0.8 | 15.0 | 107 | 113 | 324 | 94 |
| 1001 | 41 | CAS4 | CAS12 | CAS13 | CAS24 | 0.1 | 4.7 | 8.3 | 0.9 | 16.4 | 163 | 178 | 207 | 95 |
| 1268 | 20 | CAS5 | CAS12 | CAS17 | CAS23 | 0.1 | 3.3 | 8.7 | 0.9 | 16.7 | 270 | 180 | 99 | 96 |
| 1112 | 56 | CAS5 | CAS11 | CAS14 | CAS21 | 0.1 | 3.3 | 8.3 | 0.8 | 15.2 | 164 | 110 | 277 | 97 |
| 1206 | 54 | CAS5 | CAS12 | CAS13 | CAS24 | 0.2 | 5.2 | 7.7 | 0.7 | 15.1 | 37 | 56 | 463 | 98 |
| 1012 | 52 | CAS4 | CAS12 | CAS14 | CAS21 | 0.1 | 2.8 | 8.5 | 1.0 | 16.9 | 213 | 268 | 81 | 99 |
| 752 | 80 | CAS3 | CAS12 | CAS14 | CAS21 | 0.1 | 4.7 | 8.3 | 0.9 | 16.1 | 156 | 145 | 264 | 100 |
| 1107 | 51 | CAS5 | CAS11 | CAS13 | CAS25 | 0.1 | 2.0 | 8.7 | 1.0 | 17.3 | 277 | 243 | 45 | 100 |
| 791 | 23 | CAS3 | CAS12 | CAS16 | CAS25 | 0.1 | 2.1 | 9.0 | 0.8 | 17.2 | 384 | 133 | 52 | 102 |
| 903 | 39 | CAS4 | CAS11 | CAS15 | CAS24 | 0.1 | 3.2 | 8.6 | 1.0 | 16.7 | 241 | 236 | 97 | 103 |
| 1280 | 32 | CAS5 | CAS12 | CAS18 | CAS21 | 0.1 | 2.9 | 8.4 | 1.0 | 15.9 | 185 | 235 | 157 | 104 |
| 1805 | 77 | CAS8 | CAS11 | CAS14 | CAS23 | 0.2 | 5.5 | 7.9 | 0.8 | 15.7 | 72 | 126 | 385 | 105 |
| 1027 | 67 | CAS4 | CAS12 | CAS15 | CAS21 | 0.1 | 3.6 | 8.4 | 1.0 | 16.2 | 193 | 229 | 163 | 106 |
| 1664 | 32 | CAS7 | CAS12 | CAS13 | CAS23 | 0.2 | 4.5 | 8.3 | 0.9 | 15.8 | 149 | 151 | 285 | 106 |
| 483 | 3 | CAS2 | CAS12 | CAS13 | CAS21 | 0.1 | 5.0 | 8.5 | 0.8 | 16.4 | 227 | 125 | 239 | 108 |
| 2188 | 76 | CAS9 | CAS12 | CAS14 | CAS23 | 0.1 | 3.8 | 8.1 | 0.9 | 15.0 | 94 | 164 | 343 | 109 |
| 1034 | 74 | CAS4 | CAS12 | CAS15 | CAS24 | 0.1 | 3.0 | 8.7 | 1.0 | 17.2 | 268 | 264 | 70 | 110 |
| 612 | 36 | CAS3 | CAS11 | CAS13 | CAS23 | 0.1 | 4.0 | 7.6 | 0.5 | 13.9 | 20 | 14 | 573 | 111 |
| 789 | 21 | CAS3 | CAS12 | CAS16 | CAS24 | 0.2 | 6.7 | 8.1 | 0.6 | 15.8 | 104 | 33 | 475 | 112 |
| 1220 | 68 | CAS5 | CAS12 | CAS14 | CAS23 | 0.2 | 4.2 | 7.7 | 0.6 | 14.2 | 32 | 42 | 540 | 113 |
| 1269 | 21 | CAS5 | CAS12 | CAS17 | CAS23 | 0.1 | 3.6 | 8.6 | 0.9 | 16.0 | 257 | 174 | 185 | 114 |
| 1106 | 50 | CAS5 | CAS11 | CAS13 | CAS25 | 0.0 | 1.3 | 9.0 | 1.0 | 22.3 | 397 | 216 | 6 | 115 |
| 1047 | 87 | CAS4 | CAS12 | CAS16 | CAS23 | 0.1 | 3.5 | 8.3 | 0.8 | 14.8 | 141 | 122 | 366 | 116 |
| 490 | 10 | CAS2 | CAS12 | CAS13 | CAS24 | 0.1 | 3.7 | 7.7 | 0.6 | 13.9 | 34 | 47 | 552 | 117 |
| 1711 | 79 | CAS7 | CAS12 | CAS16 | CAS23 | 0.2 | 5.6 | 8.2 | 0.9 | 15.8 | 126 | 149 | 358 | 117 |
| 534 | 54 | CAS2 | CAS12 | CAS16 | CAS23 | 0.1 | 5.3 | 8.4 | 0.9 | 16.3 | 173 | 195 | 273 | 119 |
| 1555 | 19 | CAS7 | CAS11 | CAS14 | CAS24 | 0.1 | 3.4 | 8.2 | 0.8 | 14.5 | 117 | 105 | 426 | 120 |
| 1554 | 18 | CAS7 | CAS11 | CAS14 | CAS23 | 0.1 | 4.5 | 7.8 | 0.8 | 14.6 | 52 | 95 | 504 | 121 |
| 1044 | 84 | CAS4 | CAS12 | CAS16 | CAS21 | 0.1 | 2.9 | 8.8 | 0.9 | 16.0 | 318 | 192 | 143 | 122 |
| 887 | 23 | CAS4 | CAS11 | CAS14 | CAS24 | 0.0 | 2.0 | 8.8 | 1.0 | 15.8 | 314 | 213 | 127 | 123 |
| 1699 | 67 | CAS7 | CAS12 | CAS15 | CAS25 | 0.1 | 2.0 | 8.9 | 1.0 | 17.5 | 348 | 272 | 34 | 123 |
| 616 | 40 | CAS3 | CAS11 | CAS13 | CAS25 | 0.0 | 1.5 | 9.0 | 1.0 | 17.1 | 391 | 225 | 40 | 125 |
| 1683 | 51 | CAS7 | CAS12 | CAS14 | CAS24 | 0.3 | 6.8 | 8.4 | 0.9 | 16.6 | 181 | 169 | 126 | 126 |
| 1329 | 81 | CAS6 | CAS11 | CAS13 | CAS21 | 0.2 | 5.0 | 8.2 | 0.8 | 15.1 | 124 | 111 | 431 | 127 |
| 2550 | 54 | CAS2 | CAS11 | CAS18 | CAS22 | 0.1 | 2.7 | 8.8 | 1.0 | 16.3 | 315 | 246 | 113 | 128 |
| 1324 | 76 | CAS5 | CAS12 | CAS20 | CAS27 | 0.2 | 3.6 | 8.7 | 1.0 | 15.9 | 264 | 228 | 191 | 129 |
| 1565 | 29 | CAS7 | CAS11 | CAS15 | CAS21 | 0.2 | 4.7 | 8.3 | 0.9 | 15.4 | 152 | 170 | 361 | 129 |
| 2523 | 27 | CAS2 | CAS11 | CAS16 | CAS25 | 0.2 | 4.5 | 8.4 | 0.9 | 15.7 | 195 | 200 | 288 | 129 |
| 656 | 80 | CAS3 | CAS11 | CAS15 | CAS28 | 0.1 | 2.3 | 9.0 | 0.9 | 16.2 | 414 | 166 | 104 | 132 |
| 391 | 7 | CAS2 | CAS11 | CAS15 | CAS23 | 0.1 | 4.3 | 8.4 | 0.8 | 15.1 | 172 | 136 | 381 | 133 |
| 796 | 28 | CAS3 | CAS12 | CAS16 | CAS27 | 0.1 | 2.3 | 9.0 | 1.0 | 16.9 | 388 | 232 | 71 | 134 |
| 322 | 34 | CAS1 | CAS12 | CAS19 | CAS21 | 0.2 | 4.5 | 8.6 | 1.0 | 15.9 | 238 | 212 | 246 | 135 |

TABLE 11-continued

Results of the growth experiments of the 150 best strains (top 150). In the first two columns the identification of the strain experiments is given. In columns 3-6, the construct of the strain is given, for AADH, ACS, GLDA and DAK1. Columns 7-11 indicates the results of the fermentation, concentrations (g/l) of glucose, xylose, glycerol, acetate and ethanol, respectively. Columns 12-14 give the ranking of strains for each product (glycerol and acetate consumption) and ethanol production. Column 15 gives total ranking based on the rankings in column 12-14.

| Num | Expno | AADH | ACS | GLDA | DAK1 | glucose | xylose | glycerol | acetate | ethanol | Glycerol Rank | Acetate Rank | EtOH Rank | Total Rank |
|---|---|---|---|---|---|---|---|---|---|---|---|---|---|---|
| 628 | 52 | CAS3 | CAS11 | CAS14 | CAS22 | 0.1 | 2.0 | 9.1 | 0.9 | 16.8 | 444 | 196 | 64 | 136 |
| 507 | 27 | CAS2 | CAS12 | CAS14 | CAS25 | 0.1 | 1.8 | 8.8 | 1.1 | 16.8 | 316 | 328 | 61 | 137 |
| 1302 | 54 | CAS5 | CAS12 | CAS19 | CAS24 | 0.1 | 6.3 | 8.1 | 0.8 | 15.6 | 106 | 116 | 484 | 138 |
| 822 | 54 | CAS3 | CAS12 | CAS18 | CAS24 | 0.0 | 0.8 | 9.1 | 1.0 | 17.5 | 437 | 248 | 25 | 139 |
| 545 | 65 | CAS2 | CAS12 | CAS17 | CAS21 | 0.1 | 1.5 | 8.8 | 1.1 | 17.5 | 323 | 358 | 30 | 140 |
| 920 | 56 | CAS4 | CAS11 | CAS16 | CAS24 | 0.1 | 3.2 | 8.7 | 1.0 | 16.0 | 292 | 260 | 162 | 141 |
| 795 | 27 | CAS3 | CAS12 | CAS16 | CAS27 | 0.1 | 1.9 | 9.2 | 0.9 | 17.1 | 520 | 146 | 51 | 142 |
| 882 | 18 | CAS4 | CAS11 | CAS14 | CAS21 | 0.1 | 2.5 | 8.9 | 1.0 | 16.2 | 341 | 265 | 115 | 143 |
| 746 | 74 | CAS3 | CAS12 | CAS13 | CAS26 | 0.1 | 2.9 | 8.7 | 1.0 | 15.5 | 266 | 258 | 214 | 144 |
| 832 | 64 | CAS3 | CAS12 | CAS19 | CAS21 | 0.2 | 5.4 | 8.5 | 0.9 | 15.6 | 209 | 157 | 372 | 144 |
| 1018 | 58 | CAS4 | CAS12 | CAS14 | CAS24 | 0.1 | 3.5 | 8.7 | 1.0 | 16.3 | 287 | 292 | 159 | 144 |
| 368 | 80 | CAS2 | CAS11 | CAS13 | CAS28 | 0.1 | 0.9 | 8.9 | 1.1 | 17.5 | 374 | 343 | 24 | 147 |
| 581 | 5 | CAS2 | CAS12 | CAS19 | CAS23 | 0.0 | 2.5 | 8.0 | 0.7 | 13.1 | 82 | 51 | 611 | 148 |
| 423 | 39 | CAS2 | CAS11 | CAS17 | CAS23 | 0.1 | 3.7 | 8.6 | 1.0 | 15.6 | 251 | 237 | 259 | 149 |
| 756 | 84 | CAS3 | CAS12 | CAS14 | CAS23 | 0.2 | 6.2 | 7.7 | 0.7 | 14.7 | 39 | 83 | 628 | 150 |

In FIG. 3, the residual acetic acid concentration in the fermentation broth is plotted as a function of the residual glycerol concentration. The results clearly show that there is a strong correlation between the residual glycerol concentration and the residual acetic acid concentration: the lower the residual glycerol concentration after fermentation, the lower the residual acetic acid concentration is. This indicates that both pathways are connected to each other, as was already shown in patent application WO2013/081456.

One of the strains consumed almost all acetic acid (data point lower left corner in FIG. 3) and outperformed the other transformants. This strain was designated YD01247.

In total, 2592 strains were screened, including reference strain RN1189. Reference strain RN1189 was included 27 times. The performance of reference strain RN1189 relative to the other strains (total 2592) is depicted FIG. 6. The strains are ranked as described before, where the better performing strains are indicated by a lighter color (and are closer to the bottom-left corner of the graph). The less well performing strains are indicated by a darker color; the change in color is gradual. The exception is that the reference strain, RN1189, is indicated in the darkest color.

In order to assess the best combinations of expression cassettes, calculations were performed using the NMR data. All strains were scored on:

1) the residual acetic acid concentration left in the medium,
2) the residual glycerol concentration left in the medium,
3) the amount of ethanol produced from glycerol and acetic acid, by subtracting the theoretical amount of ethanol produced from xylose and glucose from the total amount of ethanol produced.

All samples were ranked by adding the three scores (table 11). The best 150 strains based on this last score was visualized, and is also displayed in FIG. 4.

From the best 150 strains, it was determined which expression cassettes, belonging to the groups A. B, C and D (vide supra), were overrepresented. See tables 11 and 12.

TABLE 12

Number of occurrences of each expression cassette in the top 150 best performing transformants is depicted in the table below.

| | |
|---|---|
| CAS1 | 2 |
| CAS2 | 36 |
| CAS3 | 44 |
| CAS4 | 15 |
| CAS5 | 22 |
| CAS6 | 2 |
| CAS7 | 18 |
| CAS8 | 1 |
| CAS9 | 8 |
| CAS10 | 2 |
| CAS11 | 89 |
| CAS12 | 61 |
| CAS13 | 35 |
| CAS14 | 37 |
| CAS15 | 27 |
| CAS16 | 24 |
| CAS17 | 6 |
| CAS18 | 9 |
| CAS19 | 11 |
| CAS20 | 1 |
| CAS21 | 38 |
| CAS22 | 4 |
| CAS23 | 51 |
| CAS24 | 39 |
| CAS25 | 9 |
| CAS26 | 1 |
| CAS27 | 4 |
| CAS28 | 4 |

Observations are:

a) in general, the use of strong promoters is counted more frequently than the use of weak(er) promoters, as expression cassettes harboring strong promoters are overrepresented in the 150 strains as compared to weak(er) promoters;

b) CAS2 and CAS3 are overrepresented in the AADH-group;

c) CAS11 and CAS12 are about equally well represented;

d) CAS 13 and CAS 14 seems to be slightly overrepresented in the GLD-group, although the expression cassettes CAS 15 and CAS16 are also well represented;

e) CAS 23 is overrepresented in the DAK-group, though CAS21 and CAS23 are also well represented in the top 150 strains;

f) all expression cassettes (CAS) that were tested are represented in the top 150 strains, indicating that multiple solutions exist.

However, many combinations of expression cassettes led to an improved ethanol yield, due to increased glycerol and acetic acid conversion, as compared to reference strain RN1189. This indicates that many other combinations of expression cassettes may provide a solution for converting both glycerol and acetic acid into ethanol, in a mixture consisting of these two compounds and fermentable sugars. Strain YD01247, the best strain in the screening (FIGS. 3 and 4) is an illustration of this: it consists of expression cassettes CAS01, CAS12, CAS13 and CAS23.

A number of strains nearly consumed all available acetic acid. These strains were able to consume 3 to 4 grams of glycerol per liter.

Example 3

Retesting of the Best Combinations of Expression Cassettes

In a multifactorial design, the best combinations of expression cassettes (Example 2) were re-tested. Since in strain YD01247 the expression of the ACS2-gene was under control of the construct with the weak promoter (i.e. CAS12), this expression cassette was taken along in the experimental design as well, though it was not overrepresented in the top 150 strains in Example 2.

Strain RN1069 was transformed with 8 combinations of expression cassettes selected from groups A, B, C and D (table 13).

TABLE 13

Retesting best combinations of expression cassettes

| Retransformation | Group A | Group B | Group C | Group D |
|---|---|---|---|---|
| R1 | CAS02 | CAS11 | CAS13 | CAS21 |
| R2 | CAS02 | CAS11 | CAS13 | CAS23 |
| R3 | CAS02 | CAS12 | CAS13 | CAS21 |
| R4 | CAS02 | CAS12 | CAS13 | CAS23 |
| R5 | CAS03 | CAS11 | CAS13 | CAS21 |
| R6 | CAS03 | CAS11 | CAS13 | CAS23 |
| R7 | CAS03 | CAS12 | CAS13 | CAS21 |
| R8 | CAS03 | CAS12 | CAS13 | CAS23 |

After transformation, cells were spread on YEP-agar supplemented with 20 g glucose/liter and 200 µg G418/ml. Per transformation, eight independent colonies were used to inoculate microplates filled with YEP-agar supplemented with 20 g glucose/liter and 200 µg G418/ml, except for R2; in this case only three transformants were obtained. As reference strains, RN1069, RN1189 and YD01247 were included, also in eightfold.

The strains in the microplate with YEPD-agar and G418 were used to inoculate 275 µl Mineral Medium containing 200 µg histidine per ml, 2% glucose, 2% xylose, 1% glycerol and 2 g/l acetic acid, in microplates, in triplicate. The pH of the medium was set at 4.5, below the pKa of acetic acid. The microplate was sealed and incubated under anaerobic conditions. At three different time intervals, i.e. after 24, 48 and 72 hours, one plate per time point was recovered from the anaerobic shaker. Cells were spun down by centrifugation and the supernatant was analyzed by NMR. The NMR results, in particular the residual concentrations of glycerol and acetic acid, after 72 hours incubation is shown in FIG. 5.

The residual acetic acid concentration in strain RN1069, one of the reference strains, is still close to 2.0 g/l, which is in line with the expectations. Likewise, this strain also did not consume glycerol.

The proof of concept strain RN1189 (WO2013/081456) consumed in average 0.9 gram acetic acid per liter and 1.5 grams of glycerol per liter.

The reference strain YD01247 performed best of all; the residual acetic acid concentration was only 0.2 gram per liter (90% of acetic acid consumed) and the residual glycerol concentration was only 5.5 gram per liter.

The residual acetic acid concentration of the reconstructed transformants (except for R2) was between 0.3 and 0.6 gram per liter and the residual glycerol concentration was between 6.6 and 7.0 grams per liter.

Transformation R2 not only yielded few transformants, but also a large spread was observed in the results. Therefore, these results were not interpreted.

In conclusion, all combinations of expression cassettes tested, except R2, resulted in an improved performance in terms of anaerobic glycerol and acetic acid conversion as compared to the reference strain RN1189.

Example 4

Anaerobic Shake Flask Experiment with Selected Transformants

The performance of a selection of transformants was tested in shake flasks. To this end, precultures of the strains in table 14, generated in Example 2, were prepared.

TABLE 14

Strains used in the anaerobic shake flask experiment and the presence of expression cassettes.

| Strain | GPD1 | GPD2 | HIS3 | AADH | ACS | GLD | DAK |
|---|---|---|---|---|---|---|---|
| CEN.PK113-7D | present | present | present | none | none | none | none |
| RN1069 | deleted | deleted | deleted | none | none | none | none |
| RN1189 | deleted | deleted | complemented by plasmid | adhE Ec (plasmid) | none | gldA Ec (plasmid) | DAK1 Sc (plasmid) |
| YD01247 | deleted | deleted | deleted | CAS1 | CAS12 | CAS13 | CAS23 |
| YD01248 | deleted | deleted | deleted | CAS2 | CAS11 | CAS13 | CAS21 |
| YD01249 | deleted | deleted | deleted | CAS2 | CAS11 | CAS13 | CAS23 |
| YD01250 | deleted | deleted | deleted | CAS2 | CAS11 | CAS15 | CAS21 |
| YD01251 | deleted | deleted | deleted | CAS2 | CAS12 | CAS15 | CAS23 |

Strain YD01247, YD01248, YD01249 and YD01250 are indicated in FIG. 7 as numbers 1, 2, 3 and 4 respectively. Strain YD01251 is a strain that performs medium well in terms of glycerol and acetic acid consumption.

100 ml shake flask were filled with 25 ml of Mineral Medium (as described in Material and Methods) containing approximately per liter: 20 grams of glucose, 20 grams of xylose, 10 grams of glycerol, 200 mg histidine and 2 grams of acetic acid (HAc), pH 4.5.

These shake flasks were inoculated, in duplicate, with washed cells from the precultures with the amount needed to achieve an initial OD600 of 0.5. The flasks were closed with waterlocks in order to achieve anaerobic conditions during the fermentation. The incubation was done at 32° C. and 100 rpm. After 96 hours, the fermentation was terminated and cells were spun down by centrifugation. The supernatant was analyzed by NMR. The results are shown in table 15.

TABLE 15

Averaged NMR results of the shake anaerobic flask experiment

|  | Glucose (g/l) | Xylose (g/l) | Glycerol (g/l) | Acetic acid (g/l) | Ethanol (g/l) | Ethanol yield on consumed sugars (g/g) |
|---|---|---|---|---|---|---|
| Medium | 21.1 | 19.9 | 9.2 | 2.0 | 0.2 | 0.00 |
| CEN.PK113-7D | 0.6 | 20.3 | 9.2 | 2.0 | 9.1 | 0.44 |
| RN1069 | 2.3 | 12.9 | 9.3 | 1.7 | 10.1 | 0.39 |
| RN1189 | 0.1 | 2.0 | 7.4 | 1.4 | 18.8 | 0.48 |
| YD01247 | 0.1 | 6.5 | 4.8 | 0.2 | 17.1 | 0.50 |
| YD01248 | 0.2 | 1.4 | 5.0 | 0.3 | 19.5 | 0.49 |
| YD01249 | 0.2 | 1.2 | 5.3 | 0.4 | 19.4 | 0.49 |
| YD01250 | 0.1 | 0.8 | 5.4 | 0.4 | 19.4 | 0.48 |
| YD01251 | 0.0 | 1.6 | 5.8 | 0.6 | 19.0 | 0.48 |

Strain CEN.PK113-7D only ferments glucose, which is in line with the expectations. The ethanol yield, calculated on basis of consumed sugars, is 0.44, which is in concordance with what is usually found in shake flask fermentations. The theoretical maximum ethanol yield amounts 0.51 grams of ethanol per gram of sugar.

Strain RN1069 can, in principle, ferment both glucose and xylose. However, this strain has a deletion of both GPD1 and GPD2, which disables co-factor regeneration under anaerobic conditions. Yet, this strain converts glucose and xylose partly, presumably because at the start of the experiment, some residual oxygen was available in the head space of the shake flask, as well as dissolved oxygen in the medium, enabling some cofactor recycling in the beginning of the experiment. Yet, the ethanol yield is low, 0.39 grams of ethanol per gram of consumed sugar.

The transformed strains expressing AADH, GLD and DAK from a plasmid (RN1189) or expressing AADH, ACS, GLD and DAK from an integrated construct in the genome (YD01247 through YD01251) show an increased ethanol yield per consumed sugar. Ethanol yields of 0.48 up to 0.50 are achieved. These higher values were achieved due to the anaerobic conversion of glycerol and acetic acid into ethanol and/or the absence of glycerol production.

Strain YD01247 has consumed less xylose than the other YD-strains. However, this strain has consumed almost all acetic acid, as was already shown in Examples 2 and 3. This strain has also consumed most of the glycerol. This strain showed the highest ethanol yield.

The other YD-strains also show an improved performance relative to strain RN1189: more glycerol and acetic acid were consumed, leading to a higher ethanol titer.

These experiments show that various alternative combinations of expression cassettes resulted in an improved performance in terms of anaerobic glycerol and acetic acid conversion as compared to the reference strain RN1189, resulting in a higher ethanol titer in all cases and a higher ethanol yield in some cases.

LITERATURE

Engler C. et al (2011) Generation of families of construct variants using golden gate shuffling. Methods Mol Biol. 2011; 729:1, 67-81. doi: 10.1007/978-1-61779-065-2_11;

Guadalupe Medina V, Almering M J, van Maris A J, Pronk J T (2009) "Elimination of glycerol production in anaerobic cultures of Saccharomyces cerevisiae engineered for use of acetic acid as electron acceptor." Appl Environ Microbiol.;

Lee and Dasilva (2006) Application of sequential integration for metabolic engineering of 1,2-propanediol production in yeast. Metab Eng. 8(1):58-65;

Sonderegger et al (2004) Metabolic Engineering of a Phosphoketolase Pathway for Pentose Catabolism in Saccharomyces cerevisiae. AEM 70(5), 2892-2897;

Van Dijken and Scheffers (1986) Redox balances in the metabolism of sugars by yeasts. FEMS Microbiology Letters Volume 32, Issue 3-4, pages 199-224;

Yu et at (2010) Engineering of glycerol utilization pathway for ethanol production by Saccharomyces cerevisiae. Bioresour. Technol. 101(11):4157-4161;

Yu et al (2011) Improvement of ethanol yield from glycerol via conversion of pyruvate to ethanol in metabolically engineered Saccharomyces cerevisiae. Appl Biochem Biotecnol doi:10.1007/s12010-011-9475-9;

Patent application PCT/EP2013/056623 (non-published);

Patent application WO 2013/081456;

Patent application WO 2011/010923.

The invention claimed is:

1. A *Saccharomyces cerevisiae* cell that is genetically modified comprising:
   a) a recombinant nucleotide sequence encoding a NAD+-dependent acetylating acetaldehyde dehydrogenase (E.C. 1.2.1.10) of SEQ ID NO: 2;
   b) a recombinant nucleotide sequence encoding an acetyl-CoA synthetase (E.C. 6.2.1.1) of SEQ ID NO: 6;
   c) a recombinant nucleotide sequence encoding a glycerol dehydrogenase (E.C. 1.1.1.6) of SEQ ID NO: 7; and
   d) a recombinant nucleotide sequence encoding a dihydroxyacetone kinase (E.C. 2.7.1.28 or E.C. 2.7.1.29) of SEQ ID NO: 13; wherein
   wherein the recombinant nucleotide sequences are overexpressed in the yeast cell.

2. The *Saccharomyces cerevisiae* cell according to claim 1, comprising a deletion or disruption of one or more endogenous nucleotide sequence encoding a glycerol 3-phosphate phosphohydrolase and/or encoding a glycerol 3-phosphate dehydrogenase gene.

3. The *Saccharomyces cerevisiae* cell according to claim 1, wherein in the yeast cell, all endogenous nucleotide sequences encoding a glycerol 3-phosphate phosphohydrolase and all endogenous nucleotide sequences encoding a glycerol 3-phosphate dehydrogenase are deleted.

4. The *Saccharomyces cerevisiae* cell according to claim 3, wherein the yeast cell is free of genes encoding NADH-dependent glycerol 3-phosphate dehydrogenase.

5. The *Saccharomyces cerevisiae* cell according to claim 1 capable of being used for the preparation of ethanol.

* * * * *

SEQUENCE LISTING

<160> NUMBER OF SEQ ID NOS: 61

<210> SEQ ID NO 1
<211> LENGTH: 891
<212> TYPE: PRT
<213> ORGANISM: Escherichia coli

<400> SEQUENCE: 1

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro

```
            35                  40                  45
Leu Ala Lys Met Ala Val Ala Glu Ser Gly Met Gly Ile Val Glu Asp
 50                  55                  60
Lys Val Ile Lys Asn His Phe Ala Ser Glu Tyr Ile Tyr Asn Ala Tyr
 65                  70                  75                  80
Lys Asp Glu Lys Thr Cys Gly Val Leu Ser Glu Asp Asp Thr Phe Gly
                 85                  90                  95
Thr Ile Thr Ile Ala Glu Pro Ile Gly Ile Cys Gly Ile Val Pro
                100                 105                 110
Thr Thr Asn Pro Thr Ser Thr Ala Ile Phe Lys Ser Leu Ile Ser Leu
                115                 120                 125
Lys Thr Arg Asn Ala Ile Ile Phe Ser Pro His Pro Arg Ala Lys Asp
                130                 135                 140
Ala Thr Asn Lys Ala Ala Asp Ile Val Leu Gln Ala Ala Ile Ala Ala
145                 150                 155                 160
Gly Ala Pro Lys Asp Leu Ile Gly Trp Ile Asp Gln Pro Ser Val Glu
                165                 170                 175
Leu Ser Asn Ala Leu Met His His Pro Asp Ile Asn Leu Ile Leu Ala
                180                 185                 190
Thr Gly Gly Pro Gly Met Val Lys Ala Ala Tyr Ser Ser Gly Lys Pro
                195                 200                 205
Ala Ile Gly Val Gly Ala Gly Asn Thr Pro Val Val Ile Asp Glu Thr
210                 215                 220
Ala Asp Ile Lys Arg Ala Val Ala Ser Val Leu Met Ser Lys Thr Phe
225                 230                 235                 240
Asp Asn Gly Val Ile Cys Ala Ser Glu Gln Ser Val Val Val Asp
                245                 250                 255
Ser Val Tyr Asp Ala Val Arg Glu Arg Phe Ala Thr His Gly Gly Tyr
                260                 265                 270
Leu Leu Gln Gly Lys Glu Leu Lys Ala Val Gln Asp Val Ile Leu Lys
                275                 280                 285
Asn Gly Ala Leu Asn Ala Ala Ile Val Gly Gln Pro Ala Tyr Lys Ile
290                 295                 300
Ala Glu Leu Ala Gly Phe Ser Val Pro Glu Asn Thr Lys Ile Leu Ile
305                 310                 315                 320
Gly Glu Val Thr Val Val Asp Glu Ser Glu Pro Phe Ala His Glu Lys
                325                 330                 335
Leu Ser Pro Thr Leu Ala Met Tyr Arg Ala Lys Asp Phe Glu Asp Ala
                340                 345                 350
Val Glu Lys Ala Glu Lys Leu Val Ala Met Gly Gly Ile Gly His Thr
                355                 360                 365
Ser Cys Leu Tyr Thr Asp Gln Asp Asn Gln Pro Ala Arg Val Ser Tyr
                370                 375                 380
Phe Gly Gln Lys Met Lys Thr Ala Arg Ile Leu Ile Asn Thr Pro Ala
385                 390                 395                 400
Ser Gln Gly Gly Ile Gly Asp Leu Tyr Asn Phe Lys Leu Ala Pro Ser
                405                 410                 415
Leu Thr Leu Gly Cys Gly Ser Trp Gly Gly Asn Ser Ile Ser Glu Asn
                420                 425                 430
Val Gly Pro Lys His Leu Ile Asn Lys Lys Thr Val Ala Lys Arg Ala
                435                 440                 445
Glu Asn Met Leu Trp His Lys Leu Pro Lys Ser Ile Tyr Phe Arg Arg
450                 455                 460
```

```
Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
            485                 490                 495

Asp Gln Ile Thr Ser Val Leu Lys Ala Ala Gly Val Glu Thr Glu Val
        500                 505                 510

Phe Phe Glu Val Glu Ala Asp Pro Thr Leu Ser Ile Val Arg Lys Gly
    515                 520                 525

Ala Glu Leu Ala Asn Ser Phe Lys Pro Asp Val Ile Ala Leu Gly
530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
        595                 600                 605

Ala Val Val Thr Asp Asp Ala Thr Gly Gln Lys Tyr Pro Leu Ala Asp
    610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
            660                 665                 670

Gly Gln Ala Leu Gln Ala Leu Lys Leu Leu Lys Glu Tyr Leu Pro Ala
        675                 680                 685

Ser Tyr His Glu Gly Ser Lys Asn Pro Val Ala Arg Glu Arg Val His
    690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
        755                 760                 765

Pro Gln Ala Arg Arg Arg Tyr Ala Glu Ile Ala Asp His Leu Gly Leu
    770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Asp Gln Cys Thr Gly Ala Asn Pro Arg Tyr
        835                 840                 845

Pro Leu Ile Ser Glu Leu Lys Gln Ile Leu Leu Asp Thr Tyr Tyr Gly
    850                 855                 860

Arg Asp Tyr Val Glu Gly Glu Thr Ala Ala Lys Lys Glu Ala Ala Pro
865                 870                 875                 880
```

```
Ala Lys Ala Glu Lys Lys Ala Lys Lys Ser Ala
                885                 890

<210> SEQ ID NO 2
<211> LENGTH: 455
<212> TYPE: PRT
<213> ORGANISM: Lactobacillus plantarum

<400> SEQUENCE: 2

Met Leu Lys Glu Met Glu Glu Thr Thr Val Ser Arg Ser Ile Asp Arg
1               5                   10                  15

Leu Val Leu Asn Ala Ser Leu Ala Ala Asn Arg Leu Glu Val Met Asp
            20                  25                  30

Gln Ser Gln Val Asp Gln Ala Val Ala Met Ala Arg Ala Ala His
        35                  40                  45

Ala Ala Arg Gly Met Leu Ala Ala Met Ala Val Glu Glu Thr Gly Arg
    50                  55                  60

Gly Asn Tyr Arg Asp Lys Val Ala Lys Asn Asp Phe Ala Ala Lys Asn
65                  70                  75                  80

Val Tyr Asn Tyr Ile Lys Asp Lys Thr Val Gly Ile Ile Asn Asp
                85                  90                  95

Asp Pro Val Ser Gly Val Met Lys Val Ala Glu Pro Val Gly Ile Ile
                100                 105                 110

Ala Gly Val Thr Pro Val Thr Asn Pro Thr Ser Thr Val Ile Phe Asn
            115                 120                 125

Ala Met Leu Ala Leu Lys Thr Arg Asn Pro Ile Ile Phe Gly Phe His
    130                 135                 140

Pro Phe Ala Gln Lys Ser Cys Val Glu Thr Gly Arg Ile Ile Arg Asp
145                 150                 155                 160

Ala Ala Ile Ala Ser Gly Ala Pro Lys Asp Trp Ile Gln Trp Ile Lys
                165                 170                 175

Thr Pro Ser Leu Glu Ala Thr Asn Thr Leu Met Asn His Pro Gly Val
            180                 185                 190

Ala Thr Ile Ile Ala Thr Gly Gly Ala Gly Met Val Lys Thr Ala Tyr
        195                 200                 205

Ser Thr Gly Lys Pro Ala Leu Gly Val Gly Pro Gly Asn Val Pro Cys
    210                 215                 220

Phe Ile Glu Gln Thr Ala Asp Ile Gln Gln Ala Val Ser Asp Val Val
225                 230                 235                 240

Thr Ser Lys Ser Phe Asp Asn Gly Met Ile Cys Ala Ser Glu Ser Asn
                245                 250                 255

Leu Ile Val Ala Asp Gln Ile Tyr Asp Gln Val Lys Arg Glu Leu Ser
            260                 265                 270

His Asn Gly Val Tyr Phe Val Gly Thr Glu Asn Phe Lys Ala Leu Glu
        275                 280                 285

Ala Thr Val Met Asn Leu Asp Lys Gln Ala Val Asp Pro Lys Val Ala
    290                 295                 300

Gly Gln Thr Pro Trp Gln Ile Ala Gln Trp Ala Gly Phe Asp Val Pro
305                 310                 315                 320

Ser Asp Thr Lys Val Leu Ala Val Glu Leu Pro Ser Ile Gly Gly Asp
                325                 330                 335

Gln Val Leu Ser Arg Glu Lys Leu Ser Pro Val Leu Ala Val Val His
            340                 345                 350

Ala Lys Asp Thr Glu Ala Gly Phe Asn Leu Met Lys Arg Ser Leu Ala
        355                 360                 365
```

```
Leu Gly Gly Leu Gly His Thr Ala Ala Leu His Thr Thr Asp Glu Ala
    370                 375                 380

Val Met Asn Lys Phe Ala Leu Glu Met Thr Ala Cys Arg Ala Leu Ile
385                 390                 395                 400

Asn Val Pro Ser Ser Gln Gly Ala Ile Gly Tyr Lys Tyr Asp Asn Val
            405                 410                 415

Ala Pro Ser Leu Thr Leu Gly Cys Gly Thr Trp Gly His Asn Ser Ile
            420                 425                 430

Ser His Asn Leu Glu Asp Trp Asp Leu Leu Asn Ile Lys Thr Val Ala
            435                 440                 445

Lys Arg Leu Thr Lys Ile Arg
    450                 455

<210> SEQ ID NO 3
<211> LENGTH: 467
<212> TYPE: PRT
<213> ORGANISM: Escherichia coli

<400> SEQUENCE: 3

Met Asn Gln Gln Asp Ile Glu Gln Val Val Lys Ala Val Leu Leu Lys
1               5                   10                  15

Met Gln Ser Ser Asp Thr Pro Ser Ala Ala Val His Glu Met Gly Val
            20                  25                  30

Phe Ala Ser Leu Asp Asp Ala Val Ala Ala Lys Val Ala Gln Gln
            35                  40                  45

Gly Leu Lys Ser Val Ala Met Arg Gln Leu Ala Ile Ala Ala Ile Arg
    50                  55                  60

Glu Ala Gly Glu Lys His Ala Arg Asp Leu Ala Glu Leu Ala Val Ser
65                  70                  75                  80

Glu Thr Gly Met Gly Arg Val Glu Asp Lys Phe Ala Lys Asn Val Ala
                85                  90                  95

Gln Ala Arg Gly Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
        115                 120                 125

Val Ala Ser Val Thr Pro Ser Thr Asn Pro Ala Ala Thr Val Ile Asn
    130                 135                 140

Asn Ala Ile Ser Leu Ile Ala Ala Gly Asn Ser Val Ile Phe Ala Pro
145                 150                 155                 160

His Pro Ala Ala Lys Lys Val Ser Gln Arg Ala Ile Thr Leu Leu Asn
                165                 170                 175

Gln Ala Ile Val Ala Ala Gly Gly Pro Glu Asn Leu Leu Val Thr Val
            180                 185                 190

Ala Asn Pro Asp Ile Glu Thr Ala Gln Arg Leu Phe Lys Phe Pro Gly
        195                 200                 205

Ile Gly Leu Leu Val Val Thr Gly Gly Glu Ala Val Val Glu Ala Ala
    210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Ala Arg Ala Ala Gln Ser
                245                 250                 255

Ile Val Lys Gly Ala Ser Phe Asp Asn Asn Ile Ile Cys Ala Asp Glu
            260                 265                 270

Lys Val Leu Ile Val Val Asp Ser Val Ala Asp Glu Leu Met Arg Leu
```

```
            275                 280                 285
Met Glu Gly Gln His Ala Val Lys Leu Thr Ala Glu Gln Ala Gln Gln
290                 295                 300

Leu Gln Pro Val Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Lys Val Pro Gln Glu Thr Arg Leu Leu Phe Val Glu Thr
            340                 345                 350

Thr Ala Glu His Pro Phe Ala Val Thr Glu Leu Met Met Pro Val Leu
        355                 360                 365

Pro Val Val Arg Val Ala Asn Val Ala Asp Ala Ile Ala Leu Ala Val
370                 375                 380

Lys Leu Glu Gly Gly Cys His His Thr Ala Ala Met His Ser Arg Asn
385                 390                 395                 400

Ile Glu Asn Met Asn Gln Met Ala Asn Ala Ile Asp Thr Ser Ile Phe
                405                 410                 415

Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
        435                 440                 445

Ala Arg Thr Phe Val Arg Leu Arg Arg Cys Val Leu Val Asp Ala Phe
450                 455                 460

Arg Ile Val
465

<210> SEQ ID NO 4
<211> LENGTH: 469
<212> TYPE: PRT
<213> ORGANISM: Listeria innocua

<400> SEQUENCE: 4

Met Glu Ser Leu Glu Leu Glu Gln Leu Val Lys Val Leu Leu Glu
1               5                   10                  15

Lys Leu Ala Glu Gln Lys Glu Val Pro Thr Lys Thr Thr Thr Gln Gly
            20                  25                  30

Ala Lys Ser Gly Val Phe Asp Thr Val Asp Glu Ala Val Gln Ala Ala
        35                  40                  45

Val Ile Ala Gln Asn Cys Tyr Lys Glu Lys Ser Leu Glu Glu Arg Arg
    50                  55                  60

Asn Val Val Lys Ala Ile Arg Glu Ala Leu Tyr Pro Glu Ile Glu Thr
65                  70                  75                  80

Ile Ala Thr Arg Ala Val Ala Glu Thr Gly Met Gly Asn Val Thr Asp
                85                  90                  95

Lys Ile Leu Lys Asn Thr Leu Ala Ile Glu Lys Thr Pro Gly Val Glu
            100                 105                 110

Asp Leu Tyr Thr Glu Val Ala Thr Gly Asp Asn Gly Met Thr Leu Tyr
        115                 120                 125

Glu Leu Ser Pro Tyr Gly Val Ile Gly Ala Val Ala Pro Ser Thr Asn
    130                 135                 140

Pro Thr Glu Thr Leu Ile Cys Asn Ser Ile Gly Met Leu Ala Ala Gly
145                 150                 155                 160

Asn Ala Val Phe Tyr Ser Pro His Pro Gly Ala Lys Asn Ile Ser Leu
                165                 170                 175
```

```
Trp Leu Ile Glu Lys Leu Asn Thr Ile Val Arg Asp Ser Cys Gly Ile
                180                 185                 190

Asp Asn Leu Ile Val Thr Val Ala Lys Pro Ser Ile Gln Ala Ala Gln
            195                 200                 205

Glu Met Met Asn His Pro Lys Val Pro Leu Val Ile Thr Gly Gly
    210                 215                 220

Pro Gly Val Val Leu Gln Ala Met Gln Ser Gly Lys Lys Val Ile Gly
225                 230                 235                 240

Ala Gly Ala Gly Asn Pro Pro Ser Ile Val Asp Glu Thr Ala Asn Ile
                245                 250                 255

Glu Lys Ala Ala Ala Asp Ile Val Asp Gly Ala Ser Phe Asp His Asn
            260                 265                 270

Ile Leu Cys Ile Ala Glu Lys Ser Val Val Ala Val Asp Ser Ile Ala
        275                 280                 285

Asp Phe Leu Leu Phe Gln Met Glu Lys Asn Gly Ala Leu His Val Thr
    290                 295                 300

Asn Pro Ser Asp Ile Gln Lys Leu Glu Lys Val Ala Val Thr Asp Lys
305                 310                 315                 320

Gly Val Thr Asn Lys Lys Leu Val Gly Lys Ser Ala Thr Glu Ile Leu
                325                 330                 335

Lys Glu Ala Gly Ile Ala Cys Asp Phe Thr Pro Arg Leu Ile Ile Val
            340                 345                 350

Glu Thr Glu Lys Ser His Pro Phe Ala Thr Val Glu Leu Leu Met Pro
        355                 360                 365

Ile Val Pro Val Val Arg Val Pro Asp Phe Asp Glu Ala Leu Glu Val
    370                 375                 380

Ala Ile Glu Leu Glu Gln Gly Leu His His Thr Ala Thr Met His Ser
385                 390                 395                 400

Gln Asn Ile Ser Arg Leu Asn Lys Ala Ala Arg Asp Met Gln Thr Ser
                405                 410                 415

Ile Phe Val Lys Asn Gly Pro Ser Phe Ala Gly Leu Gly Phe Arg Gly
            420                 425                 430

Glu Gly Ser Thr Thr Phe Thr Ile Ala Thr Pro Thr Gly Glu Gly Thr
        435                 440                 445

Thr Thr Ala Arg His Phe Ala Arg Arg Arg Cys Val Leu Thr Asp
    450                 455                 460

Gly Phe Ser Ile Arg
465

<210> SEQ ID NO 5
<211> LENGTH: 869
<212> TYPE: PRT
<213> ORGANISM: Staphylococcus aureus

<400> SEQUENCE: 5

Met Leu Thr Ile Pro Glu Lys Glu Asn Arg Gly Ser Lys Glu Gln Glu
1               5                   10                  15

Val Ala Ile Met Ile Asp Ala Leu Ala Asp Lys Gly Lys Lys Ala Leu
            20                  25                  30

Glu Ala Leu Ser Lys Lys Ser Gln Glu Glu Ile Asp His Ile Val His
        35                  40                  45

Gln Met Ser Leu Ala Ala Val Asp Gln His Met Val Leu Ala Lys Leu
    50                  55                  60

Ala His Glu Glu Thr Gly Arg Gly Ile Tyr Glu Asp Lys Ala Ile Lys
65                  70                  75                  80
```

```
Asn Leu Tyr Ala Ser Glu Tyr Ile Trp Asn Ser Ile Lys Asp Asn Lys
                85                  90                  95

Thr Val Gly Ile Ile Gly Glu Asp Lys Glu Lys Gly Leu Thr Tyr Val
            100                 105                 110

Ala Glu Pro Ile Gly Val Ile Cys Gly Val Thr Pro Thr Thr Asn Pro
            115                 120                 125

Thr Ser Thr Thr Ile Phe Lys Ala Met Ile Ala Ile Lys Thr Gly Asn
        130                 135                 140

Pro Ile Ile Phe Ala Phe His Pro Ser Ala Gln Glu Ser Ser Lys Arg
145                 150                 155                 160

Ala Ala Glu Val Val Leu Glu Ala Ala Met Lys Ala Gly Ala Pro Lys
                165                 170                 175

Asp Ile Ile Gln Trp Ile Glu Val Pro Ser Ile Glu Ala Thr Lys Gln
            180                 185                 190

Leu Met Asn His Lys Gly Ile Ala Leu Val Leu Ala Thr Gly Gly Ser
        195                 200                 205

Gly Met Val Lys Ser Ala Tyr Ser Thr Gly Lys Pro Ala Leu Gly Val
    210                 215                 220

Gly Pro Gly Asn Val Pro Ser Tyr Ile Glu Lys Thr Ala His Ile Lys
225                 230                 235                 240

Arg Ala Val Asn Asp Ile Ile Gly Ser Lys Thr Phe Asp Asn Gly Met
                245                 250                 255

Ile Cys Ala Ser Glu Gln Val Val Ile Asp Lys Glu Ile Tyr Lys
            260                 265                 270

Asp Val Thr Asn Glu Phe Lys Ala His Gln Ala Tyr Phe Val Lys Lys
        275                 280                 285

Asp Glu Leu Gln Arg Leu Glu Asn Ala Ile Met Asn Glu Gln Lys Thr
    290                 295                 300

Gly Ile Lys Pro Asp Ile Val Gly Lys Ser Ala Val Glu Ile Ala Glu
305                 310                 315                 320

Leu Ala Gly Ile Pro Val Pro Glu Asn Thr Lys Leu Ile Ile Ala Glu
                325                 330                 335

Ile Ser Gly Val Gly Ser Asp Tyr Pro Leu Ser Arg Glu Lys Leu Ser
            340                 345                 350

Pro Val Leu Ala Leu Val Lys Ala Gln Ser Thr Lys Gln Ala Phe Gln
        355                 360                 365

Ile Cys Glu Asp Thr Leu His Phe Gly Gly Leu Gly His Thr Ala Val
    370                 375                 380

Ile His Thr Glu Asp Glu Thr Leu Gln Lys Asp Phe Gly Leu Arg Met
385                 390                 395                 400

Lys Ala Cys Arg Val Leu Val Asn Thr Pro Ser Ala Val Gly Gly Ile
                405                 410                 415

Gly Asp Met Tyr Asn Glu Leu Ile Pro Ser Leu Thr Leu Gly Cys Gly
            420                 425                 430

Ser Tyr Gly Arg Asn Ser Ile Ser His Asn Val Ser Ala Thr Asp Leu
        435                 440                 445

Leu Asn Ile Lys Thr Ile Ala Lys Arg Arg Asn Asn Thr Gln Ile Phe
    450                 455                 460

Lys Val Pro Ala Gln Ile Tyr Phe Glu Glu Asn Ala Ile Met Ser Leu
465                 470                 475                 480

Thr Thr Met Asp Lys Ile Glu Lys Val Met Ile Val Cys Asp Pro Gly
                485                 490                 495
```

Met Val Glu Phe Gly Tyr Thr Lys Thr Val Glu Asn Val Leu Arg Gln
            500                 505                 510

Arg Thr Glu Gln Pro Gln Ile Lys Ile Phe Ser Glu Val Glu Pro Asn
        515                 520                 525

Pro Ser Thr Asn Thr Val Tyr Lys Gly Leu Glu Met Met Val Asp Phe
    530                 535                 540

Gln Pro Asp Thr Ile Ile Ala Leu Gly Gly Ser Ala Met Asp Ala
545                 550                 555                 560

Ala Lys Ala Met Trp Met Phe Phe Glu His Pro Glu Thr Ser Phe Phe
                565                 570                 575

Gly Ala Lys Gln Lys Phe Leu Asp Ile Gly Lys Arg Thr Tyr Lys Ile
            580                 585                 590

Gly Met Pro Glu Asn Ala Thr Phe Ile Cys Ile Pro Thr Thr Ser Gly
        595                 600                 605

Thr Gly Ser Glu Val Thr Pro Phe Ala Val Ile Thr Asp Ser Glu Thr
    610                 615                 620

Asn Val Lys Tyr Pro Leu Ala Asp Phe Ala Leu Thr Pro Asp Val Ala
625                 630                 635                 640

Ile Ile Asp Pro Gln Phe Val Met Ser Val Pro Lys Ser Val Thr Ala
                645                 650                 655

Asp Thr Gly Met Asp Val Leu Thr His Ala Met Glu Ser Tyr Val Ser
            660                 665                 670

Val Met Ala Ser Asp Tyr Thr Arg Gly Leu Ser Leu Gln Ala Ile Lys
        675                 680                 685

Leu Thr Phe Glu Tyr Leu Lys Ser Ser Val Glu Lys Gly Asp Lys Val
    690                 695                 700

Ser Arg Glu Lys Met His Asn Ala Ser Thr Leu Ala Gly Met Ala Phe
705                 710                 715                 720

Ala Asn Ala Phe Leu Gly Ile Ala His Ser Ile Ala His Lys Ile Gly
                725                 730                 735

Gly Glu Tyr Gly Ile Pro His Gly Arg Ala Asn Ala Ile Leu Leu Pro
            740                 745                 750

His Ile Ile Arg Tyr Asn Ala Lys Asp Pro Gln Lys His Ala Leu Phe
        755                 760                 765

Pro Lys Tyr Glu Phe Phe Arg Ala Asp Thr Asp Tyr Ala Asp Ile Ala
    770                 775                 780

Lys Phe Leu Gly Leu Lys Gly Asn Thr Thr Glu Ala Leu Val Glu Ser
785                 790                 795                 800

Leu Ala Lys Ala Val Tyr Glu Leu Gly Gln Ser Val Gly Ile Glu Met
                805                 810                 815

Asn Leu Lys Ser Gln Gly Val Ser Glu Glu Leu Asn Glu Ser Ile
            820                 825                 830

Asp Arg Met Ala Glu Leu Ala Phe Glu Asp Gln Cys Thr Thr Ala Asn
        835                 840                 845

Pro Lys Glu Ala Leu Ile Ser Glu Ile Lys Asp Ile Ile Gln Thr Ser
    850                 855                 860

Tyr Asp Tyr Lys Gln
865

<210> SEQ ID NO 6
<211> LENGTH: 683
<212> TYPE: PRT
<213> ORGANISM: Saccharomyces cerevisiae

<400> SEQUENCE: 6

```
Met Thr Ile Lys Glu His Lys Val Val Tyr Glu Ala His Asn Val Lys
1               5                   10                  15

Ala Leu Lys Ala Pro Gln His Phe Tyr Asn Ser Gln Pro Gly Lys Gly
                20                  25                  30

Tyr Val Thr Asp Met Gln His Tyr Gln Glu Met Tyr Gln Gln Ser Ile
            35                  40                  45

Asn Glu Pro Glu Lys Phe Phe Asp Lys Met Ala Lys Glu Tyr Leu His
        50                  55                  60

Trp Asp Ala Pro Tyr Thr Lys Val Gln Ser Gly Ser Leu Asn Asn Gly
65                  70                  75                  80

Asp Val Ala Trp Phe Leu Asn Gly Lys Leu Asn Ala Ser Tyr Asn Cys
                85                  90                  95

Val Asp Arg His Ala Phe Ala Asn Pro Asp Lys Pro Ala Leu Ile Tyr
                100                 105                 110

Glu Ala Asp Asp Glu Ser Asp Asn Lys Ile Ile Thr Phe Gly Glu Leu
                115                 120                 125

Leu Arg Lys Val Ser Gln Ile Ala Gly Val Leu Lys Ser Trp Gly Val
        130                 135                 140

Lys Lys Gly Asp Thr Val Ala Ile Tyr Leu Pro Met Ile Pro Glu Ala
145                 150                 155                 160

Val Ile Ala Met Leu Ala Val Ala Arg Ile Gly Ala Ile His Ser Val
                165                 170                 175

Val Phe Ala Gly Phe Ser Ala Gly Ser Leu Lys Asp Arg Val Val Asp
                180                 185                 190

Ala Asn Ser Lys Val Val Ile Thr Cys Asp Glu Gly Lys Arg Gly Gly
        195                 200                 205

Lys Thr Ile Asn Thr Lys Lys Ile Val Asp Glu Gly Leu Asn Gly Val
210                 215                 220

Asp Leu Val Ser Arg Ile Leu Val Phe Gln Arg Thr Gly Thr Glu Gly
225                 230                 235                 240

Ile Pro Met Lys Ala Gly Arg Asp Tyr Trp Trp His Glu Glu Ala Ala
                245                 250                 255

Lys Gln Arg Thr Tyr Leu Pro Pro Val Ser Cys Asp Ala Glu Asp Pro
                260                 265                 270

Leu Phe Leu Leu Tyr Thr Ser Gly Ser Thr Gly Ser Pro Lys Gly Val
        275                 280                 285

Val His Thr Thr Gly Gly Tyr Leu Leu Gly Ala Ala Leu Thr Thr Arg
        290                 295                 300

Tyr Val Phe Asp Ile His Pro Glu Asp Val Leu Phe Thr Ala Gly Asp
305                 310                 315                 320

Val Gly Trp Ile Thr Gly His Thr Tyr Ala Leu Tyr Gly Pro Leu Thr
                325                 330                 335

Leu Gly Thr Ala Ser Ile Ile Phe Glu Ser Thr Pro Ala Tyr Pro Asp
            340                 345                 350

Tyr Gly Arg Tyr Trp Arg Ile Ile Gln Arg His Lys Ala Thr His Phe
            355                 360                 365

Tyr Val Ala Pro Thr Ala Leu Arg Leu Ile Lys Arg Val Gly Glu Ala
        370                 375                 380

Glu Ile Ala Lys Tyr Asp Thr Ser Ser Leu Arg Val Leu Gly Ser Val
385                 390                 395                 400

Gly Glu Pro Ile Ser Pro Asp Leu Trp Glu Trp Tyr His Glu Lys Val
                405                 410                 415
```

Gly Asn Lys Asn Cys Val Ile Cys Asp Thr Met Trp Gln Thr Glu Ser
            420                 425                 430

Gly Ser His Leu Ile Ala Pro Leu Ala Gly Ala Val Pro Thr Lys Pro
        435                 440                 445

Gly Ser Ala Thr Val Pro Phe Phe Gly Ile Asn Ala Cys Ile Ile Asp
    450                 455                 460

Pro Val Thr Gly Val Glu Leu Glu Gly Asn Asp Val Glu Gly Val Leu
465                 470                 475                 480

Ala Val Lys Ser Pro Trp Pro Ser Met Ala Arg Ser Val Trp Asn His
                485                 490                 495

His Asp Arg Tyr Met Asp Thr Tyr Leu Lys Pro Tyr Pro Gly His Tyr
            500                 505                 510

Phe Thr Gly Asp Gly Ala Gly Arg Asp His Asp Gly Tyr Tyr Trp Ile
        515                 520                 525

Arg Gly Arg Val Asp Asp Val Val Asn Val Ser Gly His Arg Leu Ser
    530                 535                 540

Thr Ser Glu Ile Glu Ala Ser Ile Ser Asn His Glu Asn Val Ser Glu
545                 550                 555                 560

Ala Ala Val Val Gly Ile Pro Asp Glu Leu Thr Gly Gln Thr Val Val
                565                 570                 575

Ala Tyr Val Ser Leu Lys Asp Gly Tyr Leu Gln Asn Asn Ala Thr Glu
            580                 585                 590

Gly Asp Ala Glu His Ile Thr Pro Asp Asn Leu Arg Arg Glu Leu Ile
        595                 600                 605

Leu Gln Val Arg Gly Glu Ile Gly Pro Phe Ala Ser Pro Lys Thr Ile
610                 615                 620

Ile Leu Val Arg Asp Leu Pro Arg Thr Arg Ser Gly Lys Ile Met Arg
625                 630                 635                 640

Arg Val Leu Arg Lys Val Ala Ser Asn Glu Ala Glu Gln Leu Gly Asp
                645                 650                 655

Leu Thr Thr Leu Ala Asn Pro Glu Val Val Pro Ala Ile Ile Ser Ala
            660                 665                 670

Val Glu Asn Gln Phe Phe Ser Gln Lys Lys Lys
        675                 680

<210> SEQ ID NO 7
<211> LENGTH: 367
<212> TYPE: PRT
<213> ORGANISM: Escherichia coli

<400> SEQUENCE: 7

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
            115                 120                 125

Val Ile Tyr Thr Asp Glu Gly Glu Phe Asp Arg Tyr Leu Leu Leu Pro
        130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Leu Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
        275                 280                 285

Pro Val Glu Glu Ile Glu Thr Val Ala Ala Leu Ser His Ala Val Gly
    290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
        355                 360                 365

<210> SEQ ID NO 8
<211> LENGTH: 365
<212> TYPE: PRT
<213> ORGANISM: Klebsiella pneumoniae

<400> SEQUENCE: 8

Met Leu Lys Val Ile Gln Ser Pro Ala Lys Tyr Leu Gln Gly Pro Asp
1               5                   10                  15

Ala Ala Val Leu Phe Gly Gln Tyr Ala Lys Asn Leu Ala Glu Ser Phe
            20                  25                  30

Phe Val Ile Ala Asp Asp Phe Val Met Lys Leu Ala Gly Glu Lys Val
        35                  40                  45

Val Asn Gly Leu Gln Ser His Asp Ile Arg Cys His Ala Glu Arg Phe
    50                  55                  60

Asn Gly Glu Cys Ser His Ala Glu Ile Asn Arg Leu Met Ala Ile Leu
65                  70                  75                  80

Gln Lys Gln Gly Cys Arg Gly Val Val Gly Ile Gly Gly Gly Lys Thr
                85                  90                  95

Leu Asp Thr Ala Lys Ala Ile Gly Tyr Tyr Gln Lys Leu Pro Val Val
            100                 105                 110

Val Ile Pro Thr Ile Ala Ser Thr Asp Ala Pro Thr Ser Ala Leu Ser

```
            115                 120                 125
Val Ile Tyr Thr Glu Ala Gly Glu Phe Glu Glu Tyr Leu Ile Tyr Pro
    130                 135                 140

Lys Asn Pro Asp Met Val Val Met Asp Thr Ala Ile Ala Lys Ala
145                 150                 155                 160

Pro Val Arg Leu Leu Val Ser Gly Met Gly Asp Ala Leu Ser Thr Trp
                165                 170                 175

Phe Glu Ala Lys Ala Cys Tyr Asp Ala Arg Ala Thr Ser Met Ala Gly
            180                 185                 190

Gly Gln Ser Thr Glu Ala Ala Leu Ser Leu Ala Arg Leu Cys Tyr Asp
        195                 200                 205

Thr Leu Leu Ala Glu Gly Glu Lys Ala Arg Leu Ala Ala Gln Ala Gly
    210                 215                 220

Val Val Thr Glu Ala Leu Glu Arg Ile Ile Glu Ala Asn Thr Tyr Leu
225                 230                 235                 240

Ser Gly Ile Gly Phe Glu Ser Ser Gly Leu Ala Ala His Ala Ile
                245                 250                 255

His Asn Gly Phe Thr Ile Leu Glu Glu Cys His His Leu Tyr His Gly
            260                 265                 270

Glu Lys Val Ala Phe Gly Thr Leu Ala Gln Leu Val Leu Gln Asn Ser
        275                 280                 285

Pro Met Asp Glu Ile Glu Thr Val Leu Gly Phe Cys Gln Arg Val Gly
    290                 295                 300

Leu Pro Val Thr Leu Ala Gln Met Gly Val Lys Glu Gly Ile Asp Ala
305                 310                 315                 320

Lys Ile Ala Ala Val Ala Lys Ala Thr Cys Ala Glu Gly Glu Thr Ile
                325                 330                 335

His Asn Met Pro Phe Ala Val Thr Pro Glu Ser Val His Ala Ala Ile
            340                 345                 350

Leu Thr Ala Asp Leu Leu Gly Gln Gln Trp Leu Ala Arg
        355                 360                 365

<210> SEQ ID NO 9
<211> LENGTH: 367
<212> TYPE: PRT
<213> ORGANISM: Enterobacter aerogenes

<400> SEQUENCE: 9

Met Asp Arg Ile Ile Gln Ser Pro Gly Lys Tyr Ile Gln Gly Ala Gly
1               5                   10                  15

Ala Ile Lys Arg Leu Gly Glu Tyr Leu Lys Pro Leu Ala Glu Arg Trp
                20                  25                  30

Leu Ile Ile Gly Asp Lys Phe Val Leu Gly Phe Ala Glu Glu Gln Leu
            35                  40                  45

Arg Thr Ser Leu Gly Gly Ala Gly Leu Val Ala Glu Ile Ala Pro Phe
        50                  55                  60

Gly Gly Glu Cys Ser Gln Asn Glu Ile Asn Arg Leu Arg Asp Ile Ala
65                  70                  75                  80

Ser Ser Ala Gln Cys His Ala Val Leu Gly Ile Gly Gly Gly Lys Thr
                85                  90                  95

Leu Asp Thr Ala Lys Ala Leu Ala His Tyr Met His Leu Pro Val Val
            100                 105                 110

Val Ala Pro Thr Ile Ala Ser Thr Asp Ala Pro Cys Ser Ala Leu Ser
        115                 120                 125
```

Val Ile Tyr Thr Asp Asp Gly Glu Phe Glu Ser Tyr Leu Met Leu Pro
130                 135                 140

His Asn Pro Asn Met Val Val Asp Thr Gln Ile Val Ala Ala Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
                180                 185                 190

Gly Lys Cys Thr Gln Ala Ala Leu Ala Leu Ala Glu Leu Cys Tyr Asn
            195                 200                 205

Thr Leu Val Glu Glu Gly Glu Lys Ala Met Leu Ala Ala Glu Gln His
210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala His Ala Ile
                245                 250                 255

His Asn Gly Leu Thr Ala Ile Pro Asp Ala His His Phe Tyr His Gly
                260                 265                 270

Glu Lys Val Ala Phe Gly Thr Leu Thr Gln Leu Val Leu Glu Asn Ala
            275                 280                 285

Pro Val Glu Glu Ile Glu Thr Ala Ala Leu Cys His Ser Val Gly
290                 295                 300

Leu Pro Ile Thr Leu Ala Gln Leu Asp Ile Lys Gly Asp Ile Pro Ala
305                 310                 315                 320

Lys Met Arg Thr Val Ala Glu Ala Ala Cys Ala Glu Gly Glu Thr Ile
                325                 330                 335

His Asn Met Pro Gly Gly Ala Cys Ala Asp Gln Val Tyr Ala Ala Leu
                340                 345                 350

Leu Val Ala Asp Gln Tyr Gly Gln Arg Phe Leu Gln Glu Trp Glu
            355                 360                 365

<210> SEQ ID NO 10
<211> LENGTH: 364
<212> TYPE: PRT
<213> ORGANISM: Yersinia aldovae

<400> SEQUENCE: 10

Met Leu Lys Val Ile Gln Ser Pro Ser Lys Tyr Ile Gln Gly Ala Asn
1               5                   10                  15

Ala Leu Gln Ser Ile Gly Glu Phe Ala Lys Leu Leu Ala Asn Asn Tyr
                20                  25                  30

Phe Ile Ile Ala Asp Asp Phe Val Met Lys Leu Thr Ala Asp Thr Val
            35                  40                  45

Gly Thr Ser Leu Gln Thr Cys Glu Leu Lys Ser His Phe Ser Arg Phe
50                  55                  60

Asn Gly Glu Cys Ser Arg Gln Glu Ile Glu Arg Leu Thr Val Glu Leu
65                  70                  75                  80

Lys Lys Tyr Gly Cys Asn Gly Val Ile Gly Ile Gly Gly Gly Lys Thr
                85                  90                  95

Leu Asp Thr Ala Lys Ala Ile Ala His Tyr Gln His Ile Pro Val Val
            100                 105                 110

Val Val Pro Thr Ile Ala Ser Thr Asp Ala Pro Thr Ser Ala Leu Ser
            115                 120                 125

Val Ile Tyr Thr Glu Gln Gly Glu Phe Ala Glu Tyr Leu Ile Tyr Pro
130                 135                 140

```
Lys Asn Pro Asp Ile Val Leu Met Asp Thr Thr Ile Ile Ala Lys Ala
145                 150                 155                 160

Pro Val Arg Leu Leu Val Ala Gly Met Gly Asp Ala Leu Ser Thr Tyr
                165                 170                 175

Phe Glu Ala Gln Ala Cys Phe Asp Ala Lys Ala Ile Ser Met Ala Gly
            180                 185                 190

Gly Ala Ser Thr Leu Ala Ala Ile Thr Leu Ala Arg Leu Cys Tyr Glu
        195                 200                 205

Thr Leu Leu Ala Glu Gly Tyr Lys Ala Lys Leu Ala Val Glu Ala Gly
    210                 215                 220

Val Val Thr Glu Ala Val Glu Arg Ile Ile Glu Ala Asn Thr Tyr Leu
225                 230                 235                 240

Ser Gly Ile Gly Phe Glu Ser Ser Gly Leu Ala Ala His Ala Ile
                245                 250                 255

His Asn Gly Phe Thr Val Leu Glu Glu Cys His His Leu Tyr His Gly
                260                 265                 270

Glu Lys Val Ala Phe Gly Thr Leu Thr Gln Leu Val Leu Gln Asn Ser
            275                 280                 285

Ser Met Glu Glu Ile Glu Thr Val Leu Ser Phe Cys Gln Gln Leu Gly
        290                 295                 300

Leu Pro Ile Thr Leu Ala Glu Met Gly Val Thr Gln Asp Leu Glu Cys
305                 310                 315                 320

Lys Ile Arg Ala Val Ala Gln Ala Ser Cys Ala Glu Gly Glu Thr Ile
                325                 330                 335

His Asn Met Pro Phe Lys Val Thr Ala Asp Ser Val Tyr Ala Ala Ile
                340                 345                 350

Ile Val Ala Asp Arg Leu Gly Gln Ala Phe Leu Asn
                355                 360

<210> SEQ ID NO 11
<211> LENGTH: 584
<212> TYPE: PRT
<213> ORGANISM: Saccharomyces cerevisiae

<400> SEQUENCE: 11

Met Ser Ala Lys Ser Phe Glu Val Thr Asp Pro Val Asn Ser Ser Leu
1               5                   10                  15

Lys Gly Phe Ala Leu Ala Asn Pro Ser Ile Thr Leu Val Pro Glu Glu
                20                  25                  30

Lys Ile Leu Phe Arg Lys Thr Asp Ser Asp Lys Ile Ala Leu Ile Ser
            35                  40                  45

Gly Gly Gly Ser Gly His Glu Pro Thr His Ala Gly Phe Ile Gly Lys
        50                  55                  60

Gly Met Leu Ser Gly Ala Val Val Gly Glu Ile Phe Ala Ser Pro Ser
65                  70                  75                  80

Thr Lys Gln Ile Leu Asn Ala Ile Arg Leu Val Asn Glu Asn Ala Ser
                85                  90                  95

Gly Val Leu Leu Ile Val Lys Asn Tyr Thr Gly Asp Val Leu His Phe
            100                 105                 110

Gly Leu Ser Ala Glu Arg Ala Arg Ala Leu Gly Ile Asn Cys Arg Val
        115                 120                 125

Ala Val Ile Gly Asp Asp Val Ala Val Gly Arg Glu Lys Gly Gly Met
    130                 135                 140

Val Gly Arg Arg Ala Leu Ala Gly Thr Val Leu Val His Lys Ile Val
```

```
145                 150                 155                 160
Gly Ala Phe Ala Glu Glu Tyr Ser Ser Lys Tyr Gly Leu Asp Gly Thr
                165                 170                 175

Ala Lys Val Ala Lys Ile Ile Asn Asp Asn Leu Val Thr Ile Gly Ser
                180                 185                 190

Ser Leu Asp His Cys Lys Val Pro Gly Arg Lys Phe Glu Ser Glu Leu
                195                 200                 205

Asn Glu Lys Gln Met Glu Leu Gly Met Gly Ile His Asn Glu Pro Gly
                210                 215                 220

Val Lys Val Leu Asp Pro Ile Pro Ser Thr Glu Asp Leu Ile Ser Lys
225                 230                 235                 240

Tyr Met Leu Pro Lys Leu Leu Asp Pro Asn Asp Lys Asp Arg Ala Phe
                245                 250                 255

Val Lys Phe Asp Glu Asp Asp Glu Val Val Leu Leu Val Asn Asn Leu
                260                 265                 270

Gly Gly Val Ser Asn Phe Val Ile Ser Ser Ile Thr Ser Lys Thr Thr
                275                 280                 285

Asp Phe Leu Lys Glu Asn Tyr Asn Ile Thr Pro Val Gln Thr Ile Ala
290                 295                 300

Gly Thr Leu Met Thr Ser Phe Asn Gly Asn Gly Phe Ser Ile Thr Leu
305                 310                 315                 320

Leu Asn Ala Thr Lys Ala Thr Lys Ala Leu Gln Ser Asp Phe Glu Glu
                325                 330                 335

Ile Lys Ser Val Leu Asp Leu Leu Asn Ala Phe Thr Asn Ala Pro Gly
                340                 345                 350

Trp Pro Ile Ala Asp Phe Glu Lys Thr Ser Ala Pro Ser Val Asn Asp
                355                 360                 365

Asp Leu Leu His Asn Glu Val Thr Ala Lys Ala Val Gly Thr Tyr Asp
                370                 375                 380

Phe Asp Lys Phe Ala Glu Trp Met Lys Ser Gly Ala Glu Gln Val Ile
385                 390                 395                 400

Lys Ser Glu Pro His Ile Thr Glu Leu Asp Asn Gln Val Gly Asp Gly
                405                 410                 415

Asp Cys Gly Tyr Thr Leu Val Ala Gly Val Lys Gly Ile Thr Glu Asn
                420                 425                 430

Leu Asp Lys Leu Ser Lys Asp Ser Leu Ser Gln Ala Val Ala Gln Ile
                435                 440                 445

Ser Asp Phe Ile Glu Gly Ser Met Gly Gly Thr Ser Gly Gly Leu Tyr
                450                 455                 460

Ser Ile Leu Leu Ser Gly Phe Ser His Gly Leu Ile Gln Val Cys Lys
465                 470                 475                 480

Ser Lys Asp Glu Pro Val Thr Lys Glu Ile Val Ala Lys Ser Leu Gly
                485                 490                 495

Ile Ala Leu Asp Thr Leu Tyr Lys Tyr Thr Lys Ala Arg Lys Gly Ser
                500                 505                 510

Ser Thr Met Ile Asp Ala Leu Glu Pro Phe Val Lys Glu Phe Thr Ala
                515                 520                 525

Ser Lys Asp Phe Asn Lys Ala Val Lys Ala Ala Glu Glu Gly Ala Lys
                530                 535                 540

Ser Thr Ala Thr Phe Glu Ala Lys Phe Gly Arg Ala Ser Tyr Val Gly
545                 550                 555                 560

Asp Ser Ser Gln Val Glu Asp Pro Gly Ala Val Gly Leu Cys Glu Phe
                565                 570                 575
```

Leu Lys Gly Val Gln Ser Ala Leu
            580

<210> SEQ ID NO 12
<211> LENGTH: 356
<212> TYPE: PRT
<213> ORGANISM: Klebsiella pneumoniae

<400> SEQUENCE: 12

Met Lys Lys Leu Ile Asn Arg Val Glu Asp Val Leu Asn Glu Gln Leu
1               5                   10                  15

Gln Gly Leu Ala Lys Ala His Pro Gln Leu Thr Leu His Gln Asp Pro
            20                  25                  30

Leu Tyr Val Thr Arg Thr Asp Ala Pro Val Ala Gly Lys Val Ala Leu
        35                  40                  45

Leu Ser Gly Gly Gly Ser Gly His Glu Pro Met His Cys Gly Tyr Ile
    50                  55                  60

Gly Gln Gly Met Leu Ser Gly Ala Cys Pro Gly Glu Ile Phe Thr Ser
65                  70                  75                  80

Pro Thr Pro Asp Lys Met Phe Glu Cys Ala Met Gln Ile Asp Gly Gly
                85                  90                  95

Glu Gly Val Leu Leu Ile Ile Lys Asn Tyr Thr Gly Asp Ile Leu Asn
            100                 105                 110

Phe Glu Thr Ala Thr Glu Leu Leu His Glu Ser Gly Ile Lys Val Thr
        115                 120                 125

Thr Val Val Val Asp Asp Asp Val Ala Val Lys Asp Ser Leu Tyr Thr
    130                 135                 140

Ala Gly Arg Arg Gly Val Ala Asn Thr Val Leu Ile Glu Lys Leu Val
145                 150                 155                 160

Gly Ala Ala Ala Glu Arg Gly Asp Ser Leu Glu Ala Cys Ala Glu Leu
                165                 170                 175

Gly Arg Arg Leu Asn Asn Leu Gly His Ser Ile Gly Ile Ala Leu Gly
            180                 185                 190

Ala Cys Thr Val Pro Ala Ala Gly Gln Pro Ser Phe Thr Leu Lys Asp
        195                 200                 205

Asp Glu Met Glu Phe Gly Val Gly Ile His Gly Glu Pro Gly Ile Asp
    210                 215                 220

Arg Arg Arg Phe Ser Ser Leu Asp Gln Thr Val Asp Glu Met Phe Asp
225                 230                 235                 240

Thr Leu Leu Glu Asn Gly Ala Tyr Ser Arg Thr Leu Arg Gln Trp Asp
                245                 250                 255

Thr Val Lys Gly Ala Trp Gln Glu Val Lys Gln Ser Lys Thr Ala Leu
            260                 265                 270

Gln Asn Gly Asp Arg Val Ile Ala Leu Val Asn Asn Leu Gly Ala Thr
        275                 280                 285

Pro Leu Ser Glu Leu Tyr Gly Val Tyr His Arg Leu Ala Gln Arg Cys
    290                 295                 300

Glu Ala Ser Gly Ile Ile Ile Glu Arg Asn Leu Ile Gly Ser Tyr Cys
305                 310                 315                 320

Thr Ser Leu Asp Met Ser Gly Phe Ser Ile Thr Leu Leu Lys Val Asp
                325                 330                 335

Asp Glu Thr Leu Thr Leu Trp Asp Ala Pro Val His Thr Pro Ala Leu
            340                 345                 350

Asn Trp Gly Asn

355

<210> SEQ ID NO 13
<211> LENGTH: 572
<212> TYPE: PRT
<213> ORGANISM: Yarrowia lipolytica

<400> SEQUENCE: 13

```
Met Thr Thr Lys Gln Phe Gln Phe Asp Ser Asp Pro Leu Asn Ser Ala
1               5                   10                  15

Leu Ala Ala Thr Ala Glu Ala Ser Gly Leu Ala Tyr Leu Pro Lys Ser
            20                  25                  30

Lys Val Ile Tyr Tyr Pro Leu Thr Asn Asp Lys Val Thr Leu Ile Ser
        35                  40                  45

Gly Gly Gly Ala Gly His Glu Pro Ala Gln Thr Gly Phe Val Gly Pro
    50                  55                  60

Gly Leu Leu Asp Ala Ala Val Ser Gly Gln Ile Phe Ala Ser Pro Ser
65                  70                  75                  80

Thr Lys Gln Ile Ile Ala Gly Val Asn Ala Val Lys Ser Gln Arg Gly
                85                  90                  95

Ser Ile Ile Ile Val Met Asn Tyr Thr Gly Asp Val Ile His Phe Gly
            100                 105                 110

Met Ala Ala Glu Gln Leu Arg Ser Arg Tyr Asp Tyr His Ala Glu Leu
        115                 120                 125

Val Ser Ile Gly Asp Asp Ile Ser Val Asn Lys Lys Ala Gly Arg Arg
    130                 135                 140

Gly Leu Ala Gly Thr Val Leu Val His Lys Ile Ala Gly His Leu Ala
145                 150                 155                 160

Arg Asp Gly Trp Asp Val Gly Val Leu Ala Glu Ala Leu Arg Thr Thr
                165                 170                 175

Ala Ala Asn Leu Ala Thr Val Ala Ala Ser Leu Glu His Cys Thr Val
            180                 185                 190

Pro Gly Arg Lys Phe Glu Thr Glu Leu Ala Ala Asp Glu Met Glu Ile
        195                 200                 205

Gly Met Gly Ile His Asn Glu Pro Gly Val Lys Thr Ile Lys Ile Gly
    210                 215                 220

Lys Val Glu Ser Leu Leu Asp Glu Leu Val Asp Lys Phe Glu Pro Ser
225                 230                 235                 240

Lys Gln Asp Phe Val Pro Phe Asn Lys Gly Asp Glu Val Val Leu Leu
                245                 250                 255

Val Asn Ser Leu Gly Gly Val Ser Ser Leu Glu Leu His Ala Ile Ala
            260                 265                 270

Asn Ile Ala Gln Thr Lys Phe Glu Lys Val Leu Gly Val Lys Thr Val
        275                 280                 285

Arg Leu Ile Val Gly Asn Phe Met Ala Ala Phe Asn Gly Pro Gly Phe
    290                 295                 300

Ser Leu Thr Leu Leu Asn Val Thr Thr Thr Ala Lys Lys Gly Asn Phe
305                 310                 315                 320

Asp Val Leu Gly Ala Leu Asp Ala Pro Val Ser Thr Ala Ala Trp Pro
                325                 330                 335

Ser Leu Gln Gln Lys Asp Lys Pro Ala Asn Gly Gly Val Gln Glu Glu
            340                 345                 350

Lys Glu Thr Asp Ser Asp Lys Pro Ala Glu Pro Thr Gly Ile Lys Ala
        355                 360                 365
```

Asp Gly Lys Leu Phe Lys Ala Met Ile Glu Ser Ala Val Asp Asp Leu
370             375                 380

Lys Lys Glu Glu Pro Gln Ile Thr Lys Tyr Asp Thr Ile Ala Gly Asp
385             390                 395                 400

Gly Asp Cys Gly Glu Thr Leu Leu Ala Gly Asp Gly Ile Leu Asp
        405                 410                 415

Ala Ile Lys Asn Lys Lys Ile Asp Leu Asp Asp Ala Ala Gly Val Ala
        420                 425                 430

Asp Ile Ser His Ile Val Glu Asn Ser Met Gly Thr Ser Gly Gly
        435                 440                 445

Leu Tyr Ser Ile Phe Phe Ser Gly Leu Val Val Gly Ile Lys Glu Thr
450                 455                 460

Lys Ala Lys Glu Leu Ser Val Asp Val Phe Ala Lys Ala Cys Glu Thr
465                 470                 475                 480

Ala Leu Glu Thr Leu Ser Lys Tyr Thr Gln Ala Arg Val Gly Asp Arg
            485                 490                 495

Thr Leu Met Asp Ala Leu Val Pro Phe Val Glu Thr Leu Ser Lys Thr
            500                 505                 510

Lys Asp Phe Ala Lys Ala Val Glu Ala Ala Arg Lys Gly Ala Asp Glu
            515                 520                 525

Thr Ser Lys Leu Pro Ala Asn Phe Gly Arg Ala Ser Tyr Val Asn Glu
530                 535                 540

Glu Gly Leu Glu Asn Ile Pro Asp Pro Gly Ala Leu Gly Leu Ala Val
545                 550                 555                 560

Ile Phe Glu Gly Leu Leu Lys Ala Trp Glu Lys Lys
            565                 570

<210> SEQ ID NO 14
<211> LENGTH: 580
<212> TYPE: PRT
<213> ORGANISM: Schizosaccharomyces pombe

<400> SEQUENCE: 14

Met Asp Lys His Phe Ile Asn Asp Pro Glu Val Leu Val Leu Asp Gly
1               5                   10                  15

Leu Lys Ser Leu Ala Asp Met Asn Lys Thr Leu Thr Val His Glu Glu
            20                  25                  30

Gly Lys Phe Ile Tyr Phe His Asp Tyr Asn Lys Asn Val Ser Val
        35                  40                  45

Ile Ser Gly Gly Gly Ala Gly His Glu Pro Thr His Ser Ser Phe Val
50                  55                  60

Gly Lys Gly Met Leu Thr Ala Ala Val Ser Gly Ser Ile Phe Ala Ser
65                  70                  75                  80

Pro Ser Ser Lys Gln Ile Tyr Thr Gly Ile Lys Gln Val Glu Ser Glu
                85                  90                  95

Ala Gly Thr Leu Val Ile Cys Lys Asn Tyr Thr Gly Asp Ile Leu His
            100                 105                 110

Phe Gly Met Ala Leu Glu Lys Gln Arg Thr Ala Gly Lys Lys Ala Glu
        115                 120                 125

Leu Ile Ala Val Ala Asp Asp Val Ser Val Gly Arg Lys Lys Ser Gly
            130                 135                 140

Lys Val Gly Arg Arg Gly Leu Ser Gly Thr Val Leu Val His Lys Ile
145                 150                 155                 160

Ala Gly Ala Ala Ala Ala Arg Gly Leu Pro Leu Glu Ala Val Thr Thr
                165                 170                 175

-continued

Ile Ala Lys Ala Ala Ile Asp Asn Leu Val Ser Ile Gly Ala Ser Leu
            180                 185                 190

Ala His Val His Val Pro Gly His Glu Pro Ile Ala Lys Glu Asp Glu
            195                 200                 205

Met Lys His Asp Glu Met Glu Leu Gly Met Gly Ile His Asn Glu Pro
    210                 215                 220

Gly Cys Lys Arg Ile Ser Pro Ile Pro Ser Ile Asp Asp Leu Ile Ala
225                 230                 235                 240

Gln Met Leu Lys Gln Met Leu Asp Gln Ser Asp Lys Asp Arg Ala Tyr
                245                 250                 255

Val Lys Ile Glu Gly Asp Asp Glu Val Val Leu Leu Met Asn Asn Leu
            260                 265                 270

Gly Gly Leu Ser Met Leu Glu Phe Ser Ala Ile Ser His Lys Val Lys
        275                 280                 285

Glu Ala Leu Ala Lys Glu Tyr Lys Ile Asn Pro Val Arg Ile Phe Ala
    290                 295                 300

Gly Pro Phe Thr Thr Ser Leu Asn Gly Leu Gly Phe Gly Ile Thr Leu
305                 310                 315                 320

Leu Arg Thr Thr Asp Arg Val Lys Val Glu Gly Glu Tyr Ser Leu
                325                 330                 335

Val Asp Leu Ile Asp Gln Pro Val Glu Ala Ile Gly Trp Pro Leu Cys
            340                 345                 350

Gln Pro Ser Asp Leu Lys Ser Lys Asn Lys Ile Gly Asn Val Ser Ile
        355                 360                 365

Glu Glu Gly Gln Lys Asp Val Lys Ser Pro Val Thr Val Asp Lys Glu
    370                 375                 380

Lys Val Arg Gln Ala Ile Val Asn Ser Met Glu Asn Leu Ile Lys Ala
385                 390                 395                 400

Glu Pro Lys Ile Thr Lys Phe Asp Thr Met Ala Gly Asp Gly Asp Cys
                405                 410                 415

Gly Thr Thr Leu Lys Arg Gly Ala Glu Gly Val Leu Lys Phe Val Lys
            420                 425                 430

Ser Asp Lys Phe Ser Asp Pro Ile Arg Ile Val Arg Asp Ile Ala
        435                 440                 445

Asp Val Ile Glu Asp Asn Met Asp Gly Thr Ser Gly Ala Leu Tyr Ala
    450                 455                 460

Ile Phe Phe His Gly Phe Ala Lys Gly Met Lys Asp Thr Leu Glu Lys
465                 470                 475                 480

Ser Lys Asp Ile Ser Ser Lys Thr Trp Ala Ala Gly Leu Lys Val Ala
                485                 490                 495

Leu Asp Thr Leu Phe Lys Tyr Thr Pro Ala Arg Pro Gly Asp Ser Thr
            500                 505                 510

Met Cys Asp Ala Leu Val Pro Phe Val Glu Thr Phe Val Lys Thr Asn
        515                 520                 525

Asp Leu Asn Ala Ala Val Glu Glu Ala Arg Lys Gly Ala Asp Ala Thr
    530                 535                 540

Ala Asp Met Gln Ala Lys Leu Gly Arg Ala Val Tyr Val Gly Asp Asp
545                 550                 555                 560

Val Lys Val Pro Asp Ala Gly Ala Leu Gly Val Val Ala Ile Val Glu
                565                 570                 575

Gly Phe Thr Lys
            580

<210> SEQ ID NO 15
<211> LENGTH: 621
<212> TYPE: DNA
<213> ORGANISM: Artificial Sequence
<220> FEATURE:
<223> OTHER INFORMATION: Fragment containing the TDH3-promoter

<400> SEQUENCE: 15

```
ggtctcggtg cttagtcaaa aaattagcct tttaattctg ctgtaacccg tacatgccca    60
aaatagggg cgggttacac agaatatata acatcgtagg tgtctgggtg aacagtttat   120
tcctggcatc cactaaatat aatggagccc gcttttaag ctggcatcca gaaaaaaaa    180
gaatcccagc accaaaatat tgttttcttc accaaccatc agttcatagg tccattctct   240
tagcgcaact acagagaaca ggggcacaaa caggcaaaaa acgggcacaa cctcaatgga   300
gtgatgcaac ctgcctggag taaatgatga cacaaggcaa ttgacccacg catgtatcta   360
tctcatttc ttacaccttc tattaccttc tgctctctct gatttggaaa aagctgaaaa   420
aaaaggttga aaccagttcc ctgaaattat tcccctactt gactaataag tatataaaga   480
cggtaggtat tgattgtaat tctgtaaatc tatttcttaa acttcttaaa ttctactttt   540
atagttagtc ttttttttag ttttaaaaca ccaagaactt agtttcgaat aaacacacat   600
aaacaaacaa aatgggagac c                                             621
```

<210> SEQ ID NO 16
<211> LENGTH: 620
<212> TYPE: DNA
<213> ORGANISM: Artificial Sequence
<220> FEATURE:
<223> OTHER INFORMATION: Fragment containing the TDH1-promoter

<400> SEQUENCE: 16

```
ggtctcggtg ccagcgccag tagggttgtt gagcttagta aaaatgtgcg caccacaagc    60
ctacagactc cacgtcacat gaaaccacac cgtggggcct tgttgcgcta ggaataggat   120
atgcgacgaa gacgcttctg cttagtaacc acaccacatt tcagggggt cgatctgctt   180
gcttccttta ctgtcacgag cggcccataa tcgcgctttt ttttaaaag gcgcgagaca   240
gcaaacagga agctcgggtt tcaaccttcg gagtggtcgc agatctggag actggatctt   300
tacaatacag taaggcaagc caccatctgc ttcttaggtg catgcgacgg tatccacgtg   360
cagaacaaca tagtctgaag aaggggggga ggagcatgtt cattctctgt agcagtaaga   420
gcttggtgat aatgaccaaa actggagtct cgaaatcata taaatagaca atatattttc   480
acacaatgag atttgtagta cagttctatt ctctctcttg cataaataag aaattcatca   540
agaacttggt ttgatatttc accaacacac acaaaaaaca gtacttcact aaatttacac   600
acaaaacaaa atgggagacc                                               620
```

<210> SEQ ID NO 17
<211> LENGTH: 321
<212> TYPE: DNA
<213> ORGANISM: Artificial Sequence
<220> FEATURE:
<223> OTHER INFORMATION: Fragment containing the PGK1-terminator

<400> SEQUENCE: 17

```
ggtctcgtaa attgaattga attgaaatcg atagatcaat ttttttcttt tctctttccc    60
catcctttac gctaaaataa tagtttattt tattttttga atattttta tttatatacg   120
tatatataga ctattattta tcttttaatg attattaaga ttttattaa aaaaaattac   180
```

```
gctcctcttt taatgccttt atgcagtttt ttttcccatt cgatatttct atgttcgggt    240
tcagcgtatt ttaagtttaa taactcgaaa attctgcgtt cgttaaagct ttcgagaagg    300
atattatttc cctcggagac c                                              321
```

<210> SEQ ID NO 18
<211> LENGTH: 621
<212> TYPE: DNA
<213> ORGANISM: Artificial Sequence
<220> FEATURE:
<223> OTHER INFORMATION: Fragment containing the PGK1-promoter

<400> SEQUENCE: 18

```
ggtctcggtg cgggccagaa aaaggaagtg tttccctcct tcttgaattg atgttaccct     60
cataaagcac gtggcctctt atcgagaaag aaattaccgt cgctcgtgat ttgtttgcaa    120
aaagaacaaa actgaaaaaa cccagacacg ctcgacttcc tgtcttccta ttgattgcag    180
cttccaattt cgtcacacaa caaggtccta gcgacggctc acaggttttg taacaagcaa    240
tcgaaggttc tggaatggcg ggaaagggtt tagtaccaca tgctatgatg cccactgtga    300
tctccagagc aaagttcgtt cgatcgtact gttactctct ctctttcaaa cagaattgtc    360
cgaatcgtgt gacaacaaca gcctgttctc acacactctt ttcttctaac caaggggtg    420 gtttagttta gtagaacctc gtgaaactta catttacata tatataaact tgcataaatt    480
ggtcaatgca agaaatacat atttggtctt ttctaattcg tagtttttca agttcttaga    540
tgctttcttt ttctcttttt tacagatcat caaggaagta attatctact ttttacaaca    600
aatataaaac aatgggagac c                                              621
```

<210> SEQ ID NO 19
<211> LENGTH: 621
<212> TYPE: DNA
<213> ORGANISM: Artificial Sequence
<220> FEATURE:
<223> OTHER INFORMATION: Fragment containing the PRE3-promoter

<400> SEQUENCE: 19

```
ggtctcggtg ccaaacatta atttgttctg catactttga acctttcaga aaataaaaaa     60
cattacgcgc atacttaccc tgctcgcgaa gaagagtaac actaacgcat tctatgggca    120
attgaagaca gtattcagta caagacatag tccgtttcct tgagtcaatt cctatagcat    180
tatgaactag ccgcctttaa gagtgccaag ctgttcaaca ccgatcattt ttgatgattt    240
ggcgtttttg ttatattgat agatttcttt tgaattttgt catttccact tttccactcg    300
caacggaatc cggtggcaaa aagggaaaa gcattgaaat gcaatcttta acagtatttt    360
aaacaagttg cgacacggtg tacaattacg ataagaattg ctacttcaaa gtacacacag    420
aaagttaaca tgaatggaat tcaagtggac atcaatcgtt tgaaaaaggg cgaagtcagt    480
ttaggtacct caatgtatgt atataagaat ttttcctccc actttattgt ttctaaaagt    540
tcaatgaagt aaagtctcaa ttggccttat tactaactaa taggtatctt ataatcacct    600
aataaaatag aatgggagac c                                              621
```

<210> SEQ ID NO 20
<211> LENGTH: 322
<212> TYPE: DNA
<213> ORGANISM: Artificial Sequence
<220> FEATURE:
<223> OTHER INFORMATION: Fragment containing the PGI1-terminator

<400> SEQUENCE: 20

```
ggtctcgtaa aacaaatcgc tcttaaatat atacctaaag aacattaaag ctatattata    60
agcaaagata cgtaaatttt gcttatatta ttatacacat atcatatttc tatattttta   120
agatttggtt atataatgta cgtaatgcaa aggaaataaa ttttatacat tattgaacag   180
cgtccaagta actacattat gtgcactaat agtttagcgt cgtgaagact ttattgtgtc   240
gcgaaaagta aaaattttaa aaattagagc accttgaact tgcgaaaaag gttctcatca   300
actgtttaaa acctcggaga cc                                            322
```

<210> SEQ ID NO 21
<211> LENGTH: 621
<212> TYPE: DNA
<213> ORGANISM: Artificial Sequence
<220> FEATURE:
<223> OTHER INFORMATION: Fragment containing the ENO1-promoter

<400> SEQUENCE: 21

```
ggtctcggtg cccgcggaac cgccagatat tcattacttg acgcaaaagc gtttgaaata    60
atgacgaaaa agaaggaaga aaaaaaaaga aaaataccgc ttctaggcgg gttatctact   120
gatccgagct tccactagga tagcacccaa acacctgcat atttggacga cctttactta   180
caccaccaaa aaccactttc gcctctcccg ccctgataa cgtccactaa ttgagcgatt   240
acctgagcgg tcctcttttg tttgcagcat gagacttgca tactgcaaat cgtaagtagc   300
aacgtgtcaa ggtcaaaact gtatggaaac cttgtcacct cacttaattc tagctagcct   360
accctgcaag tcaagaggtg tccgtgattc ctagccacct caaggtatgc ctctccccgg   420
aaactgtggc ctttctggc acacatgatc tccacgattt caacatataa atagcttttg   480
ataatggcaa tattaatcaa atttatttta cttctttctt gtaacatctc tcttgtaatc   540
ccttattcct tctagctatt tttcataaaa aaccaagcaa ctgcttatca acacacaaac   600
actaaatcaa aatgggagac c                                            621
```

<210> SEQ ID NO 22
<211> LENGTH: 621
<212> TYPE: DNA
<213> ORGANISM: Artificial Sequence
<220> FEATURE:
<223> OTHER INFORMATION: Fragment containing the ACT1-promoter

<400> SEQUENCE: 22

```
ggtctcggtg caacatatat acacaattac agtaacaata acaagaggac agatactacc    60
aaaatgtgtg gggaagcggg taagctgcca cagcaattaa tgcacaacat ttaacctaca   120
ttcttcctta tcggatcctc aaaacccttaa aaacatatg cctcacccta acatattttc   180
caattaaccc tcaatatttc tctgtcaccc ggcctctatt ttccattttc ttctttaccc   240
gccacgcgtt ttttctttc aaattttttt cttcttcttt cttttcttc cacgtcctct   300
tgcataaata aataaaccgt tttgaaacca aactcgcctc tctctctcct ttttgaaata   360
tttttgggtt tgtttgatcc tttccttccc aatctctctt gtttaatata tattcattta   420
tatcacgctc tctttttatc ttcctttttt tcctctctct tgtattcttc cttcccttt   480
ctactcaaac caagaagaaa aagaaaaggt caatctttgt taaagaatag gatcttctac   540
tacatcagct tttagatttt tcacgcttac tgcttttttc ttcccaagat cgaaaattta   600
ctgaattaac aatgggagac c                                            621
```

<210> SEQ ID NO 23
<211> LENGTH: 322
<212> TYPE: DNA
<213> ORGANISM: Artificial Sequence
<220> FEATURE:
<223> OTHER INFORMATION: Fragment containing the CYC1-terminator

<400> SEQUENCE: 23

```
ggtctcgtaa aacaggcccc ttttcctttg tcgatatcat gtaattagtt atgtcacgct      60
tacattcacg ccctccccccc acatccgctc taaccgaaaa ggaaggagtt agacaacctg    120
aagtctaggt ccctatttat tttttatag ttatgttagt attaagaacg ttatttatat     180
ttcaaatttt tcttttttt ctgtacaaac gcgtgtacgc atgtaacatt atactgaaaa    240
ccttgcttga aaggttttg ggacgctcga aggctttaat ttgcaagctt cgcagtttac    300
actctcatcg tcctcggaga cc                                                322
```

<210> SEQ ID NO 24
<211> LENGTH: 621
<212> TYPE: DNA
<213> ORGANISM: Artificial Sequence
<220> FEATURE:
<223> OTHER INFORMATION: Fragment containing the TPI1-promoter

<400> SEQUENCE: 24

```
ggtctcggtg cgacacctaa ctacatagtg tttaaagatt acggatattt aacttactta      60
gaataatgcc attttttga gttataataa tcctacgtta gtgtgagcgg gatttaaact    120
gtgaggacct taatacattc agacacttct gcggtatcac cctacttatt cccttcgaga    180
ttatatctag gaacccatca ggttggtgga agattacccg ttctaagact tttcagcttc    240
ctctattgat gttacacctg gacaccccctt ttctggcatc cagtttttaa tcttcagtgg    300
catgtgagat tctccgaaat taattaaagc aatcacacaa ttctctcgga taccacctcg    360
gttgaaactg acaggtggtt tgttacgcat gctaatgcaa aggagcctat ataccctttgg    420 ctcggctgct gtaacaggga atataaaggg cagcataatt taggagttta gtgaacttgc    480
aacatttact atttttccctt cttacgtaaa tattttctt tttaattcta aatcaatctt    540
tttcaatttt ttgtttgtat tctttttcttg cttaaatcta taactacaaa aaacacatac    600
ataaactaaa aatgggagac c                                                621
```

<210> SEQ ID NO 25
<211> LENGTH: 348
<212> TYPE: DNA
<213> ORGANISM: Artificial Sequence
<220> FEATURE:
<223> OTHER INFORMATION: Fragment containing the ATG7-promoter

<400> SEQUENCE: 25

```
ggtctcggtg caaaaacacc aaagaatgga gagtagtata tactcttaac aaacactagc      60
atttcagttt atctatatac atatatatgg atgtaaaatg tacttatgg aagaacaagc    120 caccacatgt tgaaaactag ataggcaagc aagattttc atttgtagag ctcttacgca    180
agatttttaa acttccgctt ttttaatcca tgagattcct ttggacaccc tttccggcac    240
ggcaaaacaa aaaaattaag ggaactcatt attttacgat gctacttaga taactaaagt    300
tcattatatt tcaacaaata taagataatc aagaataaat gggagacc                  348
```

<210> SEQ ID NO 26
<211> LENGTH: 322
<212> TYPE: DNA

<213> ORGANISM: Artificial Sequence
<220> FEATURE:
<223> OTHER INFORMATION: Fragment containing the ENO1-terminator

<400> SEQUENCE: 26

```
ggtctcgtaa aagcttttga ttaagccttc tagtccaaaa aacacgtttt tttgtcattt    60
atttcatttt cttagaatag tttagtttat tcattttata gtcacgaatg ttttatgatt   120
ctatataggg ttgcaaacaa gcattttttca ttttatgtta aaacaatttc aggtttacct   180
tttattctgc ttgtggtgac gcgtgtatcc gcccgctctt ttggtcaccc atgtatttaa   240
ttgcataaat aattcttaaa agtggagcta gtctatttct atttacatac ctctcatttc   300
tcatttcctc ccctcggaga cc                                            322
```

<210> SEQ ID NO 27
<211> LENGTH: 1674
<212> TYPE: DNA
<213> ORGANISM: Artificial Sequence
<220> FEATURE:
<223> OTHER INFORMATION: Sequence of the kanMX marker and flanking
      regions

<400> SEQUENCE: 27

```
ttgcccatcg aacgtacaag tactcctctg ttctctcctt cctttgcttt cttcgtacgc    60
tgcaggtcga cgaattctac cgttcgtata atgtatgcta tacgaagtta tagatctgtt   120
tagcttgcct cgtccccgcc gggtcacccg ccagcgaca tggagcccca gaatacccctc   180
cttgacagtc ttgacgtgcg cagctcaggg gcatgatgtg actgtcgccc gtacatttag   240
cccatacatc cccatgtata atcatttgca tccatacatt ttgatggccg cacggcgcga   300
agcaaaaatt acggcctctc gctgcagacc tgcgagcagg gaaacgctcc cctcacagac   360
gcgttgaatt gtccccacgc cgcgcccctg tagagaaata taaaaggtta ggatttgcca   420
ctgaggttct tctttcatat acttcctttt aaaatcttgc taggatacag ttctcacatc   480
acatccgaac ataaacaacc atgggtaagg aaaagactca cgtttcgagg ccgcgattaa   540
attccaacat ggatgctgat ttatatgggt ataaatgggc tcgcgataat gtcgggcaat   600
caggtgcgac aatctatcga ttgtatggga agcccgatgc gccagagttg tttctgaaac   660
atggcaaagg tagcgttgcc aatgatgtta cagatgagat ggtcagacta aactggctga   720
cggaatttat gcctcttccg accatcaagc attttatccg tactcctgat gatgcatggt   780
tactcaccac tgcgatcccc ggcaaaacag cattccaggt attagaagaa tatcctgatt   840
caggtgaaaa tattgttgat gcgctggcag tgttcctgcg ccggttgcat tcgattcctg   900
tttgtaattg tccttttaac agcgatcgcg tatttcgtct cgctcaggcg caatcacgaa   960
tgaataacgg tttggttgat gcgagtgatt ttgatgacga gcgtaatggc tggcctgttg  1020
aacaagtctg gaaagaaatg cataagcttt tgccattctc accggattca gtcgtcactc  1080
atggtgattt ctcacttgat aaccttattt tgacgagggg aaattaata ggttgtattg  1140
atgttggacg agtcggaatc gcagaccgat accaggatct tgccatccta tggaactgcc  1200
tcggtgagtt ttctccttca ttacagaaac ggcttttttca aaaatatggt attgataatc  1260
ctgatatgaa taaattgcag tttcatttga tgctcgatga gttttctaa tcagtactga  1320
caataaaaag attcttgttt tcaagaactt gtcatttgta tagtttttt atattgtagt  1380
tgttctattt taatcaaatg ttagcgtgat ttatatttt tttcgcctcg acatcatctg  1440
cccagatgcg aagttaagtg cgcagaaagt aatatcatgc gtcaatcgta tgtgaatgct  1500
```

```
ggtcgctata ctgctgtcga ttcgatacta acgccgccat ccagtgtcga aaacgagctc   1560
ataacttcgt ataatgtatg ctatacgaac ggtagaattc gatatcagat ccactagtgg   1620
cctacggatc gatgtacaca accgactgca cccaaacgaa cacaaatctt agca         1674
```

<210> SEQ ID NO 28
<211> LENGTH: 2569
<212> TYPE: DNA
<213> ORGANISM: Artificial Sequence
<220> FEATURE:
<223> OTHER INFORMATION: Sequence of gene disruption cassette
      GPD1::hphMX

<400> SEQUENCE: 28

```
aagcttggta cccgccttgc ttctctcccc ttccttttct ttttccagtt ttccctattt     60 tgtcccttt tccgcacaac aagtatcaga atgggttcat caaatctatc caacctaatt    120
cgcacgtaga ctggcttggt attggcagtt tcgtagttat atatatacta ccatgagtga   180
aactgttacg ttaccttaaa ttctttctcc ctttaatttt cttttatctt actctcctac   240
ataagacatc aagaaacaat tgtatattgt acaccccccc cctccacaaa cacaaatatt   300
gataatataa agatgtctgc tgctgctgat agattaaact taacttccgg ccacttgaat   360
gctggtctag taacggccgc cagtgtgctg gaattcgccc ttaatccgga gctcgtacgt   420
tcgaacttaa ggcctcgtcc ccgccgggtc accoggccag cgacatggag cccagaata    480 ccctccttga cagtcttgac gtgcgcagct caggggcatg atgtgactgt cgcccgtaca   540
tttagcccat acatccccat gtataatcat ttgcatccat acattttgat ggccgcacgg   600
cgcgaagcaa aaattacggc tcctcgctgc agacctgcga gcagggaaac gctcccctca   660
cagacgcgtg aattgtcccc acgccgcgcc cctgtagaga aatataaaag gttaggattt   720
gccactgagg ttcttctttc atatacttcc ttttaaaatc ttgctaggat acagttctca   780
catcacatcc gaacataaac aaccatgggt aaaaagcctg aactcaccgc gacgtctgtc   840
gagaagtttc tgatcgaaaa gttcgacagc gtctccgacc tgatgcagct ctcggagggc   900
gaagaatctc gtgctttcag cttcgatgta ggagggcgtg gatatgtcct gcgggtaaat   960
agctgcgccg atggtttcta caaagatcgt tatgtttatc ggcactttgc atcggccgcg  1020
ctcccgattc cggaagtgct tgacattggg gaattcagcg agagcctgac ctattgcatc  1080
tcccgccgtg cacagggtgt cacgttgcaa gacctgcctg aaaccgaact gcccgctgtt  1140
ctgcagccgg tcgcggaggc catggatgcg atcgctgcgg ccgatcttag ccagacgagc  1200
gggttcggcc cattcggacc gcaaggaatc ggtcaataca ctacatggcg tgatttcata  1260
tgcgcgattg ctgatcccca tgtgtatcac tggcaaactg tgatggacga caccgtcagt  1320
gcgtccgtcg cgcaggctct cgatgagctg atgctttggg ccgaggactg ccccgaagtc  1380
cggcacctcg tgcacgcgga tttcggctcc aacaatgtcc tgacggacaa tggccgcata  1440
acagcggtca ttgactggag cgaggcgatg ttcggggatt cccaatacga ggtcgccaac  1500
atcttcttct ggaggccgtg gttggcttgt atggagcagc agacgcgcta cttcgagcgg  1560
aggcatccgg agcttgcagg atcgccgcgg ctccgggcgt atatgctccg cattggtctt  1620
gaccaactct atcagagctt ggttgacggc aatttcgatg atgcagcttg gcgcagggt   1680 cgatgcgacg caatcgtccg atccggagcc gggactgtcg gcgtacacaa atcgcccgc   1740 agaagcgcgg ccgtctggac cgatggctgt gtagaagtac tcgccgatag tggaaaccga  1800
cgccccagca ctcgtccgag ggcaaaggaa taatcagtac tgacaataaa aagattcttg  1860
```

```
ttttcaagaa cttgtcattt gtatagtttt tttatattgt agttgttcta ttttaatcaa      1920
atgttagcgt gatttatatt ttttttcgcc tcgacatcat ctgcccagat gcgaagttaa      1980
gtgcgcagaa agtaatatca tgcgtcaatc gtatgtgaat gctggtcgct atactgctgt      2040
cgattcgata ctaacgccgc catccagtgt cgacggatcc taggtgtacg agttgttgaa      2100
tggccaatcc gctcaaggtt taattacctg caaagaagtt cacgaatggt tggaaacatg      2160
tggctctgtc gaagacttcc cattatttga agccgtatac caaatcgttt acaacaacta      2220
cccaatgaag aacctgccgg acatgattga agaattagat ctacatgaag attagattta      2280
ttggagaaag ataacatatc atactttccc ccactttttt cgaggctctt ctatatcata      2340
ttcataaatt agcattatgt catttctcat aactacttta tcacgttaga aattacttat      2400
tattattaaa ttaatacaaa atttagtaac caaataaata taaataaata tgtatattta      2460
aattttaaaa aaaaaatcct atagagcaaa aggattttcc attataatat tagctgtaca      2520
cctcttccgc attttttgag ggtggttaca acaccactcg gtaccatgg                  2569
```

<210> SEQ ID NO 29
<211> LENGTH: 2069
<212> TYPE: DNA
<213> ORGANISM: Artificial Sequence
<220> FEATURE:
<223> OTHER INFORMATION: Sequence of gene disruption cassette GPD2::
      natMX;

<400> SEQUENCE: 29

```
ggtaccagat cttttgcggc gaggtgccga tgggttgctg aggggaagag tgtttagctt        60
acggacctat tgccattgtt attccgatta atctattgtt cagcagctct tctctaccct       120
gtcattctag tatttttttt ttttttttt ggttttactt ttttttcttc ttgccttttt        180
ttcttgttac ttttttttcta gttttttttc cttccactaa gcttttttcct tgatttatcc    240 ttgggttctt ctttctactc ctttagattt tttttttata tattaatttt taagtttatg      300
tattttggta gattcaattc tctttccctt tccttttcct tcgctcccct tccttatcaa      360
tgcttgctgt cagaagatta acaagataca cattccttaa ggcctcgtcc ccgccgggtc      420
acccggccag cgacatggag gcccagaata ccctccttga cagtcttgac gtgcgcagct      480
caggggcatg atgtgactgt cgcccgtaca tttagcccat acatccccat gtataatcat      540
ttgcatccat acattttgat ggccgcacgg cgcgaagcaa aaattacggc tcctcgctgc      600
agacctgcga gcagggaaac gctcccctca cagacgcgtt gaattgtccc cacgccgcgc      660
ccctgtgaga aaatataaaa ggttaggatt tgccactgag gttcttcttt catatacttc      720
cttttaaaat cttgctagga tacagttctc acatcacatc cgaacataaa caaccatgta      780
aaatgaccac tcttgacgac acggcttacc ggtaccgcac cagtgtcccg ggggacgccg      840
aggccatcga ggcactggat gggtccttca ccaccgacac cgtcttccgc gtcaccgcca      900
ccggggacgg cttcacccctg cgggaggtgc cgtggacccc gcccctgacc aaggtgttcc      960
ccgacgacga atcggacgac gaatcggacg ccggggagga cggcgacccg gactcccgga      1020
cgttcgtcgc gtacgggggac gacggcgacc tggcgggctt cgtggtcgtc tcgtactccg      1080
gctggaaccg ccggctgacc gtcgaggaca tcgaggtcgc cccggagcac cgggggcacg      1140
gggtcgggcg cgcgttgatg gggctcgcga cggagttcgc ccgcgagcgg ggcgccgggc      1200
acctctggct ggaggtcacc aacgtcaacg caccggcgat ccacgcgtac cggcggatgg      1260 ggttcacccct ctgcggcctg gacaccgccc tgtacgacgg caccgcctcg gacggcgagc      1320
```

```
aggcgctcta catgagcatg ccctgcccct agtactgaca ataaaaagat tcttgttttc    1380
aagaacttgt catttgtata gttttttat attgtagttg ttctatttta atcaaatgtt     1440
agcgtgattt atatttttt tcgcctcgac atcatctgcc cagatgcgaa gttaagtgcg     1500
cagaaagtaa tatcatgcgt caatcgtatg tgaatgctgg tcgctatact gctgtcgatt    1560
cgatactaac gccgccatcc agtgtcgacg gatcctaggt gtacagggcc caaaagggcg    1620
aattctgcag atatccatca cactggcggc cgctcgagat agtctacaac aacgtccgca    1680
tggaagacct accggagatg attgaagagc tagacatcga tgacgaatag acactctccc    1740 ccccctccc cctctgatct ttcctgttgc ctcttttcc cccaaccaat ttatcattat      1800
acacaagttc tacaactact actagtaaca ttactacagt tattataatt ttctattctc    1860
tttttcttta agaatctatc attaacgtta atttctatat atacataact accattatac   1920
acgctattat cgtttacata tcacatcacc gttaatgaaa gatacgacac cctgtacact   1980
aacacaatta aataatcgcc ataaccttt ctgttatcta tagcccttaa agctgtttct    2040
tcgagctttt tcactgcaga tctccatgg                                      2069
```

<210> SEQ ID NO 30
<211> LENGTH: 19
<212> TYPE: DNA
<213> ORGANISM: Artificial Sequence
<220> FEATURE:
<223> OTHER INFORMATION: Forward primer 5 INT1 fragment (INT5-f)

<400> SEQUENCE: 30

```
cggcattatt gtgtatggc                                                    19
```

<210> SEQ ID NO 31
<211> LENGTH: 73
<212> TYPE: DNA
<213> ORGANISM: Artificial Sequence
<220> FEATURE:
<223> OTHER INFORMATION: Reverse primer 5 INT1 fragment (INT5-r)

<400> SEQUENCE: 31

```
aaacgcctgt gggtgtggta ctggatatgc aaagcgattg gaagtcgctt agggtttcaa     60
agatccatac ttc                                                         73
```

<210> SEQ ID NO 32
<211> LENGTH: 22
<212> TYPE: DNA
<213> ORGANISM: Artificial Sequence
<220> FEATURE:
<223> OTHER INFORMATION: Forward primer expression cassette 1 (con5-f)

<400> SEQUENCE: 32

```
aagcgacttc caatcgcttt gc                                               22
```

<210> SEQ ID NO 33
<211> LENGTH: 21
<212> TYPE: DNA
<213> ORGANISM: Artificial Sequence
<220> FEATURE:
<223> OTHER INFORMATION: Reverse primer expression cassette 1 (conA-r)

<400> SEQUENCE: 33

```
aaagcaaagg aaggagagaa c                                                21
```

<210> SEQ ID NO 34
<211> LENGTH: 20

-continued

```
<212> TYPE: DNA
<213> ORGANISM: Artificial Sequence
<220> FEATURE:
<223> OTHER INFORMATION: Forward primer marker (conA-f)

<400> SEQUENCE: 34
ttgcccatcg aacgtacaag                                                20

<210> SEQ ID NO 35
<211> LENGTH: 23
<212> TYPE: DNA
<213> ORGANISM: Artificial Sequence
<220> FEATURE:
<223> OTHER INFORMATION: Reverse primer marker (conB-r)

<400> SEQUENCE: 35
tgctaagatt tgtgttcgtt tgg                                            23

<210> SEQ ID NO 36
<211> LENGTH: 20
<212> TYPE: DNA
<213> ORGANISM: Artificial Sequence
<220> FEATURE:
<223> OTHER INFORMATION: Forward primer expression cassette 2 (conB-f)

<400> SEQUENCE: 36
cggatcgatg tacacaaccg                                                20

<210> SEQ ID NO 37
<211> LENGTH: 23
<212> TYPE: DNA
<213> ORGANISM: Artificial Sequence
<220> FEATURE:
<223> OTHER INFORMATION: Reverse primer expression cassette 2 (conC-r)

<400> SEQUENCE: 37
caacaggagg cggatggata tac                                            23

<210> SEQ ID NO 38
<211> LENGTH: 21
<212> TYPE: DNA
<213> ORGANISM: Artificial Sequence
<220> FEATURE:
<223> OTHER INFORMATION: Forward primer expression cassette 3 (conC-f)

<400> SEQUENCE: 38
acgctttccg gcatcttcca g                                              21

<210> SEQ ID NO 39
<211> LENGTH: 20
<212> TYPE: DNA
<213> ORGANISM: Artificial Sequence
<220> FEATURE:
<223> OTHER INFORMATION: Reverse primer expression cassette 3 (conD-r)

<400> SEQUENCE: 39
gcggaatatt ggcggaacgg                                                20

<210> SEQ ID NO 40
<211> LENGTH: 22
<212> TYPE: DNA
<213> ORGANISM: Artificial Sequence
<220> FEATURE:
<223> OTHER INFORMATION: Forward primer expression cassette 4 (conD-f)

<400> SEQUENCE: 40
```
aacgttgtcc aggtttgtat cc                                              22

<210> SEQ ID NO 41
<211> LENGTH: 24
<212> TYPE: DNA
<213> ORGANISM: Artificial Sequence
<220> FEATURE:
<223> OTHER INFORMATION: Reverse primer expression cassette 4 (con3-r)

<400> SEQUENCE: 41
acttagtatg gtctgttgga aagg                                            24

<210> SEQ ID NO 42
<211> LENGTH: 90
<212> TYPE: DNA
<213> ORGANISM: Artificial Sequence
<220> FEATURE:
<223> OTHER INFORMATION: Forward primer 3 INT1 fragment (INT3-f)

<400> SEQUENCE: 42
agaaagcctg tatgcgaagc cacaatcctt tccaacagac catactaagt attttatttt     60
acttttttta gaatgacctg ttcccgacac                                      90

<210> SEQ ID NO 43
<211> LENGTH: 24
<212> TYPE: DNA
<213> ORGANISM: Artificial Sequence
<220> FEATURE:
<223> OTHER INFORMATION: Reverse primer 3 INT1 fragment (INT3-r)

<400> SEQUENCE: 43
cacaagctta ttcttccaaa aatc                                            24

<210> SEQ ID NO 44
<211> LENGTH: 3506
<212> TYPE: DNA
<213> ORGANISM: Artificial Sequence
<220> FEATURE:
<223> OTHER INFORMATION: Sequence of plasmid p5Abbn

<400> SEQUENCE: 44
tagaaaaact catcgagcat caaatgaaac tgcaatttat tcatatcagg attatcaata     60
ccatattttt gaaaaagccg tttctgtaat gaaggagaaa actcaccgag gcagttccat    120
aggatggcaa gatcctggta tcggtctgcg attccgactc gtccaacatc aatacaacct    180
attaatttcc cctcgtcaaa aataaggtta tcaagtgaga atcaccatg agtgacgact    240 gaatccggtg agaatggcaa agtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900

```
ataggggtca gtgttacaac caattaacca attctgaaca ttatcgcgag cccatttata    960
cctgaatatg gctcataaca ccccttgttt gcctggcggc agtagcgcgg tggtcccacc   1020
tgacccatg ccgaactcag aagtgaaacg ccgtagcgcc gatggtagtg tggggactcc    1080
ccatgcgaga gtagggaact gccaggcatc aaataaaacg aaaggctcag tcgaaagact   1140
gggcctttcg cccgggctaa ttaggggtg tcgcccttat tcgactctat agtgaagttc    1200
ctattctcta gaaagtatag gaacttctga agtggggaag cgacttccaa tcgctttgca   1260
tatccagtac cacacccaca ggcgtttgtg cggagaccgg cttactaaaa gccagataac   1320
agtatgcata tttgcgcgct gattttttgcg gtataagaat atatactgat atgtataccc   1380
gaagtatgtc aaaaagaggt atgctatgaa gcagcgtatt acagtgacag ttgacagcga   1440
cagctatcag ttgctcaagg catatatgat gtcaatatct ccggtctggt aagcacaacc   1500
atgcagaatg aagcccgtcg tctgcgtgcc gaacgctgga aagcggaaaa tcaggaaggg   1560
atggctgagt cgcccggtt tattgaaatg aacggctctt ttgctgacga gaacaggggc   1620
tggtgaaatg cagtttaagg tttacaccta aaaagagag agccgttatc gtctgtttgt    1680
ggatgtacag agtgatatta ttgacacgcc cgggcgacgg atggtgatcc ccctggccag   1740
tgcacgtctg ctgtcagata aagtctcccg tgaactttac ccggtggtgc atatcgggga   1800
tgaaagctgg cgcatgatga ccaccgatat ggccagtgtg ccggtttccg ttatcgggga   1860
agaagtggct gatctcagcc accgcgaaaa tgacatcaaa aacgccatta acctgatgtt   1920
ctggggaata taaggtctcg cctcttgccc atcgaacgta caagtactcc tctgttctct   1980
ccttcctttg ctttaaaatg aagtgaagtt cctatacttt ctagagaata ggaacttcta   2040
tagtgagtcg aataagggcg acacaaaatt tattctaaat gcataataaa tactgataac   2100
atcttatagt ttgtattata ttttgtatta tcgttgacat gtataatttt gatatcaaaa   2160
actgattttc cctttattat tttcgagatt tattttctta attctcttta acaaactaga   2220
aatattgtat atacaaaaaa tcataaataa tagatgaata gtttaattat aggtgttcat   2280
caatcgaaaa agcaacgtat cttatttaaa gtgcgttgct ttttttctcat ttataaggtt   2340
aaataattct catatatcaa gcaaagtgac aggcgcccct aaatattctg acaaatgctc   2400
tttccctaaa ctccccccat aaaaaaaccc gccgaagcgg ttttttacgt tatttgcgga   2460
ttaacgatta ctcgttatca gaaccgccca gggggcccga gcttaagact ggccgtcgtt   2520
ttacaacaca gaaagagttt gtagaaacgc aaaaaggcca tccgtcaggg gccttctgct   2580
tagtttgatg cctggcagtt ccctactctc gccttccgct tcctcgctca ctgactcgct   2640
gcgctcggtc gttcggctgc ggcgagcggt atcagctcac tcaaaggcgg taatacggtt   2700
atccacagaa tcagggggata acgcaggaaa gaacatgtga gcaaaaggcc agcaaaaggc   2760
caggaaccgt aaaaaggccg cgttgctggc gttttttccat aggctccgcc cccctgacga   2820
gcatcacaaa aatcgacgct caagtcagag gtggcgaaac ccgacaggac tataaagata   2880
ccaggcgttt cccctggaa gctccctcgt gcgctctcct gttccgaccc tgccgcttac   2940
cggatacctg tccgcctttc tcccttcggg aagcgtggcg ctttctcata gctcacgctg   3000
taggtatctc agttcggtgt aggtcgttcg ctccaagctg ggctgtgtgc acgaaccccc   3060
cgttcagccc gaccgctgcg ccttatccgg taactatcgt cttgagtcca acccggtaag   3120
acacgactta tcgccactgg cagcagccac tggtaacagg attagcagag cgaggtatgt   3180
aggcggtgct acagagttct tgaagtggtg ggctaactac ggctacacta agaacagt    3240
```

| | |
|---|---|
| atttggtatc tgcgctctgc tgaagccagt taccttcgga aaaagagttg gtagctcttg | 3300 |
| atccggcaaa caaaccaccg ctggtagcgg tggttttttt gtttgcaagc agcagattac | 3360 |
| gcgcagaaaa aaaggatctc aagaagatcc tttgatcttt tctacggggt ctgacgctca | 3420 |
| gtggaacgac gcgcgcgtaa ctcacgttaa gggattttgg tcatgagctt gcgccgtccc | 3480 |
| gtcaagtcag cgtaatgctc tgcttt | 3506 |

<210> SEQ ID NO 45
<211> LENGTH: 3506
<212> TYPE: DNA
<213> ORGANISM: Artificial Sequence
<220> FEATURE:
<223> OTHER INFORMATION: Sequence of plasmid pBCbbn

<400> SEQUENCE: 45

| | |
|---|---|
| tagaaaaact catcgagcat caaatgaaac tgcaatttat tcatatcagg attatcaata | 60 |
| ccatattttt gaaaaagccg tttctgtaat gaaggagaaa actcaccgag gcagttccat | 120 |
| aggatggcaa gatcctggta tcggtctgcg attccgactc gtccaacatc aatacaacct | 180 |
| attaatttcc cctcgtcaaa aataaggtta tcaagtgaga aatcaccatg agtgacgact | 240 |
| gaatccggtg agaatggcaa aagtttatgc atttctttcc agacttgttc aacaggccag | 300 |
| ccattacgct cgtcatcaaa atcactcgca tcaaccaaac cgttattcat tcgtgattgc | 360 |
| gcctgagcga ggcgaaatac gcgatcgctg ttaaaaggac aattacaaac aggaatcgag | 420 |
| tgcaaccggc gcaggaacac tgccagcgca tcaacaatat tttcacctga atcaggatat | 480 |
| tcttctaata cctggaacgc tgtttttccg gggatcgcag tggtgagtaa ccatgcatca | 540 |
| tcaggagtac ggataaaatg cttgatggtc ggaagtggca taaattccgt cagccagttt | 600 |
| agtctgacca tctcatctgt aacatcattg gcaacgctac ctttgccatg tttcagaaac | 660 |
| aactctggcg catcgggctt cccatacaag cgatagattg tcgcacctga ttgcccgaca | 720 |
| ttatcgcgag cccatttata cccatataaa tcagcatcca tgttggaatt taatcgcggc | 780 |
| ctcgacgttt cccgttgaat atggctcata ttcttccttt ttcaatatta ttgaagcatt | 840 |
| tatcagggtt attgtctcat gagcggatac atatttgaat gtatttagaa aaataaacaa | 900 |
| ataggggtca gtgttacaac caattaacca attctgaaca ttatcgcgag cccatttata | 960 |
| cctgaatatg gctcataaca ccccttgttt gcctggcggc agtagcgcgg tggtcccacc | 1020 |
| tgaccccatg ccgaactcag aagtgaaacg ccgtagcgcc gatggtagtg tggggactcc | 1080 |
| ccatgcgaga gtagggaact gccaggcatc aaataaaacg aaaggctcag tcgaaagact | 1140 |
| gggcctttcg cccgggctaa ttaggggtg tcgcccttat tcgactctat agtgaagttc | 1200 |
| ctattctcta gaaagtatag gaacttctga agtggggcgg atcgatgtac acaaccgact | 1260 |
| gcacccaaac gaacacaaat cttagcagtg cggagaccgg cttactaaaa gccagataac | 1320 |
| agtatgcata tttgcgcgct gattttttgcg gtataagaat atatactgat atgtataccc | 1380 |
| gaagtatgtc aaaagagggt atgctatgaa gcagcgtatt acagtgacag ttgacagcga | 1440 |
| cagctatcag ttgctcaagg catatatgat gtcaatatct ccggtctggt aagcacaacc | 1500 |
| atgcagaatg aagcccgtcg tctgcgtgcc gaacgctgga agcggaaaa tcaggaaggg | 1560 |
| atggctgagg tcgcccggtt tattgaaatg aacggctctt tgctgacga gaacaggggc | 1620 |
| tggtgaaatg cagtttaagg tttacaccta taaagagag agccgttatc gtctgtttgt | 1680 |
| ggatgtacag agtgatatta ttgacacgcc cgggcgacgg atggtgatcc ccctggccag | 1740 |
| tgcacgtctg ctgtcagata aagtctcccg tgaactttac ccggtggtgc atatcgggga | 1800 |

```
tgaaagctgg cgcatgatga ccaccgatat ggccagtgtg ccggtttccg ttatcgggga    1860
agaagtggct gatctcagcc accgcgaaaa tgacatcaaa aacgccatta acctgatgtt    1920
ctggggaata taaggtctcg cctcacgctt ccggcatct tccagaccac agtatatcca    1980
tccgcctcct gttgaaaatg aagtgaagtt cctatacttt ctagagaata ggaacttcta    2040
tagtgagtcg aataagggcg acacaaaatt tattctaaat gcataataaa tactgataac    2100
atcttatagt ttgtattata ttttgtatta tcgttgacat gtataatttt gatatcaaaa    2160
actgattttc cctttattat tttcgagatt tattttctta attctcttta caaactaga    2220 aatattgtat atacaaaaaa tcataaataa tagatgaata gtttaattat aggtgttcat    2280
caatcgaaaa agcaacgtat cttatttaaa gtgcgttgct tttttctcat ttataaggtt    2340
aaataattct catatatcaa gcaaagtgac aggcgccctt aaatattctg acaaatgctc    2400
tttccctaaa ctcccccat aaaaaaaccc gccgaagcgg gtttttacgt tatttgcgga    2460
ttaacgatta ctcgttatca gaaccgccca ggggcccga gcttaagact ggccgtcgtt    2520
ttacaacaca gaaagagttt gtagaaacgc aaaaaggcca tccgtcaggg gccttctgct    2580
tagtttgatg cctggcagtt ccctactctc gccttccgct tcctcgctca ctgactcgct    2640
gcgctcggtc gttcggctgc ggcgagcggt atcagctcac tcaaaggcgg taatacggtt    2700
atccacagaa tcaggggata acgcaggaaa gaacatgtga gcaaaaggcc agcaaaaggc    2760
caggaaccgt aaaaaggccg cgttgctggc gtttttccat aggctccgcc cccctgacga    2820
gcatcacaaa aatcgacgct caagtcagag gtggcgaaac ccgacaggac tataaagata    2880
ccaggcgttt ccccctggaa gctccctcgt gcgctctcct gttccgaccc tgccgcttac    2940
cggatacctg tccgcctttc tcccttcggg aagcgtggcg ctttctcata gctcacgctg    3000
taggtatctc agttcggtgt aggtcgttcg ctccaagctg ggctgtgtgc acgaaccccc    3060
cgttcagccc gaccgctgcg ccttatccgg taactatcgt cttgagtcca acccggtaag    3120
acacgactta tcgccactgg cagcagccac tggtaacagg attagcagag cgaggtatgt    3180
aggcggtgct acagagttct tgaagtggtg ggctaactac ggctacacta agaacagt      3240 atttggtatc tgcgctctgc tgaagccagt taccttcgga aaaagagttg gtagctcttg    3300
atccggcaaa caaccaccg ctggtagcgg tggtttttt gtttgcaagc agcagattac      3360
gcgcagaaaa aaggatctc aagaagatcc tttgatcttt tctacggggt ctgacgctca     3420
gtggaacgac gcgcgcgtaa ctcacgttaa gggattttgg tcatgagctt cgccgtccc     3480 gtcaagtcag cgtaatgctc tgcttt                                         3506
```

<210> SEQ ID NO 46
<211> LENGTH: 3506
<212> TYPE: DNA
<213> ORGANISM: Artificial Sequence
<220> FEATURE:
<223> OTHER INFORMATION: Sequence of plasmid pCDbbn

<400> SEQUENCE: 46

```
tagaaaaact catcgagcat caaatgaaac tgcaatttat tcatatcagg attatcaata     60
ccatattttt gaaaaagccg tttctgtaat gaaggagaaa actcaccgag gcagttccat    120
aggatggcaa gatcctggta tcggtctgcg attccgactc gtccaacatc aatacaacct    180
attaatttcc cctcgtcaaa ataaggtta tcaagtgaga atcaccatg agtgacgact       240 gaatccggtg agaatggcaa aagtttatgc atttctttcc agacttgttc aacaggccag    300
```

```
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgttttccg gggatcgcag tggtgagtaa ccatgcatca     540
tcaggagtac ggataaaatg cttgatggtc ggaagtggca taaattccgt cagccagttt    600
agtctgacca tctcatctgt aacatcattg caacgctac ctttgccatg tttcagaaac     660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900 atagggggtca gtgttacaac caattaacca attctgaaca ttatcgcgag cccatttata   960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140 gggccttcg cccgggctaa ttaggggtg tcgcccttat tcgactctat agtgaagttc     1200
ctattctcta gaaagtatag gaacttctga agtggggacg cttccggca tcttccagac    1260 cacagtatat ccatccgcct cctgttggtg cggagaccgg cttactaaaa gccagataac   1320
agtatgcata tttgcgcgct gattttttgcg gtataagaat atatactgat atgtataccc   1380
gaagtatgtc aaaagaggt atgctatgaa gcagcgtatt acagtgacag ttgacagcga    1440
cagctatcag ttgctcaagg catatatgat gtcaatatct ccggtctggt aagcacaacc   1500
atgcagaatg aagcccgtcg tctgcgtgcc gaacgctgga aagcggaaaa tcaggaaggg   1560
atggctgagg tcgcccggtt tattgaaatg aacggctctt ttgctgacga gaacaggggc   1620
tggtgaaatg cagtttaagg tttacaccta taaaagagag agccgttatc gtctgtttgt    1680
ggatgtacag agtgatatta ttgacacgcc cgggcgacgg atggtgatcc cctggccag   1740 tgcacgtctg ctgtcagata aagtctcccg tgaactttac ccggtggtgc atatcgggga   1800
tgaaagctgg cgcatgatga ccaccgatat ggccagtgtg ccggtttccg ttatcgggga   1860
agaagtggct gatctcagcc accgcgaaaa tgacatcaaa aacgccatta acctgatgtt   1920
ctggggaata taaggtctcg cctcaacgtt gtccaggttt gtatccacgt gtgtccgttc   1980
cgccaatatt ccgcaaaatg aagtgaagtt cctatacttt ctagagaata ggaacttcta   2040
tagtgagtcg aataagggcg acacaaaatt tattctaaat gcataataaa tactgataac   2100
atcttatagt ttgtattata ttttgtatta tcgttgacat gtataatttt gatatcaaaa   2160
actgattttc cctttattat tttcgagatt tattttctta attctcttta acaaactaga   2220
aatattgtat atacaaaaaa tcataaataa tagatgaata gtttaattat aggtgttcat   2280
caatcgaaaa agcaacgtat cttatttaaa gtgcgttgct tttttctcat ttataaggtt   2340
aaataattct catatatcaa gcaaagtgac aggcgccctt aaatattctg acaaatgctc   2400
tttccctaaa ctcccccat aaaaaaaccc gccgaagcgg ttttttacgt tatttgcgga    2460
ttaacgatta ctcgttatca gaaccgccca gggggcccga gcttaagact ggccgtcgtt   2520
ttacaacaca gaaagagttt gtagaaacgc aaaaaggcca tccgtcaggg gccttctgct   2580
tagtttgatg cctggcagtt ccctactctc gccttccgct tcctcgctca ctgactcgct   2640
gcgctcggtc gttcggctgc ggcgagcggt atcagctcac tcaaaggcgg taatacggtt   2700
```

```
atccacagaa tcaggggata acgcaggaaa gaacatgtga gcaaaaggcc agcaaaaggc    2760
caggaaccgt aaaaaggccg cgttgctggc gttttt ccat aggctccgcc ccc ctgacga    2820 gcatcacaaa aatcgacgct caagtcagag gtggcgaaac ccgacaggac tataaagata    2880
ccaggcgttt ccccctggaa gctccctcgt gcgctctcct gttccgaccc tgccgcttac    2940
cggatacctg tccgccttt c tcccttcggg aagcgtggcg ctttctcata gctcacgctg    3000
taggtatctc agttcggtgt aggtcgttcg ctccaagctg ggctgtgtgc acgaaccccc    3060
cgttcagccc gaccgctgcg ccttatccgg taactatcgt cttgagtcca acccggtaag    3120
acacgactta tcgccactgg cagcagccac tggtaacagg attagcagag cgaggtatgt    3180
aggcggtgct acagagttct tgaagtggtg gctaactac ggctacacta agaacagt    3240 atttggtatc tgcgctctgc tgaagccagt taccttcgga aaagagttg gtagctcttg    3300 atccggcaaa caaaccaccg ctggtagcgg tggttttttt gtttgcaagc agcagattac    3360
gcgcagaaaa aaaggatctc aagaagatcc tttgatcttt tctacggggt ctgacgctca    3420
gtggaacgac gcgcgcgtaa ctcacgttaa gggattttgg tcatgagctt gcgccgtccc    3480
gtcaagtcag cgtaatgctc tgcttt                                          3506
```

<210> SEQ ID NO 47
<211> LENGTH: 3506
<212> TYPE: DNA
<213> ORGANISM: Artificial Sequence
<220> FEATURE:
<223> OTHER INFORMATION: Sequence of plasmid pD3bbn

<400> SEQUENCE: 47

```
tagaaaaact catcgagcat caaatgaaac tgcaatttat tcatatcagg attatcaata      60
ccatattttt gaaaaagccg tttctgtaat gaaggagaaa actcaccgag gcagttccat     120
aggatggcaa gatcctggta tcggtctgcg attccgactc gtccaacatc aatacaacct     180
attaatttcc cctcgtcaaa aataaggtta tcaagtgaga atcaccatg agtgacgact     240 gaatccggtg agaatggcaa aagtttatgc atttctttcc agacttgttc aacaggccag     300
ccattacgct cgtcatcaaa atcactcgca tcaaccaaac cgttattcat tcgtgattgc     360
gcctgagcga ggcgaaatac gcgatcgctg ttaaaaggac aattacaaac aggaatcgag     420
tgcaaccggc gcaggaacac tgccagcgca tcaacaatat tttcacctga atcaggatat     480
tcttctaata cctggaacgc tgtttttccg gggatcgcag tggtgagtaa ccatgcatca     540
tcaggagtac ggataaaatg cttgatggtc ggaagtggca taaattccgt cagccagttt     600
agtctgacca tctcatctgt aacatcattg gcaacgctac ctttgccatg tttcagaaac     660
aactctggcg catcgggctt cccatacaag cgatagattg tcgcacctga ttgcccgaca     720
ttatcgcgag cccatttata cccatataaa tcagcatcca tgttggaatt taatcgcggc     780
ctcgacgttt cccgttgaat atggctcata ttcttccttt tcaatatta ttgaagcatt     840 tatcagggtt attgtctcat gagcggatac atatttgaat gtatttagaa aaataaacaa     900
ataggggtca gtgttacaac caattaacca attctgaaca ttatcgcgag cccatttata     960
cctgaatatg gctcataaca cccc ttgttt gcctggcggc agtagcgcgg tggtcccacc    1020
tgaccccatg ccgaactcag aagtgaaacg ccgtagcgcc gatggtagtg tggggactcc    1080
ccatgcgaga gtagggaact gccaggcatc aaataaaacg aaaggctcag tcgaaagact    1140
gggcctttcg cccgggctaa ttagggggtg tcgcccttat tcgactctat agtgaagttc    1200
```

```
ctattctcta gaaagtatag gaacttctga agtggggacg ctttccggca tcttccagac      1260
cacagtatat ccatccgcct cctgttggtg cggagaccgg cttactaaaa gccagataac      1320
agtatgcata tttgcgcgct gattttttgcg gtataagaat atatactgat atgtataccc     1380
gaagtatgtc aaaagaggt atgctatgaa gcagcgtatt acagtgacag ttgacagcga       1440
cagctatcag ttgctcaagg catatatgat gtcaatatct ccggtctggt aagcacaacc      1500
atgcagaatg aagcccgtcg tctgcgtgcc gaacgctgga agcggaaaa tcaggaaggg       1560
atggctgagg tcgcccggtt tattgaaatg aacggctctt ttgctgacga aacaggggc      1620
tggtgaaatg cagtttaagg tttacaccta taaaagagag agccgttatc gtctgtttgt      1680
ggatgtacag agtgatatta ttgacacgcc cgggcgacgg atggtgatcc ccctggccag     1740
tgcacgtctg ctgtcagata aagtctcccg tgaactttac ccggtggtgc atatcgggga     1800
tgaaagctgg cgcatgatga ccaccgatat ggccagtgtg ccggtttccg ttatcgggga     1860
agaagtggct gatctcagcc accgcgaaaa tgacatcaaa aacgccatta acctgatgtt     1920
ctggggaata taaggtctcg cctcaacgtt gtccaggttt gtatccacgt gtgtccgttc     1980
cgccaatatt ccgcaaaatg aagtgaagtt cctatacttt ctagagaata ggaacttcta    2040
tagtgagtcg aataagggcg acacaaaatt tattctaaat gcataataaa tactgataac    2100
atcttatagt ttgtattata ttttgtatta tcgttgacat gtataatttt gatatcaaaa    2160
actgattttc cctttattat tttcgagatt tattttctta attctcttta acaaactaga    2220
aatattgtat atacaaaaaa tcataaataa tagatgaata gtttaattat aggtgttcat    2280
caatcgaaaa agcaacgtat cttatttaaa gtgcgttgct ttttttctcat ttataaggtt    2340
aaataattct catatatcaa gcaaagtgac aggcgcccct aaatattctg acaaatgctc    2400
tttccctaaa ctccccccat aaaaaaaccc gccaagcgg ttttttacgt tatttgcgga      2460
ttaacgatta ctcgttatca gaaccgccca gggggcccga gcttaagact ggccgtcgtt    2520
ttacaacaca gaaagagttt gtagaaacgc aaaaaggcca tccgtcaggg gccttctgct    2580
tagtttgatg cctggcagtt ccctactctc gccttccgct tcctcgctca ctgactcgct    2640
gcgctcggtc gttcggctgc ggcgagcggt atcagctcac tcaaaggcgg taatacggtt    2700
atccacagaa tcagggata acgcaggaaa gaacatgtga gcaaaaggcc agcaaaaggc    2760
caggaaccgt aaaaaggccg cgttgctggc gttttttccat aggctccgcc ccctgacga    2820
gcatcacaaa aatcgacgct caagtcagag gtggcgaaac ccgacaggac tataaagata    2880
ccaggcgttt cccctggaa gctccctcgt gcgctctcct gttccgaccc tgccgcttac    2940
cggataccctg tccgccttc tcccttcggg aagcgtggcg ctttctcata gctcacgctg    3000
taggtatctc agttcggtgt aggtcgttcg ctccaagctg ggctgtgtgc acgaacccc     3060
cgttcagccc gaccgctgcg ccttatccgg taactatcgt cttgagtcca acccggtaag    3120
acacgactta tcgccactgg cagcagccac tggtaacagg attagcagag cgaggtatgt    3180
aggcggtgct acagagttct tgaagtggtg ggctaactac ggctacacta agaacagt      3240
atttggtatc tgcgctctgc tgaagccagt taccttcgga aaagagttg gtagctcttg     3300
atccggcaaa caaccaccg ctggtagcgg tggtttttttt gtttgcaagc agcagattac    3360
gcgcagaaaa aaaggatctc aagaagatcc tttgatcttt tctacggggt ctgacgctca    3420
gtggaacgac gcgcgcgtaa ctcacgttaa gggattttgg tcatgagctt gcgccgtccc    3480
gtcaagtcag cgtaatgctc tgcttt                                          3506
```

```
<210> SEQ ID NO 48
<211> LENGTH: 2692
<212> TYPE: DNA
<213> ORGANISM: Artificial Sequence
<220> FEATURE:
<223> OTHER INFORMATION: Sequence containing the adhE (E.coli) DNA
      sequence codon-pair optimized for expression in S. cerevisiae

<400> SEQUENCE: 48
ggtctcgaat ggccgttact aacgtcgctg aattgaacgc tttggttgaa agagtcaaga      60
aggctcaaag agaatacgct tctttcaccc aagaacaagt cgacaagatc ttcagagccg     120
ccgccttggc tgctgctgac gctagaattc cattagctaa gatggctgtt gctgaatctg     180
gtatgggtat tgtcgaagat aaggttatta gaaccatttc gcttctgaa tacatctaca     240
acgcctacaa ggacgaaaag acttgtggtg tcttgtctga agatgacact ttcggtacta     300
tcactatcgc tgaaccaatc ggtatcatct gtggtatcgt tccaaccact aacccaactt     360
ctaccgccat cttcaaatcc ttgatctctt taaagaccag aaacgctatt atcttctctc     420
ctcacccacg tgccaaggat gctaccaaca aggctgctga tattgtcttg caagctgcta     480
ttgctgctgg tgctccaaag gacttgatcg gttggatcga ccaaccatct gtcgaattat     540
ccaatgcttt gatgcaccac ccagatatca acttgatctt ggctaccggt ggtccaggta     600
tggttaaggc tgcttactct tccggtaagc cagctattgg tgtcggtgct ggtaacactc     660
tgttgttat cgatgaaact gctgacatca aaagagctgt tgcctccgtc ttgatgtcca     720
agactttcga caacggtgtc atctgtgctt ctgaacaatc tgttgttgtt gtcgattccg     780
tctacgacgt tgttagagaa cgttttgcta cccacggtgg ttacttgttg caaggtaagg     840
aattgaaggc tgtccaagat gtcatcttga gaacggtgc tttgaatgct gccattgtcg     900
gtcaaccagc ttacaagatt gccgaattgg ctggtttctc cgttccagaa acaccaaga     960
ttttgattgg tgaagtcacc gttgttgacg aatccgaacc atttgctcac gaaaagttgt    1020
ctccaacctt ggctatgtac agagccaagg acttcgaaga tgccgtcgaa aaagctgaaa    1080
agttggttgc tatgggtggc attggtcaca ctcttgtttt gtacactgac aagacaacc    1140
aacctgccag agtctcttac ttcggtcaaa agatgaaaac tgctagaatc ttaatcaaca    1200
ctccagcttc ccaaggtggt attggtgatt tgtacaactt caagttggcc ccatctttga    1260
ctttaggttg tggttcttgg ggtggtaact ccatctctga aacgttggt ccaaagcact    1320
tgatcaacaa gaaaactgtt gctaagagag ctgaaaacat gttgtggcac aagttaccaa    1380
aatccatcta cttcagaaga ggttctttgc aattgccttt ggacgaagtc attaccgacg    1440
gtcacaagag agccttgatt gttaccgata gattcttgtt caacaacggt tacgctgacc    1500
aaatcacttc tgttttgaag gccgccggtg ttgaaactga gtttttcttc gaagtcgaag    1560
ctgatccaac tttgtctatc gttagaaagg gtgctgaatt ggctaactct ttcaagcctg    1620
atgttatcat tgctttgggt ggtggttctc caatggacgc tgccaagatc atgtgggtta    1680
tgtacgaaca tccagaaacc catttcgaag aattggcttt aagattcatg gatatcagaa    1740
agagaatcta caagttccca agatgggtg ttaaggccaa aatgattgct gtcaccacca    1800
cctccggtac tggttctgaa gttacccat ttgctgtcgt caccgatgac gctactggtc    1860
aaaagtaccc attggctgat tacgctttga ccccagacat ggctatcgtt gatgctaact    1920
tggttatgga catgccaaag tctttgtgtg ccttcggtgg tctagacgct gtcacccacg    1980
ctatggaagc ttacgtttcc gtcttggctt ccgaatttc tgacggtcaa gctttacaag    2040
ctttgaaatt gttgaaagaa tacttgccag cctcctacca cgaaggttct aagaacccag    2100
```

```
ttgctagaga aagagttcac tctgctgcca ccattgctgg tattgccttt gctaacgctt    2160
tcttgggtgt ctgtcactcc atggctcaca agttgggttc tcaattccac atcccacacg    2220
gtttggccaa cgctttgttg atctgtaacg tcattagata caacgctaac gacaacccaa    2280
ccaagcaaac tgccttctcc caatacgata gaccacaagc tagacgtcgt tatgctgaaa    2340
tcgctgacca cttgggttta tctgctccag gtgatcgtac tgccgccaag attgaaaagt    2400
tattggcttg gttagaaact ttaaaggctg aactaggtat tccaaagtct atcagagaag    2460
ctggtgtcca agaagctgac ttcttagcca acgttgacaa attgtccgaa gatgctttcg    2520
acgaccaatg taccggtgct aacccaagat acccattgat ctccgaattg aagcaaattt    2580
tgttggacac ctactacggt agagactacg ttgaaggtga aactgccgct aagaaggaag    2640
ctgctccagc taaggctgaa aagaaggcta agaaatcggc ataaaggaga cc            2692
```

<210> SEQ ID NO 49
<211> LENGTH: 1384
<212> TYPE: DNA
<213> ORGANISM: Artificial Sequence
<220> FEATURE:
<223> OTHER INFORMATION: Sequence containing the acdH (L. plantarum) DNA
      sequence codon-pair optimized for expression in S. cerevisiae

<400> SEQUENCE: 49

```
ggtctcgaat gttgaaggaa atggaagaaa ctactgtttc tcgttccatt gacagattgg      60
ttttgaatgc ctccttggct gccaacagat ggaagtcat ggaccaatct caagttgacc     120
aagctgttgc cgctatggcc agagccgctc acgctgctcg tggtatgttg gctgctatgg     180
ctgtcgaaga aaccggtaga ggtaactaca gagacaaggt tgccaaaaac gattttgctg     240
ccaagaacgt ctacaactac atcaaggatg acaagactgt cggtatcatc aacgatgacc     300
ctgtttctgg tgtcatgaag gtcgctgaac ctgttggtat cattgccggt gttaccccag     360
tcaccaaccc aacttccact gtcatcttca acgctatgtt agctttgaaa accagaaacc     420
caattatctt tggtttccac ccattcgctc aaaagtcttg tgttgaaact ggtagaatca     480
tcagagatgc tgctattgct tctggtgctc caaggactg gatccaatgg atcaagaccc     540
catctttgga agctaccaac actttgatga accatccagg tgttgccact atcattgcta     600
ccggtggtgc cggtatggtc aagaccgctt actccactgg taagccagct ttaggtgtcg     660
gtccaggtaa cgtcccatgt tcattgaac aaaccgctga tatccaacaa gctgtttccg     720
atgtcgttac ctccaagtct ttcgataacg gtatgatctg tgcttctgaa tccaacttga     780
ttgttgctga ccaaatctac gaccaagtca agagagaatt gtctcacaac ggtgtctact     840
tcgttggtac tgaaaacttc aaggctctag aagctactgt tatgaacttg gacaagcaag     900
ctgtcgatcc aaaaggttgcc ggtcaaaccc catggcaaat gcccaatgg gctggtttcg     960 atgtcccatc tgacaccaag gttttagctg ttgaattgcc atccattggt ggtgaccaag    1020
tcttgtccag agaaaagttg tctccagttt tggctgtcgt tcacgctaag gacactgaag    1080
ctggtttcaa cttgatgaag agatctttgg ctttgggtgg tttaggtcac accgccgctt    1140
tgcacaccac tgacgaagct gtcatgaaca aattcgcttt ggaaatgacc gcttgtagag    1200
ctttgatcaa cgttccatct tctcaaggtg ccattggtta caaatacgac aatgttgctc    1260
catctttgac tttgggttgt ggtacttggg gtcacaactc catctctcac aacttggaag    1320
attgggactt gttgaacatc aagactgttg ctaagagatt aaccaaaata agataaagga    1380
gacc                                                                1384
```

<210> SEQ ID NO 50
<211> LENGTH: 1420
<212> TYPE: DNA
<213> ORGANISM: Artificial Sequence
<220> FEATURE:
<223> OTHER INFORMATION: Sequence containing the eutE (E. coli) DNA
      sequence codon-pair optimized for expression in S. cerevisiae

<400> SEQUENCE: 50

```
ggtctcgaat gaaccaacaa gatattgaac aagttgtcaa ggctgttcta ttgaagatgc      60
aatcttctga cactccatct gctgccgtcc acgaaatggg tgttttcgct tctttggacg     120
atgctgttgc tgctgctaag gttgctcaac aaggtttgaa atccgttgcc atgagacaat     180
tggccattgc tgccattaga gaagctggtg aaaagcatgc ccgtgacttg gctgaattgg     240
ctgtctctga accggtatgg gtagagttga agataaatt cgctaagaac gttgctcaag      300
ctcgtggtac tccaggtgtc gaatgtttgt ctcctcaagt cttgaccggt gacaacggtt     360
tgactttgat tgaaaacgct ccatgggtg ttgttgcttc cgttactcca tctactaatc      420
cagctgccac cgtcatcaac aatgctatct ctttgatcgc tgccggtaac tccgttatct     480 tgctccaca cccagctgct aagaaagtct ctcaaagagc catcactttg ttgaaccaag      540
ccatcgttgc cgctggtggt ccagaaaact gttggtcac tgttgctaac ccagatatcg      600
aaaccgctca agattattc aagttcccag gtatcggtct attagtcgtt accggtggtg      660
aggctgttgt cgaagctgct agaaagcaca ctaacaagag attgattgct gctggtgctg     720
gtaacccacc tgttgttgtc gatgaaaccg ctgatttggc cagagctgct caatccattg     780
tcaagggtgc ttctttcgac aacaacatca tctgtgctga tgaaaaggtt ttgatcgttg     840
ttgactccgt tgctgacgaa ttgatgagat tgatggaagg tcaacatgcc gtcaagttga     900
ccgctgaaca agctcaacaa ttgcaaccag tcttgttgaa gaacattgac gaaagaggta     960
agggtactgt tccagagac tgggttggta gagatgctgg taagatcgct gctgccatcg     1020
gtttgaaggt tccacaagaa accagattat tgttcgtcga accactgct gaacacccat      1080 tcgctgtcac tgaattaatg atgccagtct tgccagttgt ccgtgttgcc aacgttgccg     1140
acgctattgc tttggctgtc aaattggaag gtggttgtca ccacactgct gctatgcact     1200
ccagaaacat tgaaaacatg aaccaaatgg ctaacgccat tgacacttcc atcttcgtca     1260
agaacggtcc atgtatcgct ggtttgggtt taggtggtga aggttggacc accatgacca     1320
tcactacccc aaccggtgaa ggtgtcactt ctgccagaac ctttgtcaga ttaagaagat     1380
gtgtcttggt cgacgctttc agaattgtgt aaaggagacc                          1420
```

<210> SEQ ID NO 51
<211> LENGTH: 1426
<212> TYPE: DNA
<213> ORGANISM: Artificial Sequence
<220> FEATURE:
<223> OTHER INFORMATION: Sequence containing the Lin1129 (L.innocua) DNA
      sequence codon-pair optimized for expression in S. cerevisiae

<400> SEQUENCE: 51

```
ggtctcgaat ggaatctttg gaattggaac aattggtcaa gaaggtctta ttggaaaaat      60
tggctgaaca aaaggaagtt ccaaccaaga ccaccaccca agtgctaaa tccggtgtct      120 ttgacactgt cgatgaagct gtccaagctg ctgtcatcgc tcaaaactgt tacaaggaaa     180
aatccttgga agaaagaaga aacgttgtca aggccatcag agaagctttg tacccagaaa     240
```

```
tcgaaactat cgctaccaga gctgttgctg aaactggtat gggtaatgtc actgacaaga      300
ttttgaagaa cactttggcc attgaaaaga ccccaggtgt tgaagatttg tacactgaag      360
ttgccactgg tgacaacggt atgactttat acgaattgtc tccatacggt gtcatcggtg      420
ccgttgcccc atctaccaac ccaaccgaaa ctttgatttg taactctatc ggtatgttgg      480
ctgctggtaa tgctgttttc tactctccac acccaggtgc taagaacatc tctttatggt      540
tgattgaaaa gttgaacacc attgtcagag actcttgtgg tattgacaac ttgattgtca      600
ctgttgccaa gccatccatc caagccgctc aagaaatgat gaaccaccca aaggttccat      660
tattggtcat caccggtggt cctggtgttg ttttgcaagc tatgcaatct ggtaagaagg      720
ttatcggtgc tggtgccggt aacccaccat ccattgtcga cgaaactgcc aacatcgaaa      780
aggctgctgc tgatatcgtt gacggtgctt ctttcgacca acatccta tgtattgctg       840 aaaaatccgt tgttgccgtc gattccattg ctgatttctt gttgttccaa atggaaaaga      900
acggtgcttt gcacgtcacc aacccatctg acatccaaaa attggaaaag gttgccgtta      960
ctgacaaggg tgtcaccaac aagaaattgg ttggtaagtc tgctactgaa attttgaagg     1020
aagctggtat tgcttgtgat ttcacccca gattaatcat cgtcgaaact gaaaagtccc       1080 acccttcgc taccgttgaa ttgttgatgc aatcgttcc agttgtcaga gttccagatt        1140
tcgacgaagc tttggaagtt gctatcgaat agaacaagg tttgcaccac accgctacca      1200
tgcactctca aaacatctcc agattgaaca aggctgctag acatgcaa acctccatct        1260 tcgttaagaa cggtccatct ttcgctggtt taggtttcag aggtgaaggt tccaccactt     1320
tcaccattgc tactccaact ggtgaaggca ccactactgc cagacatttt gctcgtcgta     1380
gaagatgtgt cttgactgat ggtttctcta tacgctaaag gagacc                   1426
```

<210> SEQ ID NO 52  
<211> LENGTH: 2626  
<212> TYPE: DNA  
<213> ORGANISM: Artificial Sequence  
<220> FEATURE:  
<223> OTHER INFORMATION: Sequence containing the adhE (S. aureus) DNA  
      sequence codon-pair optimized for expression in S. cerevisiae

<400> SEQUENCE: 52

```
ggtctcgaat gttgaccatt ccagaaaagg aaacagagg ttccaaggaa caagaagttg        60
ctattatgat tgacgctttg gctgacaaag gtaagaaggc tttggaagct ctatccaaga     120
agtcccaaga agaaattgac cacattgtcc accaaatgtc tttggccgct gttgaccaac     180
acatggtctt ggctaagttg gctcacgaag aaactggtag aggtatctac gaagataagg     240
ccatcaagaa cttgtacgct tctgaataca tctggaactc catcaaggac aacaagactg     300
tcggtatcat cggtgaagat aaagaaaagg gtttgactta cgttgctgaa ccaattggtg     360
ttatctgtgg tgtcaccca actaccaacc caacctctac caccattttc aaggctatga     420
ttgccattaa gactggtaac cctatcatct ttgctttcca cccatctgct caagaatctt     480
ccaagagagc tgctgaagtt gttttggaag ccgctatgaa ggccggtgct ccaaaggata     540
tcatccaatg gattgaagtt ccatccatcg aagccactaa gcaattgatg aaccacaagg     600
gtattgcttt agttttagcc actggtggtt ccggtatggt caagtccgct tactccaccg     660
gtaagccagc cttgggtgtt ggtccaggta acgtcccatc ctacattgag aaaaccgctc     720
acattaagcg tgctgttaac gacatcattg gttctaagac tttcgacaat ggtatgatct     780
gtgcttctga acaagttgtt gttatcgaca aggaaatcta caaggatgtc accaacgaat     840
```

```
tcaaggctca tcaagcttac ttcgtcaaga aggacgaatt gcaaagatta gaaaatgcta      900
tcatgaacga acaaaagacc ggtatcaaac cagacattgt cggtaagtct gctgttgaaa      960
ttgctgaatt ggccggtatt ccagtcccag aaaacaccaa gttgatcatt gctgaaattt     1020
ctggtgtcgg ttctgactac ccattgtcta gagaaaagtt gtctccagtc ttggctttgg     1080
ttaaggctca atccaccaag caagctttcc aaatctgtga agatactttg cacttcggtg     1140
gtttgggtca taccgctgtc attcacactg aagatgaaac tttgcaaaaa gatttcggtc     1200
taagaatgaa ggcctgtaga gtcttggtca acactccatc cgctgttggt ggtattggtg     1260
acatgtacaa cgaattgatt ccatctttga ctttgggttg tggttcttac ggtagaaact     1320
ccatctctca aacgtttct gctaccgact tgttgaacat caagaccatt gccaagagaa       1380
gaaacaacac tcaaatcttc aaggttccag ctcaaatcta ctttgaagaa acgccatca       1440 tgtccttgac caccatggac aagatcgaaa aggtcatgat cgtttgtgac ccaggtatgg     1500
ttgaattcgg ttacaccaag accgttgaaa acgtcttaag acaaagaact gaacaaccac     1560
aaatcaaaat tttctccgaa gtcgaaccaa cccatccac taacaccgtt tacaagggtt       1620
tagaaatgat ggtcgatttc caaccagata ccattattgc tttgggtggt ggttctgcca     1680
tggacgctgc taaggccatg tggatgttct tcgaacatcc agaaacttct ttcttcggtg     1740
ccaagcaaaa gttcttggat atcggtaagc gtacctacaa gattggtatg ccagaaaacg     1800
ctactttcat ctgtatccca actacttccg gtactggttc cgaagtcact ccatttgctg     1860
ttatcactga ttctgaaacc aacgtcaagt acccattggc tgacttcgct ttgaccccag     1920
atgttgctat catcgaccca caattcgtca tgtccgttcc aaaatctgtc actgctgaca     1980
ccggtatgga cgttttgacc cacgctatgg aatcttacgt ttccgttatg gcctccgatt     2040
acaccagagg tttatctttg caagctatca aattgacttt cgaatactta aaatcttctg     2100
tcgaaaaagg tgacaaggtt ccagagaaaa gatgcacaa cgcttctact ttggctggta      2160
tggcctttgc caacgctttc ttgggtatcg ctcactctat tgctcacaag atcggtggtg     2220
aatacggtat cccacatggt agagctaacg ctatcttatt gcctcacatc atccgttaca     2280
acgctaagga ccctcaaaag cacgcttttgt tcccaaagta cgaattcttc agagctgaca   2340
ctgactacgc tgatatcgct aagttcttag gtttgaaggg taacactact gaagctttgg     2400
tcgaatcttt ggccaaggct gtttacgaat gggtcaatc tgttggtatc gaaatgaact      2460
tgaaatctca aggtgtctct gaagaagaat tgaacgaatc tattgacaga atggccgaat     2520
tggctttcga agatcaatgt accaccgcca acccaaagga agctttgatc tctgaaatca     2580
aggatattat ccaaacttct tacgattaca agcaataaag gagacc                    2626
```

<210> SEQ ID NO 53
<211> LENGTH: 2068
<212> TYPE: DNA
<213> ORGANISM: Artificial Sequence
<220> FEATURE:
<223> OTHER INFORMATION: Sequence containing the ACS2 (S. cerevisiae)
      DNA sequence codon-pair optimized for expression in S. cerevisiae

<400> SEQUENCE: 53

```
ggtctcgaat gaccatcaag gaacacaagg ttgtctacga agctcacaac gtcaaggctt       60
tgaaagctcc tcaacatttc tacaactctc aaccaggtaa gggttacgtt accgatatgc      120
aacactacca agaaatgtac caacaatcca tcaacgaacc agaaaaattc ttcgacaaga     180
tggctaagga atacttgcac tgggatgctc catacaccaa ggttcaatcc ggttcccttga    240
```

```
acaacggtga tgtcgcttgg ttcttgaacg gtaaattgaa tgcttcctac aactgtgtcg      300
atcgtcacgc tttcgctaac ccagacaaac cagctttgat ttacgaagct gatgacgaat      360
ctgacaacaa gatcatcact ttcggtgaac tattaagaaa ggtttctcaa atcgctggtg      420
tcttgaaatc ctggggtgtt aagaagggtg acactgttgc catctacttg ccaatgatcc      480
cagaagctgt tattgctatg ttggctgtcg ccagaattgg tgccattcac tctgttgttt      540
tcgctggttt ctctgccggt tctttgaagg acagagtcgt tgacgctaac tctaaggttg      600
tcatcacttg tgacgaaggt aagagaggtg gtaagaccat taacactaag aagattgtcg      660
acgaaggttt gaacggtgtt gatttggttt ccagaatctt ggttttccaa agaaccggta      720
ctgaaggtat tccaatgaag gctggtagag actactggtg gcatgaagaa gccgctaagc      780
aaagaactta cctaccacct gtttcctgtg atgctgaaga tccattgttt ttgttgtaca      840
cctctggttc taccggttct ccaaagggtg ttgtccacac taccggtggt tacttgttgg      900
gtgctgcttt gaccaccaga tacgtctttg acatccaccc tgaagatgtc ttattcactg      960
ctggtgacgt cggttggatc actggtcata cctacgcttt gtacggtcca ttgactttag     1020
gtactgcttc tatcatcttc gaatccaccc cagcttaccc agactacggt agatactgga     1080
gaatcattca aagacacaag gccacccact tctacgtcgc cccaactgcc ttgagattaa     1140
tcaagagagt tggtgaagct gaaattgcta aatacgatac ctcttctttg agagtcttag     1200
gttctgtcgg tgaaccaatt tctccagact tatgggaatg gtatcacgaa aaggttggta     1260
acaagaactg tgtcatctgt gacaccatgt ggcaaactga atctggttct cacttgattg     1320
ctccattggc tggtgctgtt ccaactaagc caggttccgc taccgttcca ttcttcggta     1380
tcaacgcttg tatcattgac ccagtcactg gtgtcgaatt ggaaggtaac gatgttgaag     1440
gtgtcttggc cgtcaagtct ccatggccat ccatggctag atctgtctgg aaccaccacg     1500
atcgttacat ggacacctac ttgaaaccat acccaggtca ctacttcacc ggtgatggtg     1560
ccggtcgtga ccacgatggt tactactgga tcagaggtcg tgttgatgac gttgttaacg     1620
tttctggtca cagattgtcc acttctgaaa tcgaagcctc catctccaac catgaaaacg     1680
tttccgaagc tgctgtcgtt ggtattccag acgaattgac cggtcaaact gttgttgctt     1740
acgtttcttt aaaggacggt tacttgcaaa acaacgccac tgaaggtgac gctgaacaca     1800
tcactccaga taacttaaga agagaattga ttttgcaagt tcgtggtgaa attggtccat     1860
ttgcttcccc aaagaccatc attttggtta gagacttgcc aagaaccaga tctggtaaga     1920
tcatgagaag agtcttgaga aaggttgcct ccaatgaggc tgaacaattg ggtgacttga     1980
ctactttggc caacccagaa gtcgtcccag ctatcatttc tgctgtcgaa aaccaattct     2040
tctcccaaaa gaagaaataa aggagacc                                        2068
```

<210> SEQ ID NO 54
<211> LENGTH: 1120
<212> TYPE: DNA
<213> ORGANISM: Artificial Sequence
<220> FEATURE:
<223> OTHER INFORMATION: Sequence containing the gldA (E. coli) DNA
      sequence codon-pair optimized for expression in S. cerevisiae

<400> SEQUENCE: 54

```
ggtctcgaat ggacagaatc atccaatctc caggtaagta catccaaggt gctgatgtta       60
tcaacagatt aggtgaatac ttgaagccat tggctgaaag atggttagtc gtcggtgaca      120
aattcgtttt gggtttcgct caatccaccg tcgaaaagtc tttcaaggat gctggtttgg      180
```

```
ttgttgaaat cgctccattc ggtggtgaat gttctcaaaa tgaaattgac cgtttgagag      240
gtattgctga aactgctcaa tgtggtgcca tcttgggtat tggtggtggt aagactttgg      300
acactgccaa ggctttggcc cacttcatgg gtgttccagt tgccattgct ccaaccattg      360
cttctaccga tgctccatgt tctgctttgt ccgttatcta caccgacgaa ggtgaatttg      420
accgttactt gttgttgcca aacaacccaa acatggtcat tgtcgacacc aagatcgttg      480
ccggtgctcc agccagatta ttggctgccg gtatcggtga tgctttggct acctggttcg      540
aagccagagc ttgttccaga tctggtgcta ctaccatggc cggtggtaaa tgtactcaag      600
ctgctttagc tttggctgaa ttgtgttaca cactttgtt ggaagaaggc gaaaaggcta      660
tgttggctgc tgaacaacac gttgttactc cagctttgga aagagtcatt gaagccaaca      720
cctacttgtc cggtgttgga ttcgaatctg gtggtttagc tgccgctcat gccgtccaca      780
acggtttgac tgccatccca gatgctcacc actactacca cggtgaaaag gttgctttcg      840
gtactttgac tcaattagtc ttggaaaacg ctccagtcga agaaatcgaa accgttgctg      900
ctctatccca cgctgtcggt tgcctatca ctttggctca attggacatc aaggaagatg      960
tcccagctaa gatgagaatt gttgctgaag ctgcttgtgc tgaaggtgaa accattcaca     1020
acatgccagg tggtgccacc ccagaccaag tctacgctgc tttgttggtt gctgaccaat     1080
acggtcaaag attcttgcaa gaatgggagt aaaggagacc                           1120
```

<210> SEQ ID NO 55
<211> LENGTH: 1114
<212> TYPE: DNA
<213> ORGANISM: Artificial Sequence
<220> FEATURE:
<223> OTHER INFORMATION: Sequence containing the gldA (K. pneumoniae)
      DNA sequence codon-pair optimized for expression in S. cerevisiae

<400> SEQUENCE: 55

```
ggtctcgaat gttgaaggtt atccaatctc cagccaaata cttgcaaggt ccagatgctg       60
ctgtcttatt cggtcaatac gccaagaact tggctgaatc tttcttcgtt atcgctgatg      120
actttgtcat gaaattggct ggtgaaaaag ttgttaacgg tctacaatct cacgacatca      180
gatgtcatgc tgaaagattc aacggtgaat gttcccacgc tgaaatcaac cgtttgatgg      240
ctatcttaca aaagcaaggt tgtagaggtg ttgtcggtat cggtggtggt aagactttgg      300
ataccgctaa ggccatcggt tactaccaaa agttgccagt tgttgtcatt ccaaccattg      360
cttccactga cgctccaact tctgccttgt ccgtcatcta cactgaagct ggtgaattcg      420
aagaatactt gatctaccca aagaacccag acatggttgt tatggacacc gccattatcg      480
ccaaggctcc agtcagattg ttggtttccg gtatgggtga tgctttgtct acctggttcg      540
aagccaaggc ttgttacgac gctagagcta cctccatggc cggtggtcaa tctaccgaag      600
ctgctttgtc cttggctaga ttatgttacg acactttatt ggctgaaggc gaaaaggcca      660
gattagctgc tcaagctggt gttgtcactg aagccttgga agaatcatt gaagctaaca      720 cctacttgtc tggtattggt ttcgaatctt ctggtttggc tgctgctcac gctattcaca      780
acggtttcac catcttggaa gaatgtcacc acttgtacca tggtgaaaag gttgctttcg      840
gtactttggc tcaattagtc ttgcaaaact ctccaatgga cgaaatcgaa accgttttgg      900
gtttctgtca aagagttggt tgcctgtca ctttggccca aatgggtgtc aaggaaggta      960
ttgatgctaa gattgctgct gttgccaagg ctacctgtgc tgaaggtgaa accattcaca     1020
acatgccatt tgctgtcact ccagaatccg tccacgctgc catcttgact gctgattgt      1080
```
tgggtcaaca atggttggct cgataaagga gacc                   1114

<210> SEQ ID NO 56
<211> LENGTH: 1120
<212> TYPE: DNA
<213> ORGANISM: Artificial Sequence
<220> FEATURE:
<223> OTHER INFORMATION: Sequence containing the gldA (E. aerogenes)
      DNA sequence codon-pair optimized for expression in S. cerevisiae

<400> SEQUENCE: 56
ggtctcgaat ggacagaatc atccaatctc caggtaagta catccaaggt gctggtgcca       60
tcaagagatt aggtgaatac ttgaagccat tggctgaaag atggttaatc attggtgaca      120
agttcgtctt gggttttgct gaagaacaat tgagaacctc tttgggtggt gccggtttgg      180
ttgctgaaat tgctccattc ggtggtgaat gttcccaaaa cgaaatcaac agattaagag      240
acattgcttc ttctgctcaa tgtcacgctg tcttgggtat tggtggtggt aagacttttgg      300 acaccgctaa ggctttggcc cactacatgc atttgccagt tgttgttgct ccaaccattg      360
cttccaccga tgctccatgt tctgctttgt ctgtcatcta caccgatgac ggtgaattcg      420
aatcctactt gatgttgcct cacaacccaa acatggttgt tgtcgacact caaatcgttg      480
ctgctgcccc agccagattg ttggccgctg gtatcggtga tgctttggcc acctggttcg      540
aagccagagc ttgttcccgt tctggtgcta ccaccatggc tggtggtaaa tgtacccaag      600
ccgctttggc tttggctgaa ttgtgttaca acactttagt cgaagagggt gaaaaagcca      660
tgttagctgc tgaacaacac gttgtcactc cagcttggga acgtgtcatt gaagctaaca      720
cctacttgtc cggtgttgga ttcgaatctg gtggtttggc tgctgctcac gctattcaca      780
acggtttgac tgccatccca gatgctcacc acttctacca tggtgaaaag gttgccttcg      840
gtactttgac tcaattggtt ttggaaaacg ctccagtcga agaaattgaa actgctgctg      900 cttttgtgtca ctccgttggt ttgccaatca ctttggctca attggatatc aagggtgaca      960
tcccagccaa gatgagaact gttgctgaag ctgcttgtgc cgaaggtgaa accattcaca     1020
acatgccagg tgtgcttgt gctgaccaag tctacgctgc tctattagtc gccgaccaat     1080
acggtcaaag attcttgcaa gaatgggagt aaaggagacc                          1120

<210> SEQ ID NO 57
<211> LENGTH: 1111
<212> TYPE: DNA
<213> ORGANISM: Artificial Sequence
<220> FEATURE:
<223> OTHER INFORMATION: Sequence containing the gldA (Y. aldovae) DNA
      sequence codon-pair optimized for expression in S. cerevisiae

<400> SEQUENCE: 57
ggtctcgaat gttgaaggtc atccaatctc catctaagta catccaaggt gccaacgctt       60
tgcaatccat tggtgaattt gccaagttgt tggctaacaa ctacttcatc attgctgatg      120
actttgtcat gaaattgact gctgacaccg ttggtacttc tttgcaaacc tgtgaattga      180
aatctcactt ctccagattc aacggtgaat gttccagaca agaaatcgaa agattgaccg      240
tcgaattgaa gaaatacggt tgtaatggtg tcatcggtat cggtggtggt aagacttttgg      300 acaccgctaa ggccattgct cactaccaac acatcccagt tgttgttgtc ccaaccattg      360
cttctaccga tgctccaact tctgctttgt ccgtcatcta cactgaacaa ggtgaattcg      420
ctgaatactt gatctaccca aagaacccag acattgtctt gatggacacc accatcattg      480
ccaaggctcc agtcagattg ttggttgctg gtatgggtga tgctctatcc acctacttcg      540

```
aagctcaagc ctgtttcgat gccaaggcca tctccatggc tggtggtgct tccactttgg      600
ctgccatcac tttggccaga ttatgttacg aaactttatt ggctgaaggt tacaaggcca      660
agttggctgt tgaagctggt gttgtcactg aagctgtcga acgtattatt gaagctaaca      720
cctacttgtc tggtattggt ttcgaatctt ctggtttggc tgctgctcat gccatccaca      780
acggtttcac cgttttggaa gaatgtcacc acttgtacca tggtgaaaag gttgctttcg      840
gtactttgac tcaattggtt ttgcaaaact cttccatgga agaaattgaa accgtcttgt      900
ctttctgtca acaattaggt ttgccaatca ctttagctga aatgggtgtc actcaagatt      960
tggaatgtaa gatcagagct gttgctcaag cttcttgtgc tgaaggtgaa accattcaca     1020
acatgccatt caaggttacc gctgactctg tttacgccgc tatcatcgtt gctgacagat     1080
taggtcaagc tttcctcaac taaaggagac c                                    1111
```

<210> SEQ ID NO 58
<211> LENGTH: 1111
<212> TYPE: DNA
<213> ORGANISM: Artificial Sequence
<220> FEATURE:
<223> OTHER INFORMATION: Sequence containing the DAK1 (S. cerevisiae)
      DNA sequence codon-pair optimized for expression in S. cerevisiae <400> SEQUENCE: 58

```
ggtctcgaat gttgaaggtc atccaatctc catctaagta catccaaggt gccaacgctt       60
tgcaatccat tggtgaattt gccaagttgt tggctaacaa ctacttcatc attgctgatg      120
actttgtcat gaaattgact gctgacaccg ttggtacttc tttgcaaacc tgtgaattga      180
aatctcactt ctccagattc aacggtgaat gttccagaca agaaatcgaa agattgaccg      240
tcgaattgaa gaaatacggt tgtaatgtgt tcatcggtat cggtggtggt aagactttgg      300
acaccgctaa ggccattgct cactaccaac acatcccagt tgttgttgtc ccaaccattg      360
cttctaccga tgctccaact tctgctttgt ccgtcatcta cactgaacaa ggtgaattcg      420
ctgaatactt gatctaccca agaacccag acattgtctt gatggacacc accatcattg      480
ccaaggctcc agtcagattg ttggttgctg gtatgggtga tgctctatcc acctacttcg      540
aagctcaagc ctgtttcgat gccaaggcca tctccatggc tggtggtgct tccactttgg      600
ctgccatcac tttggccaga ttatgttacg aaactttatt ggctgaaggt tacaaggcca      660
agttggctgt tgaagctggt gttgtcactg aagctgtcga acgtattatt gaagctaaca      720
cctacttgtc tggtattggt ttcgaatctt ctggtttggc tgctgctcat gccatccaca      780
acggtttcac cgttttggaa gaatgtcacc acttgtacca tggtgaaaag gttgctttcg      840
gtactttgac tcaattggtt ttgcaaaact cttccatgga agaaattgaa accgtcttgt      900
ctttctgtca acaattaggt ttgccaatca ctttagctga aatgggtgtc actcaagatt      960
tggaatgtaa gatcagagct gttgctcaag cttcttgtgc tgaaggtgaa accattcaca     1020
acatgccatt caaggttacc gctgactctg tttacgccgc tatcatcgtt gctgacagat     1080
taggtcaagc tttcctcaac taaaggagac c                                    1111
```

<210> SEQ ID NO 59
<211> LENGTH: 1771
<212> TYPE: DNA
<213> ORGANISM: Artificial Sequence
<220> FEATURE:
<223> OTHER INFORMATION: equence containing the dhaK (K. pneumoniae)
      DNA sequence codon-pair optimized for expression in S. cerevisiae

<400> SEQUENCE: 59

```
ggtctcgaat gtccgctaaa tctttcgaag ttaccgaccc agtcaactct tctttgaagg      60
gttttgcttt ggccaaccca tccattactt tggtcccaga agaaaagatc ttattcagaa     120
agactgactc tgacaaaatt gctttgatct ccggtggtgg ttccggtcac gaaccaaccc     180
acgctggttt catcggtaag ggtatgttgt ccggtgctgt cgttggtgaa atctttgctt     240
ctccatccac caagcaaatc ttgaatgcta tcagattagt caacgaaaac gcttctggtg     300
tcttgttgat tgtcaagaac tacactggtg acgtcttgca tttcggttta tctgctgaaa     360
gagctagagc tttgggtatt aactgtagag ttgccgtcat cggtgacgat gttgctgtcg     420
gtcgtgaaaa gggtggtatg gttggtagac gtgctttggc tggtactgtc ttggttcaca     480
agattgttgg tgctttcgct gaagaatact cctccaagta cggtttagat ggtactgcta     540
aggttgccaa gatcatcaac gacaacttgg ttaccatcgg ttcttctttg gaccactgta     600
aggttccagg tagaaagttc gaatctgaat tgaacgaaaa gcaaatggaa ttgggtatgg     660
gtatccacaa cgaaccaggt gttaaggtct tggacccaat tccatccact gaagatttga     720
tttccaaata catgttgcca aagttgctag acccaaacga caaggacaga gctttcgtta     780
agttcgatga agatgacgaa gttgtttttgt tggtcaacaa cttgggtggt gtttctaact     840
tcgtcatctc ttctattacc tccaagacca ccgatttctt aaaggaaaac tacaacatca     900
ctccagtcca aaccattgcc ggtactttga tgacctcttt caacggtaac ggtttctcca     960
tcaccttgtt gaatgccacc aaagctacca aggctttgca atctgatttc gaagaaatca    1020
aatccgtctt agatttgttg aacgccttca ccaacgcccc aggttggcca attgctgact    1080
tcgaaaagac ctctgctcca tctgttaacg atgacttgtt gcacaacgaa gttactgcca    1140
aggccgtcgg tacttacgat ttcgacaaat tcgctgaatg gatgaagtct ggtgctgaac    1200
aagtcatcaa atctgaacca cacatcactg aattggacaa ccaagttggt gatggtgact    1260
gtggttacac tttggttgct ggtgtcaagg gtatcactga aaacttggac aaaattgtcca    1320
aggactcttt gtctcaagct gttgctcaaa tttctgattt cattgaaggt tccatgggtg    1380
gtacttctgg tggtttgtac tccatcttgt tgtctggttt ctcccacggt ttgatccaag    1440
tttgtaagtc caaggatgaa cctgtcacca aggaaattgt tgccaagtct ctaggtattg    1500
ctttggacac tttatacaag tacaccaagg ccagaaaggg ttcttccacc atgatcgatg    1560
ctttggaacc atttgtcaag gaattcactg cttctaagga cttcaacaag gctgttaagg    1620
ctgctgaaga aggtgccaag tccactgcta cttttcgaagc taagttcggt agagcttctt    1680
acgttggtga ctcttctcaa gttgaagatc caggtgctgt tggtttatgt gaattcttga    1740
agggtgtcca atctgcgctt taaaggagac c                                    1771
```

<210> SEQ ID NO 60
<211> LENGTH: 1735
<212> TYPE: DNA
<213> ORGANISM: Artificial Sequence
<220> FEATURE:
<223> OTHER INFORMATION: Sequence containing the DAK1 (Y. lipolytica) DNA sequence codon-pair optimized for expression in S. cerevisiae

<400> SEQUENCE: 60

```
ggtctcgaat gactaccaag caattccaat tcgactctga cccattgaac tctgctttgg      60
ccgctactgc tgaagcttct ggtttagctt acttgccaaa gtccaaggtc atctactacc     120
cattgactaa cgacaaggtt actttgatct ccggtggtgg tgctggtcac gaaccagctc     180
```

| | |
|---|---|
| aaactggttt cgttggtcct ggtttgttgg atgctgccgt ttccggtcaa atcttcgctt | 240 |
| ccccatccac caagcaaatc atcgctggtg tcaatgctgt caaatctcaa agaggttcca | 300 |
| ttatcatcgt catgaactac actggtgatg tcattcactt cggtatggct gctgaacaat | 360 |
| taagatccag atacgactac catgctgaat tggtttccat cggtgatgac atttctgtca | 420 |
| acaagaaggc tggtagaaga ggtctagctg gtactgtttt ggttcacaag attgccggtc | 480 |
| acttggctcg tgacggttgg gatgtcgtgt ttttggccga agctttgaga accactgctg | 540 |
| ctaacttggc cactgttgct gcttccttgg aacactgtac cgtcccaggt agaaagttcg | 600 |
| aaactgaatt ggccgctgac gaaatggaaa tcggtatggg tattcacaat gaaccaggtg | 660 |
| tcaaaaccat caagatcggt aaggttgaat ctttattgga cgaattagtc gacaaatttg | 720 |
| aaccttctaa gcaagatttc gttccattca acaaaggtga cgaagttgtc ttgttggtca | 780 |
| actctttggg tggtgtttct tctttggaat tgcatgccat tgctaacatt gcccaaacca | 840 |
| aattcgaaaa ggttttgggt gtcaagaccg tcagattgat tgttggtaac ttcatggctg | 900 |
| ctttcaacgg tccaggtttc tctttgacct tgttgaacgt taccactacc gctaagaagg | 960 |
| gtaactttga cgtcttgggt gccttggatg ccccagtttc caccgctgct tggccatctt | 1020 |
| tgcaacaaaa ggataaacca gctaacgtg tgttcaaga agaaaaggaa actgactctg | 1080 |
| acaagccagc tgaaccaacc ggtatcaagg ctgatggtaa attattcaag gctatgattg | 1140 |
| aatctgctgt cgatgacttg aagaaggaag aaccacaaat caccaagtac gacactattg | 1200 |
| ctggtgacgg tgactgtggt gaaactctat tagctggtgg tgatggtatc ttggatgcta | 1260 |
| tcaagaacaa gaagatcgac ttggacgatg ctgctggtgt tgctgatatc tctcacattg | 1320 |
| ttgaaaactc tatgggtggt acttctggtg gtttatactc catcttcttc tctggttttgg | 1380 |
| ttgttggtat taaggaaacc aaggccaagg aattgtccgt cgacgtcttt gccaaggcct | 1440 |
| gtgaaactgc cttggaaact ttatccaagt acacccaagc tcgtgtcggt gacagaacct | 1500 |
| tgatggatgc tttggttcca ttcgttgaaa ctttgtctaa gaccaaggat ttcgctaagg | 1560 |
| ctgtcgaagc tgctagaaag ggtgccgacg aaacctccaa attgccagcc aacttcggta | 1620 |
| gagcttctta cgttaacgaa gaaggttttgg aaaacattcc agacccaggt gctttgggtt | 1680 |
| tggccgttat cttcgaaggt ttattgaagg cttgggaaaa gaaataaagg agacc | 1735 |

<210> SEQ ID NO 61
<211> LENGTH: 1759
<212> TYPE: DNA
<213> ORGANISM: Artificial Sequence
<220> FEATURE:
<223> OTHER INFORMATION: Sequence containing the DAK1 (S. pombe) DNA
    sequence codon-pair optimized for expression in S. cerevisiae

<400> SEQUENCE: 61

| | |
|---|---|
| ggtctcgaat ggacaagcac ttcatcaacg acccagaagt cttagtcttg gacggtttga | 60 |
| aatctttggc tgacatgaac aagactttga ccgtccacga gaaggtaag ttcatctact | 120 |
| tccacgacta caacaagaag aacgtttccg ttatctccgg tggtggtgct ggtcatgaac | 180 |
| caactcactc ttctttcgtc ggtaagggta tgttgactgc tgctgttttcc ggttccatct | 240 |
| tgcctctcc atcttccaag caaatctaca ccggtatcaa gcaagtcgaa tctgaagctg | 300 |
| gtactttggt tatctgtaag aactacactg gtgatatctt gcacttcggt atggctttgg | 360 |
| aaaagcaaag aactgctggt aagaaggctg aattgattgc cgttgctgac gatgtctctg | 420 |
| tcggtagaaa gaagtctggt aaggttggta gaagaggttt atctggtact gtcttggttc | 480 |

```
acaagattgc tggtgctgct gctgcccgtg gtttgccatt agaagctgtc accaccattg    540
ccaaggctgc cattgacaac ttagtctcta tcggtgcttc cttggctcat gttcacgttc    600
caggtcacga accaattgct aaggaagatg aaatgaagca cgatgaaatg gaattgggta    660
tgggtatcca caacgaacct ggttgtaaga gaatctctcc aatcccatcc attgatgact    720
tgattgctca aatgttgaaa caaatgttgg accaatctga caaggatcgt gcttacgtca    780
aaatcgaagg tgacgacgaa gttgtcttgt tgatgaacaa cttgggtggt ctatccatgt    840
tggaattctc tgccatttct cacaaggtca aggaagcttt agctaaggaa tacaagatta    900
accctgttag aatcttcgct ggtccattca ccacctcttt gaatggtcta ggtttcggta    960
tcactttgtt gagaaccact gacagagtca aggttgaagg tgaagaatac tctttggttg   1020
atttgattga ccaaccagtt gaagctattg gttggccatt gtgtcaacca tctgatttga   1080
aatccaagaa caagattggt aacgtttcca ttgaagaagg tcaaaaggac gttaaatctc   1140
cagttaccgt tgacaaggaa aaggttcgtc aagctatcgt caactccatg gaaaacttaa   1200
tcaaggctga accaaagatc accaaattcg acaccatggc tggtgatggt gactgtggta   1260
ctaccttgaa gagaggtgct gaaggtgtct tgaaattcgt caaatctgat aaattctctg   1320
atgacccaat cagaatcgtt agagatatcg ctgatgttat tgaagataac atggacggta   1380
cttctggtgc tttgtacgcc atcttcttcc acggtttcgc caagggtatg aaggacacct   1440
tggaaaagtc caaagatatc tcctccaaga cctgggctgc tggtttgaag gttgctttgg   1500
acactttatt caaatacact ccagccagac caggtgactc taccatgtgt gacgctttgg   1560
ttccattcgt tgaaactttt gtcaagacca acgacttgaa cgctgccgtc gaagaagcta   1620
gaaagggtgc tgatgctact gctgacatgc aagccaagtt gggtagagct gtctacgtcg   1680
gtgatgacgt caaggttcca gatgctggtg ccttgggtgt tgttgccatt gtcgaaggtt   1740
ttacgaagta aaggagacc                                                1759
```